(12) United States Patent
Lee et al.

(10) Patent No.: US 11,098,044 B2
(45) Date of Patent: Aug. 24, 2021

(54) IMIDAZOPYRIDINYL COMPOUNDS AND USE THEREOF FOR TREATMENT OF NEURODEGENERATIVE DISORDERS

(71) Applicant: 1ST Biotherapeutics, Inc., Gyeonggi-do (KR)

(72) Inventors: Jinhwa Lee, Gyeonggi-do (KR); Suyeon Jo, Gyeonggi-do (KR); Keonseung Lim, Gyeonggi-do (KR); A Yeong Park, Gyeonggi-do (KR); Jae Eun Kim, Gyeonggi-do (KR); Misoon Kim, Gyeonggi-do (KR); Seung Mook Lim, Gyeonggi-do (KR)

(73) Assignee: 1ST Biotherapeutics, Inc., Gyeonggi-Do (KR)

( * ) Notice: Subject to any disclaimer, the term of this patent is extended or adjusted under 35 U.S.C. 154(b) by 0 days.

(21) Appl. No.: 16/797,140

(22) Filed: Feb. 21, 2020

(65) Prior Publication Data

US 2020/0270246 A1 Aug. 27, 2020

Related U.S. Application Data

(60) Provisional application No. 62/809,230, filed on Feb. 22, 2019.

(51) Int. Cl.
| | | |
|---|---|---|
| *C07D 471/04* | (2006.01) | |
| *A61P 25/28* | (2006.01) | |
| *A61P 25/16* | (2006.01) | |
| *C07D 519/00* | (2006.01) | |

(52) U.S. Cl.
CPC ............ *C07D 471/04* (2013.01); *A61P 25/16* (2018.01); *A61P 25/28* (2018.01); *C07D 519/00* (2013.01)

(58) Field of Classification Search
CPC .................................................. C07D 471/04
See application file for complete search history.

(56) References Cited

U.S. PATENT DOCUMENTS

| 7,928,140 B2 | 4/2011 | Booker et al. |
|---|---|---|
| 8,053,574 B2 | 11/2011 | Bruce et al. |
| 8,993,580 B2 | 3/2015 | Ren et al. |
| 9,505,784 B2 | 11/2016 | Choi et al. |
| 2010/0075965 A1* | 3/2010 | Ni .............................. A61P 9/10 514/235.8 |
| 2011/0172228 A1 | 7/2011 | Ren et al. |
| 2019/0100500 A1 | 4/2019 | Lee et al. |

FOREIGN PATENT DOCUMENTS

| WO | WO-01/57008 A1 | 8/2001 | |
|---|---|---|---|
| WO | WO-2007/095588 A1 | 8/2007 | |
| WO | WO-2008/016131 A1 | 2/2008 | |
| WO | WO-2009/017822 A2 | 2/2009 | |
| WO | WO-2009/026254 A1 | 2/2009 | |
| WO | WO-2009/133127 A1 | 11/2009 | |
| WO | WO-10/008847 A2 | 1/2010 | |
| WO | WO-10/100144 A1 | 9/2010 | |
| WO | WO-2012080284 A2 * | 6/2012 | ................. A61P 5/00 |
| WO | WO-2014/004863 A2 | 1/2014 | |
| WO | WO-2015/134171 A1 | 9/2015 | |
| WO | WO-2018/017435 A1 | 1/2018 | |
| WO | WO-2020097400 A1 * | 5/2020 | ............ C07D 471/04 |

OTHER PUBLICATIONS

Shah "The role of fluorine in medicinal chemistry" Journal of Enzyme Inhibition and Medicinal Chemistry, Oct. 2007; 22(5): 527-540.*
International Search Report from corresponding PCT Application No. PCT/IB2020/051469, dated Jun. 4, 2020.
International Search Report from corresponding PCT Application No. PCT/IB2020/051472, dated Jun. 4, 2020.
International Search Report from corresponding PCT Application No. PCT/KR2018/011660, dated Jan. 29, 2019.
Hantschel, O., et al.; "Regulation of the C-ABL and BCR-ABL Tyrosine Kinases", Nature Reviews, Molecular Cell Biology, vol. 5, Jan. 2004, pp. 33-44.
Hebron, M. L., et al.; "Nilotinib reverses loss of dopamine neurons and improves motor behavior via autophagic degradation of a-synuclein in Parkinson's disease models", Human Molecular Genetics, 2013, vol. 22, No. 16, pp. 3315-3328.
Imamura, K., et al.; "The Src/c-Abl pathway is a potential therapeutic target in amyotrophic lateral sclerosis", Science Translational Medicine, vol. 9, May 24, 2017, pp. 1-10.
Jellinger, K. A., et al., "Multiple system atrophy: pathogenic mechanisms and biomarkers", High Impact Review in Neuroscience, Neurology or Psychiatry Review Article, J Neural Transm., 2016, pp. 1-18.
Mahul-Mellier, A., et al.; "c-Abl phosphorylates a-synuclein and regulates its degradation: implication for a-synuclein clearance and contribution to the pathogenesis of Parkinson's disease", Human Molecular Genetics, 2014, vol. 23, No. 11, pp. 2858-2879.

(Continued)

*Primary Examiner* — David K O'Dell
(74) *Attorney, Agent, or Firm* — Harness, Dickey & Pierce, P.L.C.

(57) ABSTRACT

The present disclosure provides a compound of Formula (I) or pharmaceutically acceptable salt, stereoisomers thereof, a pharmaceutical composition comprising the compound, and a method to treat or prevent neurodegenerative diseases using the compound.

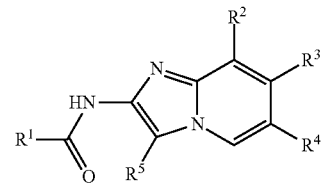

Formula I

24 Claims, No Drawings

(56) References Cited

OTHER PUBLICATIONS

Imidazo[1,2-a]pyridin-6-yl-benzamide analogs as potent RAF inhibitors, Bioorganic & Medicinal Chemistry Letters (2017), 27(23), 5221-5224.
ASK1 pharmacophore model derived from diverse classes of inhibitors, Bioorganic & Medicinal Chemistry Letters (2014), 24(18), 4418-4423.
Design and biological evaluation of imidazo[1,2-a]pyridinesas novel and potent ASK1 inhibitors, Bioorganic & Medicinal Chemistry Letters (2012), 22(24), 7326-7329.
Salovich, et al.; Bioorganic & Medicinal Chemistry Letters, 2012, 22, 5084-5088.
RN 1187453-71-9 in CALPUS, 2010.
RN 2258671-51-9 in CALPUS, 2018.

\* cited by examiner

IMIDAZOPYRIDINYL COMPOUNDS AND USE THEREOF FOR TREATMENT OF NEURODEGENERATIVE DISORDERS

CROSS-REFERENCE TO RELATED APPLICATIONS

This application claims the benefit and priority to U.S. Provisional Patent Application No. 62/809,230, filed on 22 Feb. 2019. The entire disclosure of the application identified in this paragraph is incorporated herein by reference.

FIELD

The present disclosure generally relates to compounds having enzyme inhibitory activity, pharmaceutical compositions comprising the compound, and methods of using the compounds for treating diseases.

BACKGROUND

α-synuclein is part of a large family of proteins including β- and γ-synuclein and synoretin. α-synuclein is expressed in the normal state associated with synapses and is believed to play a role in neural plasticity, learning and memory. Several studies have implicated α-synuclein with a central role in Parkinson disease pathogenesis. Molecular changes in the α-synuclein protein that increase protein misfolding and aggregation have a direct role in disease pathogenesis. Aggregation of α-synuclein contributes to the formation of Lewy bodies and neurites, the pathologic hallmarks of Parkinson disease and α-synucleinopathies. Activation of tyrosine kinase c-abl contributes to α-synuclein-induced neurodegeneration.

The tyrosine kinase c-abl is tightly regulated non-receptor protein tyrosine kinase involved in a wide range of cellular processes, including growth, survival and stress response (*Nat Rev Mol Cell Biol*, 2004, 5:33-44) and c-abl involved in regulation several cellular processes and has implicated in the development of the central nervous system by controlling neurogenesis. More recently, increasing evidence from various experimental model systems has also revealed that c-abl is activated in neurodegenerative disease such as Alzheimer's disease, Parkinson's disease, Neiman-Pick type C diseases and tauopathies. (*Human Molecular Genetics*, 2014, Vol. 23, No. 11)

The stress-signaling non-receptor tyrosine kinase c-abl links parkin to sporadic forms of Parkinson's disease via tyrosine phosphorylation. Tyrosine phosphorylation of parkin by c-abl is a major post-translational modification that leads to loss of parkin function and disease progression in sporadic Parkinson disease. Inhibition of c-abl offers new therapeutic opportunities for blocking Parkinson disease progression. (*The Journal of Neuroscience*, 2011, 31(1):157-163) Amyotrophic lateral sclerosis (ALS) is a fatal neurodegenerative disease characterized by progressive death of motor neurons. Knockdown of c-abl with small interfering RNAs (siRNAs) also rescued ALS motor neuron degeneration. (Imamura et al., *Sci. Transl. Med.* 9, 2017) Multiple System Atrophy (MSA) is a rare, rapidly progressive neurodegenerative disease without any current treatment. In MSA there is accumulation of α-synuclein in the neurons and oligodendrocytes of the substantia nigra, striatum, olivo-pontocerebellar structures and spinal cord. (*J Neural Trans Vienna Austria* 1996. 2016; 123(6))

Administration of the tyrosine kinase inhibitor nilotinib decreases c-abl activity and ameliorates autophagic clearance of α-synuclein in transgenic and lentiviral gene transfer models. Activation of c-abl in the mouse forebrain induces neurodegeneration in the hippocampus and striatum. Therefore, an increase in c-abl activity via phosphorylation may be associated with the α-synuclein pathology detected in Parkinson disease and other neurodegenerative disease. (*Hum Mol Genet*. 2013 Aug. 15).

c-abl is a potential therapeutic target for α-synucleinopathy, Parkinson disease, Alzheimer disease, ALS, Dementia with Lewy body and MSA.

Mutations in the leucine-rich repeat kinase 2 (LRRK2) gene are the most common cause of familial Parkinson disease with autosomal dominant inheritance. LRRK2 played important roles in the death of neurons via directly phosphorylating apoptosis signal-regulating kinase 1 at Thr832 site and activating the kinase activity. LRRK2 G2019S mutation impairs dopamine receptor D1 internalization, leading to an alteration in signal transduction. Parkinson disease-associated LRRK2 mutations upregulate the expression of mitochondrial calcium uniporter, a mitochondrial calcium transporter and then promote the uptake of dendritic and mitochondrial calcium in cortical neurons and familial Parkinson disease patient fibroblasts. (*Frontiers in aging Neuroscience*, 2018 April (10)) Accordingly, LRRK2 has emerged as a promising therapeutic target for disease modification in Parkinson disease.

SUMMARY

The present disclosure provides a compound having c-abl and LRRK2 kinase inhibitory activity, a composition comprising the compound and a method useful to treat a neurodegenerative disease.

In an embodiment, there are provided a compound of Formula (I) and a pharmaceutically acceptable salt thereof:

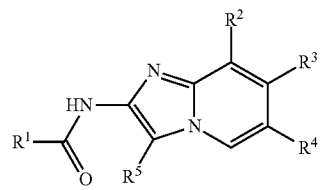

Formula I wherein $R^1$, $R^2$, $R^3$, $R^4$, and $R^5$ are as defined herebelow.

In another embodiment, the present disclosure provides pharmaceutical compositions comprising a therapeutically effective amount of a compound described herein and a pharmaceutically acceptable carrier.

In yet another embodiment, the present disclosure provides methods of inhibiting or treating a neurodegenerative disease comprising administering to a subject in need thereof a therapeutically effective amount of one or more compounds described herein.

DETAILED DESCRIPTION

The following description is merely exemplary in nature and is not intended to limit the present disclosure, application, or uses.

Definitions

The generic terms used in the present disclosure are herein defined for clarity.

This specification uses the terms "substituent", "radical", "group", "moiety", and "fragment" interchangeably.

As used herein, the term "alkenyl" refers to a straight or branched hydrocarbonyl group with at least one site of unsaturation, i.e., a carbon-carbon, sp2 double bond. In an embodiment, alkenyl has from 2 to 12 carbon atoms. In some embodiments, alkenyl is a $C_2$-$C_{10}$ alkenyl group or a $C_2$-$C_6$ alkenyl group. Examples of alkenyl group include, but are not limited to, ethylene or vinyl (—CH=$CH_2$), allyl (—$CH_2$CH=$CH_2$), cyclopentenyl (—$C_5H_7$), and 5-hexenyl (—$CH_2CH_2CH_2CH_2$CH=$CH_2$).

As used herein, the term "alkoxy" is RO— where R is alkyl. Non-limiting examples of alkoxy groups include methoxy, ethoxy and propoxy.

As used herein, the term "alkoxyalkyl" refers to an alkyl moiety substituted with an alkoxy group. Examples of alkoxyalkyl groups include methoxymethyl, methoxyethyl, methoxypropyl and ethoxyethyl.

As used herein, the term "alkoxycarbonyl" is ROC(O)—, where R is an alkyl group as defined herein. In various embodiments, R is a $C_1$-$C_{10}$ alkyl group or a $C_1$-$C_6$ alkyl group.

As used herein, the term "alkyl" refers to a straight or branched chain hydrocarbonyl group. In an embodiment, alkyl has from 1 to 12 carbon atoms. In some embodiments, alkyl is a $C_1$-$C_{10}$ alkyl group or a $C_1$-$C_6$ alkyl group. Examples of alkyl groups include, but are not limited to, methyl, ethyl, propyl, isopropyl, butyl, isobutyl, t-butyl, pentyl, hexyl, heptyl, octyl, nonyl and decyl. "lower alkyl" means alkyl having from 1 to 4 carbon atoms.

As used herein, the term "alkylamino" refers to an amino group substituted with one or more alkyl groups. "N-(alkyl) amino" is RNH— and "N,N-(alkyl)$_2$amino" is R2N—, where the R groups are alkyl as defined herein and are the same or different. In various embodiments, R is a $C_1$-$C_{10}$ alkyl group or a $C_1$-$C_6$ alkyl group. Examples of alkylamino groups include methylamino, ethylamino, propylamino, butylamino, dimethylamino, diethylamino, and methylethylamino.

As used herein, the term "alkylaminoalkyl" refers to an alkyl moiety substituted with an alkylamino group, wherein alkylamino is as defined herein. Examples of alkylaminoalkyl groups include methylaminomethyl and ethylaminomethyl.

As used herein, the term "alkynyl" refers to a straight or branched carbon-chain group with at least one site of unsaturation, i.e., a carbon-carbon, sp triple bond. In an embodiment, alkynyl has from 2 to 12 carbon atoms. In some embodiments, alkynyl is a $C_2$-$C_{10}$ alkynyl group or a $C_2$-$C_6$ alkynyl group. Examples of alkynyl groups include acetylenic (—C≡CH) and propargyl (—$CH_2$C≡CH).

As used herein, the term "aryl" refers to any monocyclic or bicyclic carbon ring of up to 7 atoms in each ring, wherein at least one ring is aromatic, or an aromatic ring system of 5 to 14 carbon atoms which includes a carbocyclic aromatic group fused with a 5- or 6-membered cycloalkyl group. Representative examples of aryl groups include, but are not limited to, phenyl, tolyl, xylyl, naphthyl, tetrahydronaphthyl, anthracenyl, fluorenyl, indenyl, azulenyl and indanyl. A carbocyclic aromatic group can be unsubstituted or optionally substituted.

As used herein, the term "cycloalkyl" is a hydrocarbyl group containing at least one saturated or partially unsaturated ring structure, and attached via a ring carbon. In various embodiments, it refers to a saturated or a partially unsaturated $C_3$-$C_{12}$ cyclic moiety, examples of which include cyclopropyl, cyclobutyl, cyclopentyl, cyclopentenyl, cyclohexyl, cyclohexenyl, cycloheptyl and cyclooctyl. "Cycloalkyloxy" is RO—, where R is cycloalkyl.

As used herein, the terms "halogen" and "halo" refers to chloro (—Cl), bromo (—Br), fluoro (—F) or iodo (—I). "Haloalkoxy" refers to an alkoxy group substituted with one or more halo groups and examples of haloalkoxy groups include, but are not limited to, —$OCF_3$, —$OCHF_2$ and —$OCH_2$F. "Haloalkoxyalkyl" refers to an alkyl moiety substituted with a haloalkoxy group, wherein haloalkoxy is as defined herein. Examples of haloalkoxyalkyl groups include trifluoromethoxymethyl, trifluoroethoxymethyl and trifluoromethoxyethyl. "Haloalkyl" refers to an alkyl moiety substituted with one or more halo groups. Examples of haloalkyl groups include —$CF_3$ and —$CHF_2$.

As used herein, the term "heteroalkyl" refers to a straight- or branched-chain alkyl group having from 2 to 14 carbons (in some embodiments, 2 to 10 carbons) in the chain, one or more of which has been replaced by a heteroatom selected from S, O, P and N. Exemplary heteroalkyls include alkyl ethers, secondary and tertiary alkyl amines, amides, alkyl sulfides, and the like.

As used herein, the term "heterocyclyl" includes the heteroaryls defined below and refers to a saturated or partially unsaturated monocyclic, bicyclic or tricyclic group of 2 to 14 ring-carbon atoms and, in addition to ring-carbon atoms, 1 to 4 heteroatoms selected from P, N, O and S. In various embodiments the heterocyclic group is attached to another moiety through carbon or through a heteroatom, and is optionally substituted on carbon or a heteroatom. Examples of heterocyclyl include azetidinyl, benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrahydrothiopyranyl, tetrahydroisoquinolinyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyridin-2-onyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof. "Heterocyclyloxy" is RO—, where R is heterocyclyl. "Heterocyclylthio" is RS—, where R is heterocyclyl.

As used herein, the term "3- or 4-membered heterocyclyl" refers to a monocyclic ring having 3 or 4 ring atoms wherein at least one ring atom is heteroatom selected from the group consisting of N, O and S. Non-limiting examples of 3- or 4-membered heterocyclyl include aziridinyl, 2H-azirinyl, oxiranyl, thiiranyl, azetidinyl, 2,3-dihyroazetyl, azetyl, 1,3-diazetidinyl, oxetanyl, 2H-oxetyl, thietanyl, and 2H-thietyl.

As used herein, the term "heteroaryl" refers to a monocyclic, bicyclic or tricyclic ring having up to 7 atoms in each ring, wherein at least one ring is aromatic and contains from 1 to 4 heteroatoms in the ring selected from the group consisting of N, O and S. Non-limiting examples of heteroaryl include pyridyl, thienyl, furanyl, pyrimidyl, imidazolyl, pyranyl, pyrazolyl, thiazolyl, thiadiazolyl, isothiazolyl, oxazolyl, isoxazoyl, pyrrolyl, pyridazinyl, pyrazinyl, quinolinyl, isoquinolinyl, benzofuranyl, dibenzofuranyl, dibenzothiophenyl, benzothienyl, indolyl, benzothiazolyl, benzooxazolyl, benzimidazolyl, isoindolyl, benzotriazolyl, purinyl, thianaphthenyl and pyrazinyl. Attachment of heteroaryl can occur via an aromatic ring, or, if heteroaryl is bicyclic or tricyclic and one of the rings is not aromatic or contains no heteroatoms, through a non-aromatic ring or a ring containing no heteroatoms. "Heteroaryl" is also understood to include the N-oxide derivative of any nitrogen containing heteroaryl. "Heteroaryloxy" is RO—, where R is heteroaryl.

As used herein, the term "hydroxyalkoxy" refers to an alkoxy group substituted with a hydroxyl group (—OH), wherein alkoxy is as defined herein. An example of hydroxyalkoxy is hydroxyethoxy.

As used herein, the term "hydroxyalkyl" refers to a linear or branched monovalent $C_1$-$C_{10}$ hydrocarbon group substituted with at least one hydroxy group and examples of hydroxyalkyl groups include, but are not limited to, hydroxymethyl, hydroxyethyl, hydroxypropyl and hydroxybutyl.

As used herein, the term "pharmaceutically acceptable" means suitable for use in pharmaceutical preparations, generally considered as safe for such use, officially approved by a regulatory agency of a national or state government for such use, or being listed in the U.S. Pharmacopoeia or other generally recognized pharmacopoeia for use in animals, and more particularly in humans.

As used herein, the term "pharmaceutically acceptable carrier" refers to a diluent, adjuvant, excipient, or carrier, or other ingredient which is pharmaceutically acceptable and with which a compound of the invention is administered.

As used herein, the term "pharmaceutically acceptable salt" refers to a salt which may enhance desired pharmacological activity. Examples of pharmaceutically acceptable salts include acid addition salts formed with inorganic or organic acids, metal salts and amine salts. Examples of acid addition salts formed with inorganic acids include salts with hydrochloric acid, hydrobromic acid, sulfuric acid, nitric acid and phosphoric acid. Examples of acid addition salts formed with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxy-benzoyl)-benzoic acid, cinnamic acid, mandelic acid, methanesulfonic acid, ethanesulfonic acid, 1,2-ethanedisulfonic acid, 2-hydroxyethane-sulfonic acid, benzenesulfonic acid, p-chlorobenzenesulfonic acid, 2-naphthalenesulfonic acid, p-toluenesulfonic acid, camphorsulfonic acid, 4-methyl-bicyclo [2.2.2]oct-2-ene1-carboxylic acid, gluco-heptonic acid, 4,4'-methylenebis(3-hydroxy-2-naphthoic) acid, 3-phenylpropionic acid, trimethyl-acetic acid, tertiary butylacetic acid, lauryl sulfuric acid, gluconic acid, glutamic acid, hydroxy-naphthoic acids, salicylic acid, stearic acid and muconic acid. Examples of metal salts include salts with sodium, potassium, calcium, magnesium, aluminum, iron, and zinc ions. Examples of amine salts include salts with ammonia and organic nitrogenous bases strong enough to form salts with carboxylic acids.

As used herein, the term "therapeutically effective amount" means when applied to a compound of the invention is intended to denote an amount of the compound that is sufficient to ameliorate, palliate, stabilize, reverse, slow or delay the progression of a disorder or disease state, or of a symptom of the disorder or disease. In an embodiment, the method of the present invention provides for administration of combinations of compounds. In such instances, the "therapeutically effective amount" is the amount of a compound of the present invention in the combination sufficient to cause the intended biological effect.

As used herein, the term "treatment" or "treating" as used herein means ameliorating or reversing the progress or severity of a disease or disorder, or ameliorating or reversing one or more symptoms or side effects of such disease or disorder. "Treatment" or "treating", as used herein, also means to inhibit or block, as in retard, arrest, restrain, impede or obstruct, the progress of a system, condition or state of a disease or disorder. For purposes of this invention, "treatment" or "treating" further means an approach for obtaining beneficial or desired clinical results, where "beneficial or desired clinical results" include, without limitation, alleviation of a symptom, diminishment of the extent of a disorder or disease, stabilized (i.e., not worsening) disease or disorder state, delay or slowing of a disease or disorder state, amelioration or palliation of a disease or disorder state, and remission of a disease or disorder, whether partial or total.

In another embodiment, the compounds of Formula (I) are used for modulating the activity of a protein kinase c-abl.

As used herein, the term "modulating" or "modulation" refers to the alteration of the catalytic activity of a protein kinase. In particular, modulating refers to the activation or inhibition of the catalytic activity of a protein kinase, depending on the concentration of the compound or salt to which the protein kinase is exposed or, more preferably, the inhibition of the catalytic activity of a protein kinase. The term "catalytic activity" as used herein refers to the rate of phosphorylation of tyrosine, serine or threonine under the influence, direct or indirect, of a protein kinase.

The three main classes that pharmacological inhibitors of kinase activity are categorized by are (1) Type I, or "DFG-in" ATP competitive inhibitors, which directly compete with ATP in the ATP binding site (i.e., Src and Abl inhibitor dasatinib, (2) Type II, or "DFG-out" ATP competitive inhibitors, which, in addition to binding the ATP binding site also engage an adjacent hydrophobic binding site that is only accessible when the kinase is in an inactivated configuration (i.e., the activation loop is oriented in a conformation that would block substrate binding) (i.e., imatinib, nilotinib), and (3) non-ATP competitive inhibitors that bind at sites outside the ATP binding site that affect the activity of the kinase (i.e. GNF-2).

As used herein, the phrase "compound(s) of this/the disclosure" includes any compound(s) of Formula (I), as well as clathrates, hydrates, solvates, or polymorphs thereof. And, even if the term "compound(s) of the disclosure" does not mention its pharmaceutically acceptable sat, the term includes salts thereof. In one embodiment, the compounds of this disclosure include stereochemically pure compounds, e.g., those substantially free (e.g., greater than 85% ee, greater than 90% ee, greater than 95% ee, greater than 97% ee, or greater than 99% ee) of other stereoisomers. That is, if the compounds of Formula (I) according to the present disclosure or salts thereof are tautomeric isomers and/or stereoisomers (e.g., geometrical isomers and conformational isomers), such isolated isomers and their mixtures also are included in the scope of this disclosure. If the compounds of the present disclosure or salts thereof have an asymmetric carbon in their structures, their active optical isomers and their racemic mixtures also are included in the scope of this disclosure.

As used herein, the term "polymorph" refers to solid crystalline forms of a compound of this disclosure or complex thereof. Different polymorphs of the same compound can exhibit different physical, chemical and/or spectroscopic properties. Different physical properties include, but are not limited to stability (e.g., to heat or light), compressibility and density (important in formulation and product manufacturing), and dissolution rates (which can affect bioavailability). Differences in stability can result from changes in chemical reactivity (e.g., differential oxidation, such that a dosage form discolors more rapidly when comprised of one polymorph than when comprised of another polymorph) or mechanical characteristics (e.g., tablets crumble on storage as a kinetically favored polymorph converts to thermodynamically more stable polymorph) or both (e.g., tablets of one polymorph are more susceptible to breakdown at high humidity). Different physical properties of polymorphs can affect their processing. For example, one polymorph might be more likely to form solvates or might be more difficult to filter or wash free of impurities than another due to, for example, the shape or size distribution of particles of it.

As used herein, the term "solvate" means a compound or its salt according to this disclosure that further includes a stoichiometric or non-stoichiometric amount of a solvent bound by non-covalent intermolecular forces. Preferred solvents are volatile, non-toxic, and/or acceptable for administration to humans in trace amounts.

As used herein, the term "hydrate" means a compound or its salt according to this disclosure that further includes a stoichiometric or non-stoichiometric amount of water bound by non-covalent intermolecular forces.

As used herein, the term "clathrate" means a compound or its salt in the form of a crystal lattice that contains spaces (e.g., channels) that have a guest molecule (e.g., a solvent or water) trapped within.

Compounds of the Present Disclosure

The present disclosure provides compounds according to Formula (I):

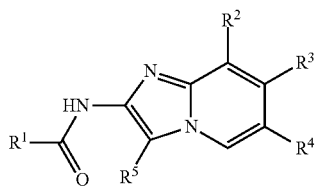

Formula I or a pharmaceutically acceptable salt thereof, wherein:

$R^1$ is cyclopropyl, cyclobutyl, or 4-membered heterocyclyl, wherein $R^1$ is optionally substituted with one or more groups selected from the group consisting of halo, alkyl, hydroxyalkyl, haloalkyl, and monoalkylaminoalkyl, $R^2$ and $R^3$ are independently —H, halo, alkyl, alkoxy, —$CF_3$, —$CHF_2$, —$CH_2F$, or —$OCF_3$, $R^4$ is aryl, heteroaryl, cycloalkyl, heterocyclyl, or heteroalkyl, wherein $R^4$ is optionally substituted with one or more groups selected from the group consisting of halo, hydroxyl, alkyl, alkenyl, alkynyl, cycloalkyl, haloalkyl, hydroxyalkyl, dialkylaminoalkyl, trimethylsilylethoxymethyl, —$CH_2NHC(O)CH_3$, —$NO_2$, —$NR_aR_b$, —$NR_aC(=O)R_b$, —$NR_aC(=O)NR_aR_b$, —$NR_aC(=O)OR_b$, —$OR_a$, —CN, —$C(=O)R_a$, —$C(=O)OR_a$, —$C(=O)NR_aR_b$, —$OC(=O)R_a$, —$OC(=O)OR_a$, —$OC(=O)NR_aR_b$, —$SR_a$, azetidinyl, oxetanyl, tetrahydrofuranyl, furanyl, pyrrolidinyl, pyrrolyl, pyrazolyl, thiophenyl, imidazolyl, oxazolyl, isoxazolyl, thiazolyl, furazanyl, oxadiazolyl, thiadiazolyl, phenyl, tetrahydropyranyl, pyranyl, pyridinyl, pyridazinyl, pyrimidinyl, pyrazinyl, piperidinyl, piperazinyl, morpholinyl and thiomorpholinyl, $R_a$ and $R_b$ are independently —H, halo, amino, alkyl, or haloalkyl, and $R^5$ is H, halo, or alkyl.

In some embodiments, $R^1$ is cyclopropyl or cyclobutyl, wherein $R^1$ is optionally substituted with one or more groups selected from the group consisting of halo, $C_1$-$C_3$ alkyl, $C_1$-$C_3$ hydroxyalkyl and $C_1$-$C_3$ haloalkyl; $R^2$ and $R^3$ are independently —H, halo, $C_1$-$C_3$ alkyl, $C_1$-$C_3$ alkoxy, —$CF_3$, —$CHF_2$, —$CH_2F$, or —$OCF_3$; $R^4$ is aryl, heteroaryl, cycloalkyl, or heterocyclyl, wherein $R^4$ is optionally substituted with one or more groups selected from the group consisting of halo, hydroxyl, $C_1$-$C_3$ alkyl, $C_2$-$C_3$ alkenyl, $C_2$-$C_3$ alkynyl, $C_3$-$C_4$ cycloalkyl, $C_1$-$C_3$ haloalkyl, mono-$C_1$-$C_3$ alkylamino, di-$C_1$-$C_3$ alkylamino, —$NO_2$, —$NR_aR_b$, —$NR_aC(=O)R_b$, —$NR_aC(=O)NR_aR_b$, —$NR_aC(=O)OR_b$, —$OR_a$, —CN, —$C(=O)R_a$, —$C(=O)OR_a$, —$C(=O)NR_aR_b$, —$OC(=O)R_a$, —$OC(=O)OR_a$, —$OC(=O)NR_aR_b$, —$SR_a$, azetidinyl, oxetanyl, tetrahydrofuranyl, furanyl, pyrrolidinyl, pyrrolyl, pyrazolyl, thiophenyl, imidazolyl, oxazolyl, isoxazolyl, thiazolyl, furazanyl, oxadiazolyl, thiadiazolyl, phenyl, tetrahydropyranyl, pyranyl, pyridinyl, pyridazinyl, pyrimidinyl, pyrazinyl, piperidinyl, piperazinyl, morpholinyl and thiomorpholinyl; $R_a$ and $R_b$ are independently —H, halo, amino, $C_1$-$C_3$ alkyl, or $C_1$-$C_3$ haloalkyl; and $R^5$ is H, F—, Cl—, Br— or methyl In various embodiments, $R^1$ is cyclopropyl or cyclobutyl, wherein $R^1$ is optionally substituted with one or more groups selected from the group consisting of halo, $C_1$-$C_3$ alkyl, $C_1$-$C_3$ hydroxyalkyl and $C_1$-$C_3$ haloalkyl. In particular embodiments, $R^1$ is cyclopropyl, fluorocyclopropyl, hydroxycyclopropyl, hydroxymethylcyclopropyl, difluorocyclopropyl, methylaminomethylcyclopropyl, cyclobutyl, fluorocyclobutyl, or difluorocyclobutyl. In other particular embodiments, $R^1$ is cyclopropyl, fluorocyclopropyl, cyclobutyl, or fluorocyclobutyl.

In some other embodiments, $R^1$ is 4-membered heterocyclyl which is optionally substituted with one or more groups selected from the group consisting of halo, $C_1$-$C_3$ alkyl, $C_1$-$C_3$ hydroxyalkyl and $C_1$-$C_3$ haloalkyl. In particular embodiments, the 4-membered heterocyclyl is selected from the group consisting of aziridinyl, 2H-azirinyl, oxiranyl, thiiranyl, azetidinyl, 2,3-dihyroazetyl, azetyl, 1,3-diazetidinyl, oxetanyl, 2H-oxetyl, thietanyl, and 2H-thietyl.

In some embodiments, $R^2$ and $R^3$ are independently —H, methyl, or fluoro.

In some embodiments, $R^4$ is phenyl, pyridinyl, pyrimidinyl, indolinyl, pyrazolyl, thiazolyl, oxoindolinyl, pyrrolopyridinyl, pyrazolyl, pyrazolopyridinyl, oxodihydropyrrolopyridinyl, oxodihydrobenzothiazolyl, benzoimidazolyl, bezooxazolyl, beznothiazolyl, thiophenyl, pyrrolopyridinyl or isothiazolyl, wherein $R^4$ is optionally substituted with one or more groups selected from the group consisting of halo, alkyl, alkenyl, alkynyl, hydroxyalkyl, amino, cyano, acetyl, hydroxy, and haloalkyl. In particular embodiments, $R^4$ is fluoro-methylphenyl, fluoro-hydroxymethylphenyl, chloro-hydroxymethylphenyl, methyl-hydroxymethylphenyl, difluoro-hydroxymethylphenyl, chloro-fluoro-hydroxymethylphenyl, fluoro-methyl-hydroxymethylphenyl, chloro-methylphenyl, dimethylphenyl, acetamido-methylphenyl, hydroxy-methylphenyl, hydroxypropanyl-methylphenyl, methyl-propenylphenyl, methyl-pyridinylethynylphenyl, methyl-pyrrolylphenyl, methyl-thiazolylphenyl, imidazolyl-methylphenyl, cyano-methylphenyl, methyl-pyrazolylphenyl, ethynyl-methylphenyl, methylpyridinyl, fluoro-methyl-methylaminophenyl, dimethylpyridinyl, fluoro-methylpyridinyl, fluoromethyl-methylpyridinyl, cyanopyridinyl, trifluoromethyl-methylpyridinyl, hydroxymethylpyridinyl, hydroxymethyl-methylpyridinyl, hydroxyethyl-methylpyridinyl, chloro-methylpyridinyl, aminopyridinyl, acetyl-methylpyridinyl, amino-dimethylpyridinyl, hydroxyethyl-methylprydinyl, methylindolyl, methyloxoindolyl, trimethylsilylethoxymethylindolyl, acetyl-methylindolinyl, methylpyrimidinyl, dimethylpyrimidinyl, trifluoromethylpyrimidinyl, pyrazolyl, methylthiazolyl, methyloxoindolinyl, pyrrolopyridinyl, methylpyrrolopyridinyl, methyl-tetrahydropyranyl, methylpyrazolyl, methyl-oxodihydrobibenzothiazolyl, pyrazolopyridinyl, oxodihydropyrrolopyridinyl, methylisothiazolyl, chloro-methylisothiazolyl, dimethylisothiazolyl, or fluoro-methyl-indolyl. In particular embodiments, $R^4$ is fluoro-methylphenyl, fluoro-hydroxymethylphenyl, chloro-hydroxymethylphenyl, methyl-hydroxymethylphenyl, difluoro-hydroxymethylphenyl, chloro-fluoro-hydroxymethylphenyl, fluoro-methyl-hydroxymethylphenyl, chloro-methylphenyl, dimethylphenyl, acetamido-methylphenyl, hydroxyl-methylphenyl, methyl-propenylphenyl, ethynyl-methylphenyl, fluoro-methyl-methylaminophenyl, fluoro-hydroxyl-methylphenyl, methyl-methylaminophenyl, methyl-pyrrolylphenyl, methyl-thiazolylphenyl, cyano-methylphenyl, imidazolyl-methylphenyl, methylpyridinyl, chloro-methylpyridinyl, fluoro-methylpyridinyl, fluoromethyl-methylpyridinyl, bimethylpyridinyl, aminopyridinyl, amino-dimethylpyridinyl, methoxypyridinyl, acetyl-methylpyridinyl, hydroxymethylpyridinyl, hydroxymethyl-methylpyridinyl, hydroxyethyl-methylpyridinyl, cyanopyridinyl, trifluoromethylpyridinyl, methylthiophenyl, methylindolinyl, methylpyrimidinyl, dimethylpyrimidinyl, pyrazolyl, methylpyrazolyl, methylindolinyl, methyloxoindolinyl, pyrrolopyridinyl, methylpyrrolopyridinyl, methylpyrrolyl, pyrazolopyridinyl, dihydropyrrolopyridinyl, methylisothiazolyl, dimethylisothiazolyl, methylindazolyl, or methyl-benzothiazolyl. In particular embodiments, $R^4$ is pyridinyl or phenyl that has one or more substitutions selected from the group consisting of alkyl, alkenyl, alkynyl, cycloalkyl, halo, hydroxyl, hydroxyalkyl, haloalkyl, cyano, amino, alkoxy, alkoxyalkoxyalkyl, alkoxyalkyl, and haloalkoxy. In some particular embodiments, $R^4$ is selected from the group consisting of:

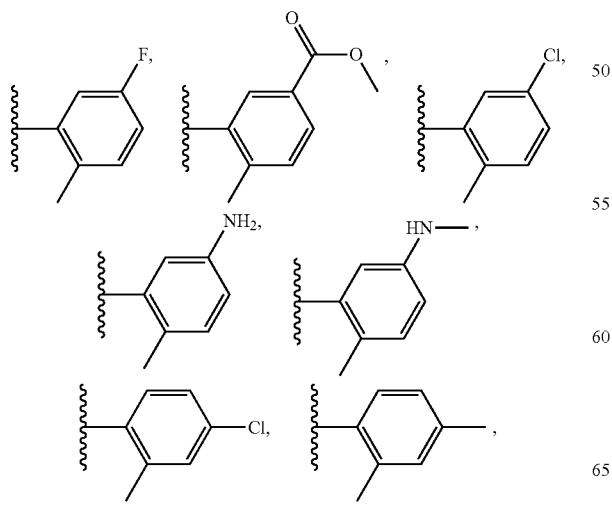

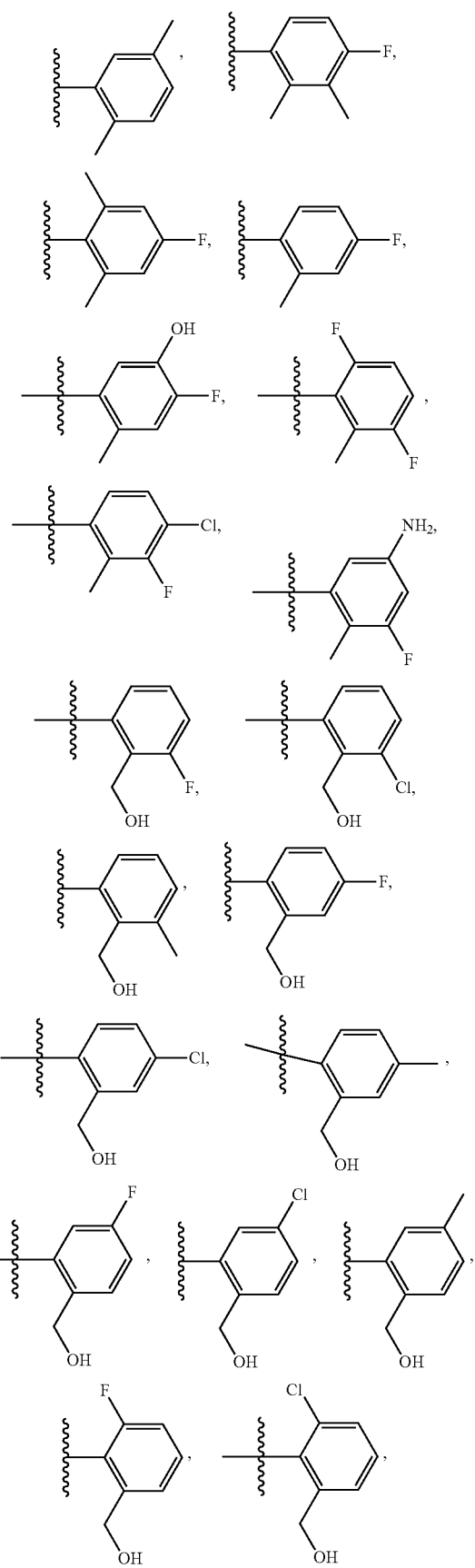

-continued
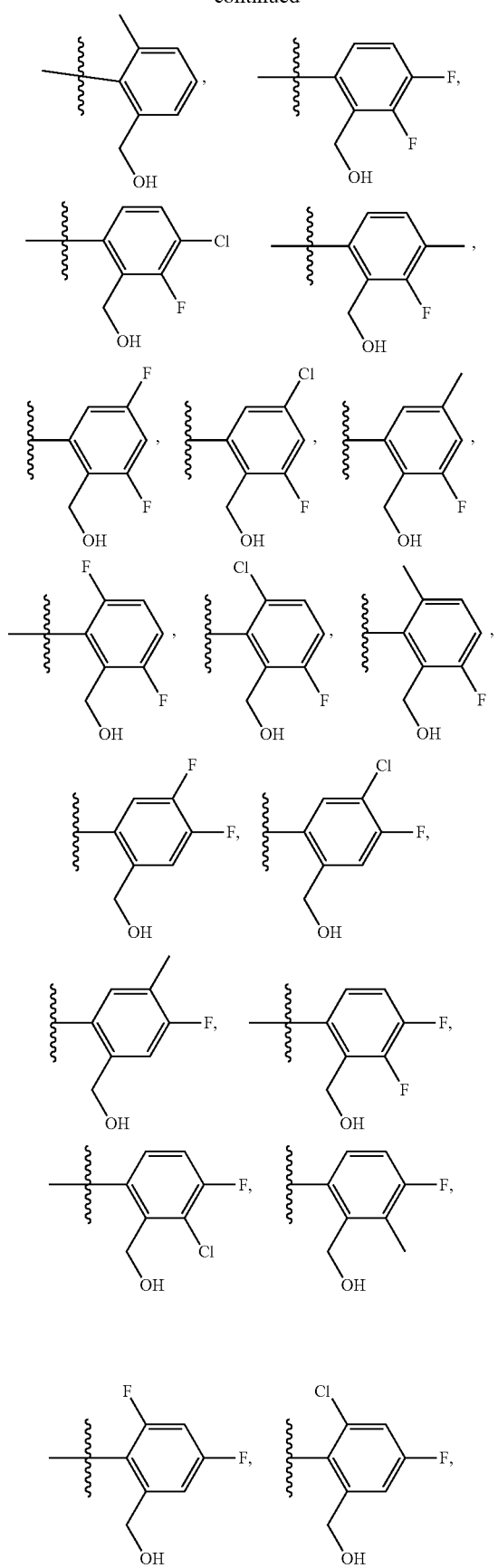
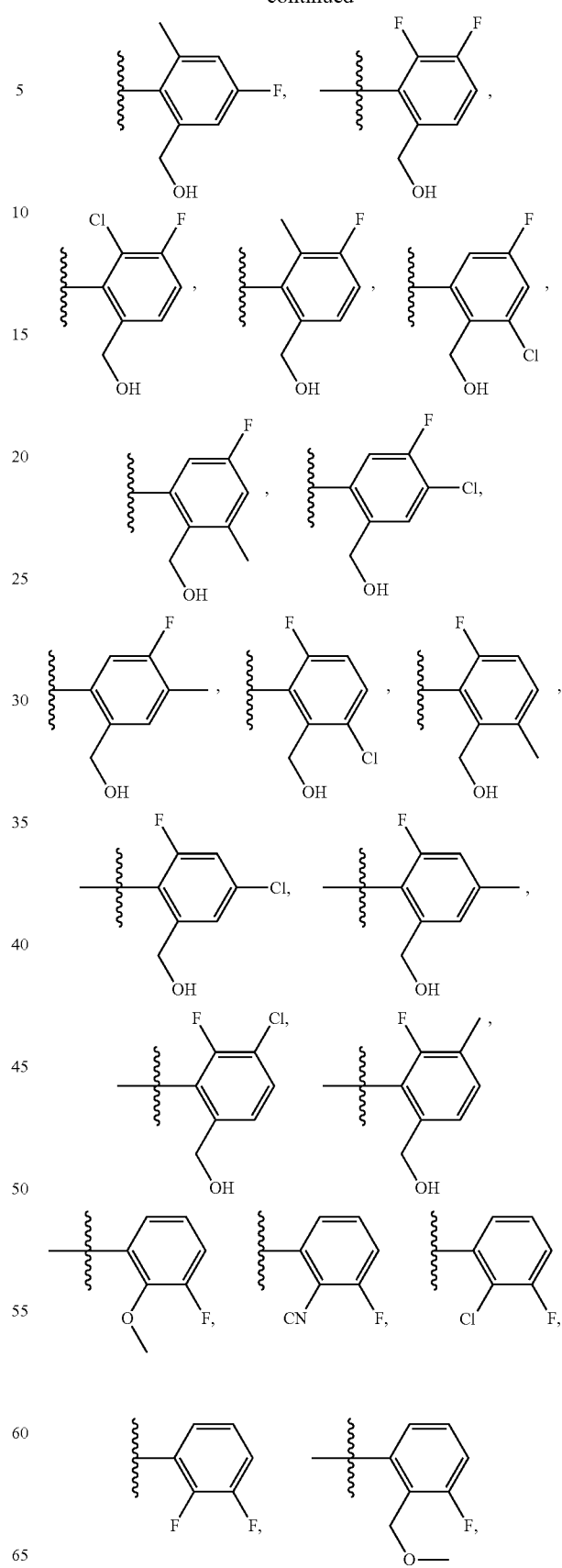

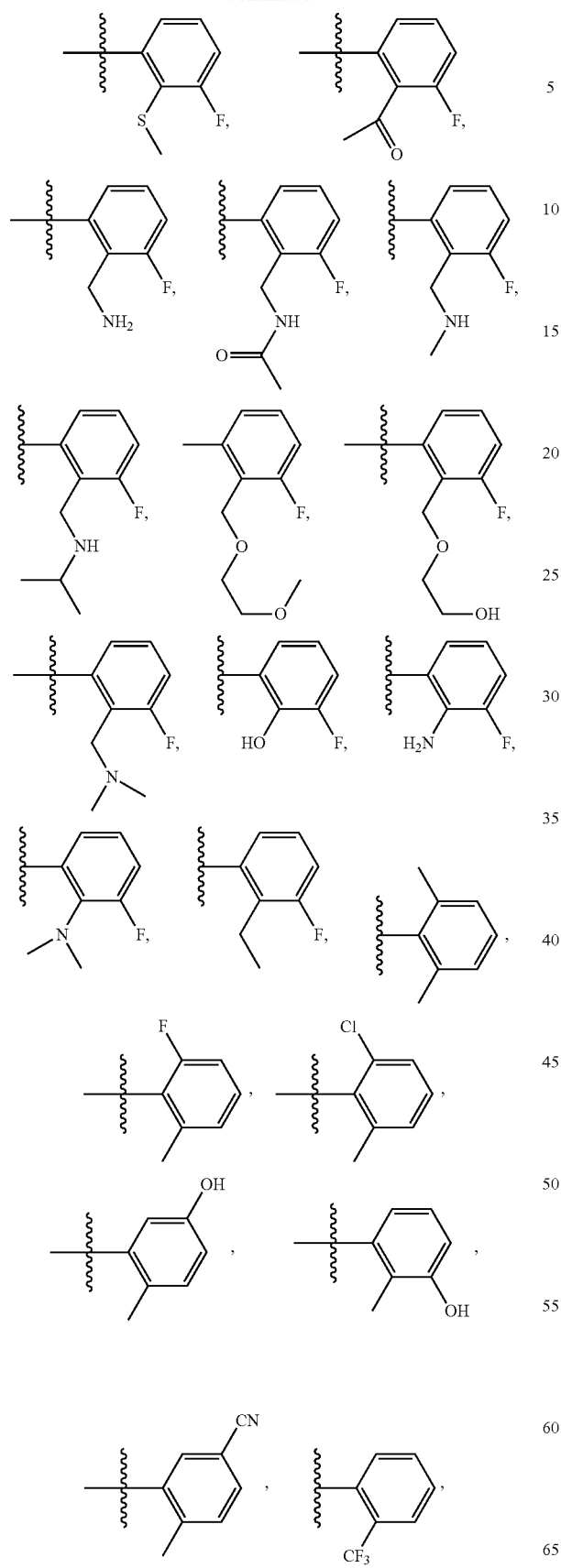
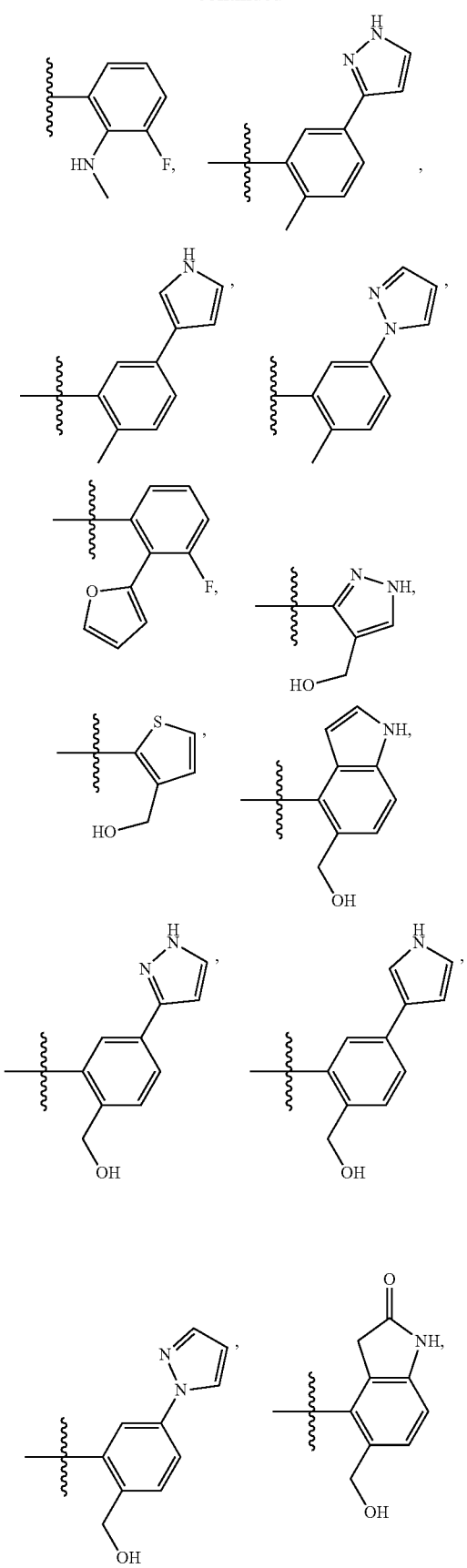

-continued
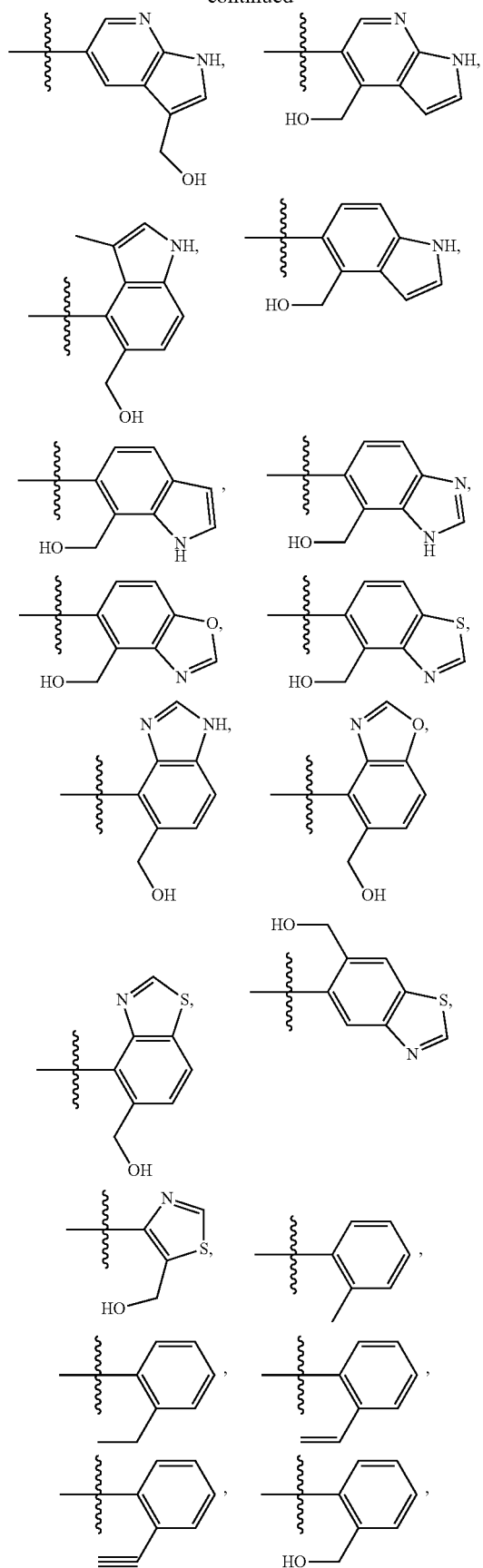
-continued
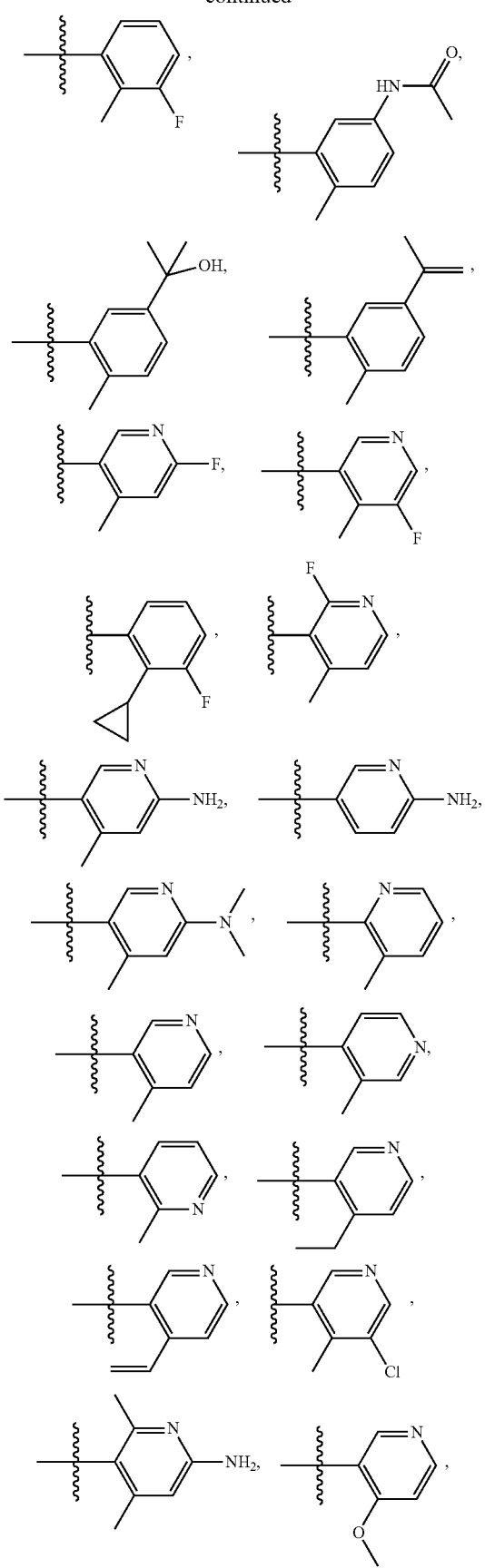

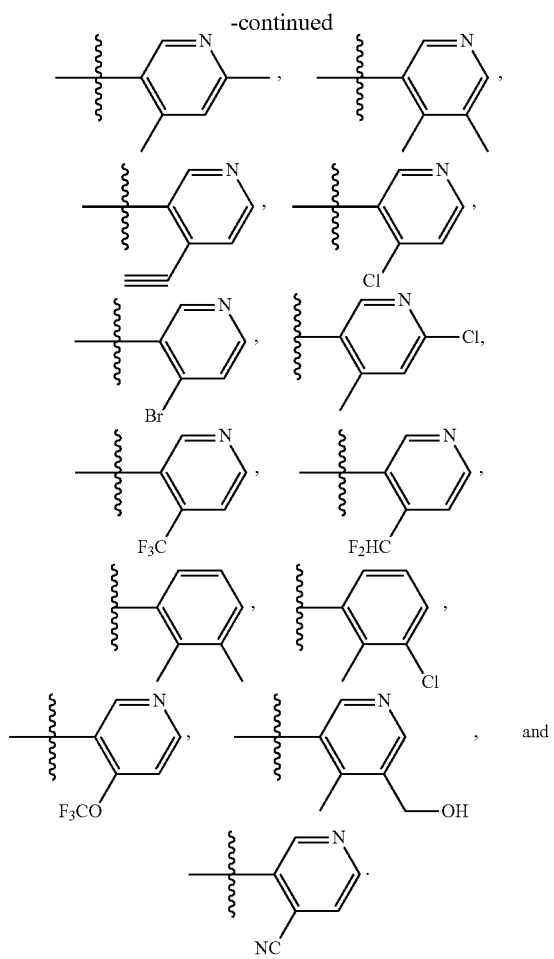

In some embodiments, $R^1$ is cyclopropyl, fluorocyclopropyl, difluorocyclopropyl, cyclobutyl, fluorocyclobutyl, or difluorocyclobutyl; $R^2$ and $R^3$ are independently —H, methyl, or fluoro; and $R^4$ is fluoro-methylphenyl, fluoro-hydroxymethylphenyl, chloro-methylphenyl, dimethylphenyl, acetamido-methylphenyl, hydroxyl-methylphenyl, methyl-propenylphenyl, ethynyl-methylphenyl, fluoro-methyl-methylaminophenyl, methyl-pyrrolylphenyl, methyl-thiazolylphenyl, cyano-methylphenyl, imidazolyl-methylphenyl, methylpyridinyl, chloro-methylpyridinyl, fluoro-methylpyridinyl, fluoromethyl-methylpyridinyl, bim-ethylpyridinyl, aminopyridinyl, amino-dimethylpyridinyl, methoxypyridinyl, acetyl-methylpyridinyl, hydroxymethylpyridinyl, hydroxymethyl-methylpyridinyl, hydroxyethyl-methylpyridinyl, cyanopyridinyl, trifluoromethylpyridinyl, methylthiophenyl, methylindolinyl, methylpyrimidinyl, dimethylpyrimidinyl, pyrazolyl, methylpyrazolyl, methylindolinyl, methyloxoindolinyl, pyrrolopyridinyl, methylpyrrolopyridinyl, methylpyrrolyl, pyrazolopyridinyl, dihydropyrrolopyridinyl, methylisothiazolyl, dimethylisothiazolyl, methylindazolyl, or methyl-bibenzothiazolyl.

The compounds described herein have c-abl inhibition activity and selectivity against c-abl. The compounds are effective to treat neurodegenerative diseases.

In an embodiment, $R^1$ is cyclopropyl, fluorocyclopropyl, cyclobutyl, fluorocyclobutyl, or difluorocyclobutyl; $R^2$ and $R^3$ are —H; $R^4$ is phenyl, pyridinyl, pyrazolyl, pyrrolo-pyridinyl, indolinyl, oxoindolinyl, benzothiazolyl, benzoimidazolyl, benzooxazolyl, or thiophenyl, wherein $R^4$ is optionally substituted with one or more groups selected from the group consisting of halo, hydroxyl, alkyl, haloalkyl, hydroxyalkyl, cycloalkyl, alkoxyalkyl, alkoxyalkoxy, alkylaminoalkyl, —$NR_aR_b$, —$NR_aC(=O)R_b$, —$OR_a$, —$SR_a$, —CN, —$C(=O)R_a$, —$C(=O)OR_a$, —$C(=O)NR_aR_b$, —$OC(=O)R_a$, furanyl, or pyrrolyl; $R_a$ and $R_b$ are independently —H, halo, amino, alkyl, or haloalkyl; and $R^5$ is —H, halo, or $C_1$-$C_3$ alkyl.

In various embodiments, $R^1$ is fluorocyclopropyl, and such compounds include, but are not limited to, the following compounds and salts thereof:

2-fluoro-N-(6-(3-fluoro-2-methylphenyl)imidazo[1,2-a]pyridin-2-yl)cyclopropane-1-carboxamide;
2-fluoro-N-(6-(2-fluoro-6-methylphenyl)imidazo[1,2-a]pyridin-2-yl)cyclopropane-1-carboxamide;
N-(3-chloro-6-(3-fluoro-2-methylphenyl)imidazo[1,2-a]pyridin-2-yl)-2-fluorocyclopropane-1-carboxamide;
N-(3-chloro-6-(2-fluoro-6-methylphenyl)imidazo[1,2-a]pyridin-2-yl)-2-fluorocyclopropane-1-carboxamide;
2-fluoro-N-(3-methyl-6-(4-methylpyridin-3-yl)imidazo[1,2-a]pyridin-2-yl)cyclopropane-1-carboxamide;
2-fluoro-N-(6-(4-methylpyridin-3-yl)imidazo[1,2-a]pyridin-2-yl)cyclopropane-1-carboxamide;
N-(3-chloro-6-(4-methylpyridin-3-yl)imidazo[1,2-a]pyridin-2-yl)-2-fluorocyclopropane-1-carboxamide;
2-fluoro-N-(6-(3-fluoro-2-methylphenyl)-3-methylimidazo[1,2-a]pyridin-2-yl)cyclopropane-1-carboxamide;
2-fluoro-N-(6-(2-fluoro-6-methylphenyl)-3-methylimidazo[1,2-a]pyridin-2-yl)cyclopropane-1-carboxamide;
2-fluoro-N-(6-(5-fluoro-4-methylpyridin-3-yl)-3-methyl-imidazo[1,2-a]pyridin-2-yl)cyclopropane-1-carboxamide;
2-fluoro-N-(6-(5-fluoro-2-methylphenyl)imidazo[1,2-a]pyridin-2-yl)cyclopropane-1-carboxamide;
2-fluoro-N-(6-(5-hydroxy-2-methylphenyl)imidazo[1,2-a]pyridin-2-yl)cyclopropane-1-carboxamide;
methyl 3-(2-(2-fluorocyclopropane-1-carboxamido)imidazo[1,2-a]pyridin-6-yl)-4-methylbenzoate;
2-fluoro-N-(6-(5-fluoro-4-methylpyridin-3-yl)imidazo[1,2-a]pyridin-2-yl)cyclopropane-1-carboxamide;
2-fluoro-N-(6-(5-methyl-1H-indol-4-yl)imidazo[1,2-a]pyridin-2-yl)cyclopropane-1-carboxamide;
N-(3-chloro-6-(5-fluoro-4-methylpyridin-3-yl)imidazo[1,2-a]pyridin-2-yl)-2-fluorocyclopropane-1-carboxamide;
N-(6-(5-cyano-2-methylphenyl)imidazo[1,2-a]pyridin-2-yl)-2-fluorocyclopropane-1-carboxamide;
N-(6-(1H-pyrazol-3-yl)imidazo[1,2-a]pyridin-2-yl)-2-fluorocyclopropane-1-carboxamide;
2-fluoro-N-(6-(4-methyl-1H-pyrazol-3-yl)imidazo[1,2-a]pyridin-2-yl)cyclopropane-1-carboxamide;
2-fluoro-N-(6-(3-hydroxy-2-methylphenyl)imidazo[1,2-a]pyridin-2-yl)cyclopropane-1-carboxamide;
N-(6-(4-chloropyridin-3-yl)imidazo[1,2-a]pyridin-2-yl)-2-fluorocyclopropane-1-carboxamide;
N-(6-(2,3-dimethylphenyl)imidazo[1,2-a]pyridin-2-yl)-2-fluorocyclopropane-1-carboxamide;
N-(6-(5-amino-2-methylphenyl)imidazo[1,2-a]pyridin-2-yl)-2-fluorocyclopropane-1-carboxamide;
2-fluoro-N-(6-(2-methyl-5-(methylamino)phenyl)imidazo[1,2-a]pyridin-2-yl)cyclopropane-1-carboxamide;
N-(6-(5-acetamido-2-methylphenyl)imidazo[1,2-a]pyridin-2-yl)-2-fluorocyclopropane-1-carboxamide;
N-(6-(5-chloro-2-methylphenyl)imidazo[1,2-a]pyridin-2-yl)-2-fluorocyclopropane-1-carboxamide;
N-(6-(1H-pyrrolo[2,3-b]pyridin-5-yl)imidazo[1,2-a]pyridin-2-yl)-2-fluorocyclopropane-1-carboxamide;

2-fluoro-N-(6-(2-methyl-5-(1H-pyrazol-3-yl)phenyl)imidazo[1,2-a]pyridin-2-yl)cyclopropane-1-carboxamide;
N-(6-(4-chloro-2-methylphenyl)imidazo[1,2-a]pyridin-2-yl)-2-fluorocyclopropane-1-carboxamide;
N-(6-(3-chloro-2-methylphenyl)imidazo[1,2-a]pyridin-2-yl)-2-fluorocyclopropane-1-carboxamide;
2-fluoro-N-(6-(4-(trifluoromethyl)pyridin-3-yl)imidazo[1,2-a]pyridin-2-yl)cyclopropane-1-carboxamide;
N-(6-(2,4-dimethylphenyl)imidazo[1,2-a]pyridin-2-yl)-2-fluorocyclopropane-1-carboxamide;
2-fluoro-N-(3-fluoro-6-(3-fluoro-2-methylphenyl)imidazo[1,2-a]pyridin-2-yl)cyclopropane-1-carboxamide;
N-(6-(2,5-dimethylphenyl)imidazo[1,2-a]pyridin-2-yl)-2-fluorocyclopropane-1-carboxamide;
2-fluoro-N-(6-(2-oxoindolin-6-yl)imidazo[1,2-a]pyridin-2-yl)cyclopropane-1-carboxamide;
N-(6-(4-cyanopyridin-3-yl)imidazo[1,2-a]pyridin-2-yl)-2-fluorocyclopropane-1-carboxamide;
2-fluoro-N-(6-(4-fluoro-2,3-dimethylphenyl)imidazo[1,2-a]pyridin-2-yl)cyclopropane-1-carboxamide;
2-fluoro-N-(6-(4-fluoro-2,6-dimethylphenyl)imidazo[1,2-a]pyridin-2-yl)cyclopropane-1-carboxamide;
2-fluoro-N-(6-(4-fluoro-2-methylphenyl)imidazo[1,2-a]pyridin-2-yl)cyclopropane-1-carboxamide;
2-fluoro-N-(6-(2-methyl-5-(1H-pyrrol-3-yl)phenyl)imidazo[1,2-a]pyridin-2-yl)cyclopropane-1-carboxamide;
2-fluoro-N-(6-(3-methylthiophen-2-yl)imidazo[1,2-a]pyridin-2-yl)cyclopropane-1-carboxamide;
N-(6-(2,6-dimethylphenyl)imidazo[1,2-a]pyridin-2-yl)-2-fluorocyclopropane-1-carboxamide;
2-fluoro-N-(6-(4-fluoro-5-hydroxy-2-methylphenyl)imidazo[1,2-a]pyridin-2-yl)cyclopropane-1-carboxamide;
N-(6-(3,4-difluoro-2-methylphenyl)imidazo[1,2-a]pyridin-2-yl)-2-fluorocyclopropane-1-carboxamide;
N-(6-(3,6-difluoro-2-methylphenyl)imidazo[1,2-a]pyridin-2-yl)-2-fluorocyclopropane-1-carboxamide;
N-(6-(4-chloro-3-fluoro-2-methylphenyl)imidazo[1,2-a]pyridin-2-yl)-2-fluorocyclopropane-1-carboxamide;
2-fluoro-N-(6-(2-fluoro-4-methylpyridin-3-yl)imidazo[1,2-a]pyridin-2-yl)cyclopropane-1-carboxamide;
2-fluoro-N-(6-(4-methoxypyridin-3-yl)imidazo[1,2-a]pyridin-2-yl)cyclopropane-1-carboxamide;
N-(6-(6-amino-4-methylpyridin-3-yl)imidazo[1,2-a]pyridin-2-yl)-2-fluorocyclopropane-1-carboxamide;
N-(6-(5-amino-3-fluoro-2-methylphenyl)imidazo[1,2-a]pyridin-2-yl)-2-fluorocyclopropane-1-carboxamide;
2-fluoro-N-(6-(5-methyl-2-oxoindolin-4-yl)imidazo[1,2-a]pyridin-2-yl)cyclopropane-1-carboxamide;
N-(6-(2-chloro-6-methylphenyl)imidazo[1,2-a]pyridin-2-yl)-2-fluorocyclopropane-1-carboxamide;
2-fluoro-N-(6-(3-methyl-1H-pyrrolo[2,3-b]pyridin-5-yl)imidazo[1,2-a]pyridin-2-yl)cyclopropane-1-carboxamide;
2-fluoro-N-(6-(2-oxo-2,3-dihydrobenzo[d]thiazol-5-yl)imidazo[1,2-a]pyridin-2-yl)cyclopropane-1-carboxamide;
N-(6-(6-aminopyridin-3-yl)imidazo[1,2-a]pyridin-2-yl)-2-fluorocyclopropane-1-carboxamide;
2-fluoro-N-(6-(2-methyl-5-(1H-pyrazol-1-yl)phenyl)imidazo[1,2-a]pyridin-2-yl)cyclopropane-1-carboxamide;
2-fluoro-N-(6-(3-fluoro-2-(hydroxymethyl)phenyl)imidazo[1,2-a]pyridin-2-yl)cyclopropane-1-carboxamide;
N-(3-bromo-6-(3-fluoro-2-methylphenyl)imidazo[1,2-a]pyridin-2-yl)-2-fluorocyclopropane-1-carboxamide;
2-fluoro-N-(6-(3-fluoro-2-methoxyphenyl)imidazo[1,2-a]pyridin-2-yl)cyclopropanecarboxamide;
N-(6-(2-cyano-3-fluorophenyl)imidazo[1,2-a]pyridin-2-yl)-2-fluorocyclopropanecarboxamide;
N-(6-(2-chloro-3-fluorophenyl)imidazo[1,2-a]pyridin-2-yl)-2-fluorocyclopropanecarboxamide;
N-(6-(2,3-difluorophenyl)imidazo[1,2-a]pyridin-2-yl)-2-fluorocyclopropanecarboxamide;
N-(6-(3,5-dimethyl-1H-indol-4-yl)imidazo[1,2-a]pyridin-2-yl)-2-fluorocyclopropanecarboxamide;
2-fluoro-N-(6-(3-fluoro-2-(methoxymethyl)phenyl)imidazo[1,2-a]pyridin-2-yl)cyclopropanecarboxamide;
2-fluoro-N-(6-(3-fluoro-2-(furan-2-yl)phenyl)imidazo[1,2-a]pyridin-2-yl)cyclopropanecarboxamide;
2-fluoro-N-(6-(3-fluoro-2-(methylthio)phenyl)imidazo[1,2-a]pyridin-2-yl)cyclopropanecarboxamide;
2-fluoro-N-(6-(6-fluoro-4-methylpyridin-3-yl)imidazo[1,2-a]pyridin-2-yl)cyclopropanecarboxamide;
N-(6-(2-acetyl-3-fluorophenyl)imidazo[1,2-a]pyridin-2-yl)-2-fluorocyclopropanecarboxamide;
N-(6-(6-(dimethylamino)-4-methylpyridin-3-yl)imidazo[1,2-a]pyridin-2-yl)-2-fluorocyclopropanecarboxamide;
N-(6-(3-fluoro-2-methylphenyl)imidazo[1,2-a]pyridin-2-yl)cyclopropanecarboxamide
2-fluoro-N-(6-(3-fluoro-2-methylphenyl)imidazo[1,2-a]pyridin-2-yl)cyclopropanecarboxamide;
2-fluoro-N-(6-(3-fluoro-2-methylphenyl)imidazo[1,2-a]pyridin-2-yl)cyclopropanecarboxamide;
2-fluoro-N-(6-(3-fluoro-2-methylphenyl)imidazo[1,2-a]pyridin-2-yl)cyclopropanecarboxamide;
N-(6-(2-(aminomethyl)-3-fluorophenyl)imidazo[1,2-a]pyridin-2-yl)-2-fluorocyclopropanecarboxamide;
N-(6-(2-(acetamidomethyl)-3-fluorophenyl)imidazo[1,2-a]pyridin-2-yl)-2-fluorocyclopropanecarboxamide;
2,2-difluoro-N-(6-(3-fluoro-2-methylphenyl)imidazo[1,2-a]pyridin-2-yl)cyclopropanecarboxamide;
2-fluoro-N-(6-(3-fluoro-2-((methylamino)methyl)phenyl)imidazo[1,2-a]pyridin-2-yl) cyclopropanecarboxamide;
2-fluoro-N-(6-(3-fluoro-2-((isopropylamino)methyl)phenyl)imidazo[1,2-a]pyridin-2-yl)cyclopropanecarboxamide;
2-fluoro-N-(6-(3-fluoro-2-((2-methoxyethoxy)methyl)phenyl)imidazo[1,2-a]pyridin-2-yl)cyclopropanecarboxamide;
2-fluoro-N-(6-(3-fluoro-2-((2-hydroxyethoxy)methyl)phenyl)imidazo[1,2-a]pyridin-2-yl)cyclopropanecarboxamide;
N-(6-(2-((dimethylamino)methyl)-3-fluorophenyl)imidazo[1,2-a]pyridin-2-yl)-2-fluorocyclopropanecarboxamide;
N-(6-(1H-pyrrolo[2,3-b]pyridin-5-yl)imidazo[1,2-a]pyridin-2-yl)-2-fluorocyclopropanecarboxamide;
2-fluoro-N-(6-(4-methyl-1H-pyrrolo[2,3-b]pyridin-5-yl)imidazo[1,2-a]pyridin-2-yl)cyclopropanecarboxamide;
N-(6-(4-chloro-1H-pyrrolo[2,3-b]pyridin-5-yl)imidazo[1,2-a]pyridin-2-yl)-2-fluorocyclopropanecarboxamide;
2-fluoro-N-(6-(o-tolyl)imidazo[1,2-a]pyridin-2-yl)cyclopropanecarboxamide;
2-fluoro-N-(6-(3-fluoro-2-hydroxyphenyl)imidazo[1,2-a]pyridin-2-yl)cyclopropanecarboxamide;
N-(6-(2-amino-3-fluorophenyl)imidazo[1,2-a]pyridin-2-yl)-2-fluorocyclopropanecarboxamide;
2-fluoro-N-(6-(5-methyl-1H-indol-6-yl)imidazo[1,2-a]pyridin-2-yl)cyclopropanecarboxamide;
2-fluoro-N-(6-(6-methyl-1H-indol-5-yl)imidazo[1,2-a]pyridin-2-yl)cyclopropanecarboxamide;
N-(6-(2-(dimethylamino)-3-fluorophenyl)imidazo[1,2-a]pyridin-2-yl)-2-fluorocyclopropanecarboxamide;
2-fluoro-N-(6-(5-methyl-1H-benzo[d]imidazol-6-yl)imidazo[1,2-a]pyridin-2-yl)cyclopropanecarboxamide;
N-(6-(2-ethyl-3-fluorophenyl)imidazo[1,2-a]pyridin-2-yl)-2-fluorocyclopropanecarboxamide;

2-fluoro-N-(6-(3-fluoro-2-(trifluoromethyl)phenyl)imidazo[1,2-a]pyridin-2-yl)cyclopropanecarboxamide;
N-(6-(2-cyclopropyl-3-fluorophenyl)imidazo[1,2-a]pyridin-2-yl)-2-fluorocyclopropanecarboxamide;
2-fluoro-N-(6-(3-fluoro-2-(methylamino)phenyl)imidazo[1,2-a]pyridin-2-yl)cyclopropanecarboxamide;
2-fluoro-N-(6-(5-methylbenzo[d]oxazol-6-yl)imidazo[1,2-a]pyridin-2-yl)cyclopropanecarboxamide;
2-fluoro-N-(6-(5-methyl-1H-benzo[d]imidazol-4-yl)imidazo[1,2-a]pyridin-2-yl)cyclopropane-1-carboxamide;
2-fluoro-N-(6-(6-methylbenzo[d]thiazol-5-yl)imidazo[1,2-a]pyridin-2-yl)cyclopropanecarboxamide;
2-fluoro-N-(6-(5-methylbenzo[d]oxazol-4-yl)imidazo[1,2-a]pyridin-2-yl)cyclopropanecarboxamide;
2-fluoro-N-(6-(5-methylbenzo[d]thiazol-6-yl)imidazo[1,2-a]pyridin-2-yl)cyclopropanecarboxamide;
2-fluoro-N-(6-(7-methylbenzo[d]thiazol-6-yl)imidazo[1,2-a]pyridin-2-yl)cyclopropanecarboxamide;
2-fluoro-N-(6-(3-fluoro-2-isopropylphenyl)imidazo[1,2-a]pyridin-2-yl)cyclopropanecarboxamide;
2-fluoro-N-(6-(2-methyl-3-(trifluoromethyl)phenyl)imidazo[1,2-a]pyridin-2-yl)cyclopropane-1-carboxamide;
2-fluoro-N-(6-(3-fluoro-2-(trifluoromethyl)phenyl)imidazo[1,2-a]pyridin-2-yl)cyclopropane-1-carboxamide;
2-fluoro-N-(6-(3-fluoro-2,6-dimethylphenyl)imidazo[1,2-a]pyridin-2-yl)cyclopropane-1-carboxamide;
N-(6-(2-ethyl-6-methylphenyl)imidazo[1,2-a]pyridin-2-yl)-2-fluorocyclopropane-1-carboxamide
N-(6-(4-acetyl-2-methylphenyl)imidazo[1,2-a]pyridin-2-yl)-2-fluorocyclopropane-1-carboxamide;
N-(6-(2-chloro-3,4-difluorophenyl)imidazo[1,2-a]pyridin-2-yl)-2-fluorocyclopropane-1-carboxamide;
N-(6-(2-chloro-3,6-difluorophenyl)imidazo[1,2-a]pyridin-2-yl)-2-fluorocyclopropane-1-carboxamide;
2-fluoro-N-(6-(furan-2-yl)imidazo[1,2-a]pyridin-2-yl)cyclopropane-1-carboxamide;
2-fluoro-N-(6-(thiophen-2-yl)imidazo[1,2-a]pyridin-2-yl)cyclopropane-1-carboxamide;
2-fluoro-N-(6-(thiazol-5-yl)imidazo[1,2-a]pyridin-2-yl)cyclopropane-1-carboxamide;
2-fluoro-N-(6-(3-methylisothiazol-5-yl)imidazo[1,2-a]pyridin-2-yl)cyclopropane-1-carboxamide;
2-fluoro-N-(6-(5-methylthiazol-4-yl)imidazo[1,2-a]pyridin-2-yl)cyclopropane-1-carboxamide;
2-fluoro-N-(6-(3-fluoro-2-methylphenyl)-8-(trifluoromethyl)imidazo[1,2-a]pyridin-2-yl)cyclopropane-1-carboxamide;
N-(8-(difluoromethyl)-6-(3-fluoro-2-methylphenyl)imidazo[1,2-a]pyridin-2-yl)-2-fluorocyclopropane-1-carboxamide;
2-fluoro-N-(6-(3-fluoro-2-methylphenyl)-8-(fluoromethyl)imidazo[1,2-a]pyridin-2-yl)cyclopropane-1-carboxamide;
2-fluoro-N-(8-fluoro-6-(3-fluoro-2-methylphenyl)imidazo[1,2-a]pyridin-2-yl)cyclopropane-1-carboxamide;
2-fluoro-N-(7-fluoro-6-(3-fluoro-2-methylphenyl)imidazo[1,2-a]pyridin-2-yl)cyclopropane-1-carboxamide;
2-fluoro-N-(6-(4-fluoro-2-methylphenyl)-8-(trifluoromethyl)imidazo[1,2-a]pyridin-2-yl)cyclopropane-1-carboxamide;
N-(8-(difluoromethyl)-6-(4-fluoro-2-methylphenyl)imidazo[1,2-a]pyridin-2-yl)-2-fluorocyclopropane-1-carboxamide;
2-fluoro-N-(6-(4-fluoro-2-methylphenyl)-8-(fluoromethyl)imidazo[1,2-a]pyridin-2-yl)cyclopropane-1-carboxamide;
2-fluoro-N-(8-fluoro-6-(4-fluoro-2-methylphenyl)imidazo[1,2-a]pyridin-2-yl)cyclopropane-1-carboxamide;
2-fluoro-N-(7-fluoro-6-(4-fluoro-2-methylphenyl)imidazo[1,2-a]pyridin-2-yl)cyclopropane-1-carboxamide;
2-fluoro-N-(6-(5-fluoro-2-methylphenyl)-8-(trifluoromethyl)imidazo[1,2-a]pyridin-2-yl)cyclopropane-1-carboxamide;
N-(8-(difluoromethyl)-6-(5-fluoro-2-methylphenyl)imidazo[1,2-a]pyridin-2-yl)-2-fluorocyclopropane-1-carboxamide;
2-fluoro-N-(6-(5-fluoro-2-methylphenyl)-8-(fluoromethyl)imidazo[1,2-a]pyridin-2-yl)cyclopropane-1-carboxamide;
2-fluoro-N-(8-fluoro-6-(5-fluoro-2-methylphenyl)imidazo[1,2-a]pyridin-2-yl)cyclopropane-1-carboxamide;
2-fluoro-N-(7-fluoro-6-(5-fluoro-2-methylphenyl)imidazo[1,2-a]pyridin-2-yl)cyclopropane-1-carboxamide;
2-fluoro-N-(6-(2-fluoro-6-methylphenyl)-8-(trifluoromethyl)imidazo[1,2-a]pyridin-2-yl)cyclopropane-1-carboxamide;
N-(8-(difluoromethyl)-6-(2-fluoro-6-methylphenyl)imidazo[1,2-a]pyridin-2-yl)-2-fluorocyclopropane-1-carboxamide;
2-fluoro-N-(6-(2-fluoro-6-methylphenyl)-8-(fluoromethyl)imidazo[1,2-a]pyridin-2-yl)cyclopropane-1-carboxamide;
2-fluoro-N-(8-fluoro-6-(2-fluoro-6-methylphenyl)imidazo[1,2-a]pyridin-2-yl)cyclopropane-1-carboxamide;
2-fluoro-N-(7-fluoro-6-(2-fluoro-6-methylphenyl)imidazo[1,2-a]pyridin-2-yl)cyclopropane-1-carboxamide;
N-(6-(3-fluoro-2-(hydroxymethyl)phenyl)imidazo[1,2-a]pyridin-2-yl)cyclopropanecarboxamide;
N-(6-(4-fluoro-2-(hydroxymethyl)phenyl)imidazo[1,2-a]pyridin-2-yl)cyclopropanecarboxamide;
2-fluoro-N-(6-(4-fluoro-2-(hydroxymethyl)phenyl)imidazo[1,2-a]pyridin-2-yl)cyclopropane-1-carboxamide;
N-(6-(5-fluoro-2-(hydroxymethyl)phenyl)imidazo[1,2-a]pyridin-2-yl)cyclopropanecarboxamide;
2-fluoro-N-(6-(5-fluoro-2-(hydroxymethyl)phenyl)imidazo[1,2-a]pyridin-2-yl)cyclopropane-1-carboxamide;
N-(6-(2-fluoro-6-(hydroxymethyl)phenyl)imidazo[1,2-a]pyridin-2-yl)cyclopropanecarboxamide;
2-fluoro-N-(6-(2-fluoro-6-(hydroxymethyl)phenyl)imidazo[1,2-a]pyridin-2-yl)cyclopropane-1-carboxamide;
N-(6-(3-chloro-2-(hydroxymethyl)phenyl)imidazo[1,2-a]pyridin-2-yl)cyclopropanecarboxamide;
N-(6-(3-chloro-2-(hydroxymethyl)phenyl)imidazo[1,2-a]pyridin-2-yl)-2-fluorocyclopropane-1-carboxamide;
N-(6-(4-chloro-2-(hydroxymethyl)phenyl)imidazo[1,2-a]pyridin-2-yl)cyclopropanecarboxamide;
N-(6-(4-chloro-2-(hydroxymethyl)phenyl)imidazo[1,2-a]pyridin-2-yl)-2-fluorocyclopropane-1-carboxamide;
N-(6-(5-chloro-2-(hydroxymethyl)phenyl)imidazo[1,2-a]pyridin-2-yl)cyclopropanecarboxamide;
N-(6-(5-chloro-2-(hydroxymethyl)phenyl)imidazo[1,2-a]pyridin-2-yl)-2-fluorocyclopropane-1-carboxamide;
N-(6-(2-chloro-6-(hydroxymethyl)phenyl)imidazo[1,2-a]pyridin-2-yl)cyclopropanecarboxamide;
N-(6-(2-chloro-6-(hydroxymethyl)phenyl)imidazo[1,2-a]pyridin-2-yl)-2-fluorocyclopropane-1-carboxamide;
N-(6-(2-(hydroxymethyl)-3-methylphenyl)imidazo[1,2-a]pyridin-2-yl)cyclopropanecarboxamide;
2-fluoro-N-(6-(2-(hydroxymethyl)-3-methylphenyl)imidazo[1,2-a]pyridin-2-yl)cyclopropane-1-carboxamide;
N-(6-(2-(hydroxymethyl)-4-methylphenyl)imidazo[1,2-a]pyridin-2-yl)cyclopropanecarboxamide;

2-fluoro-N-(6-(2-(hydroxymethyl)-4-methylphenyl)imidazo[1,2-a]pyridin-2-yl)cyclopropane-1-carboxamide;
N-(6-(2-(hydroxymethyl)-5-methylphenyl)imidazo[1,2-a]pyridin-2-yl)cyclopropanecarboxamide;
2-fluoro-N-(6-(2-(hydroxymethyl)-5-methylphenyl)imidazo[1,2-a]pyridin-2-yl)cyclopropane-1-carboxamide;
N-(6-(2-(hydroxymethyl)-6-methylphenyl)imidazo[1,2-a]pyridin-2-yl)cyclopropanecarboxamide;
2-fluoro-N-(6-(2-(hydroxymethyl)-6-methylphenyl)imidazo[1,2-a]pyridin-2-yl)cyclopropane-1-carboxamide;
N-(6-(3,4-difluoro-2-(hydroxymethyl)phenyl)imidazo[1,2-a]pyridin-2-yl)cyclopropanecarboxamide;
N-(6-(3,4-difluoro-2-(hydroxymethyl)phenyl)imidazo[1,2-a]pyridin-2-yl)-2-fluorocyclopropane-1-carboxamide;
N-(6-(4,5-difluoro-2-(hydroxymethyl)phenyl)imidazo[1,2-a]pyridin-2-yl)cyclopropanecarboxamide;
N-(6-(4,5-difluoro-2-(hydroxymethyl)phenyl)imidazo[1,2-a]pyridin-2-yl)-2-fluorocyclopropane-1-carboxamide;
N-(6-(2,3-difluoro-6-(hydroxymethyl)phenyl)imidazo[1,2-a]pyridin-2-yl)cyclopropanecarboxamide;
N-(6-(2,3-difluoro-6-(hydroxymethyl)phenyl)imidazo[1,2-a]pyridin-2-yl)-2-fluorocyclopropane-1-carboxamide;
N-(6-(3,6-difluoro-2-(hydroxymethyl)phenyl)imidazo[1,2-a]pyridin-2-yl)cyclopropanecarboxamide;
N-(6-(3,6-difluoro-2-(hydroxymethyl)phenyl)imidazo[1,2-a]pyridin-2-yl)-2-fluorocyclopropane-1-carboxamide;
N-(6-(3-chloro-4-fluoro-2-(hydroxymethyl)phenyl)imidazo[1,2-a]pyridin-2-yl)cyclopropanecarboxamide;
N-(6-(3-chloro-4-fluoro-2-(hydroxymethyl)phenyl)imidazo[1,2-a]pyridin-2-yl)-2-fluorocyclopropane-1-carboxamide;
N-(6-(4-chloro-5-fluoro-2-(hydroxymethyl)phenyl)imidazo[1,2-a]pyridin-2-yl)cyclopropanecarboxamide;
N-(6-(4-chloro-5-fluoro-2-(hydroxymethyl)phenyl)imidazo[1,2-a]pyridin-2-yl)-2-fluorocyclopropane-1-carboxamide;
N-(6-(3-chloro-2-fluoro-6-(hydroxymethyl)phenyl)imidazo[1,2-a]pyridin-2-yl)cyclopropanecarboxamide;
N-(6-(3-chloro-2-fluoro-6-(hydroxymethyl)phenyl)imidazo[1,2-a]pyridin-2-yl)-2-fluorocyclopropane-1-carboxamide;
N-(6-(6-chloro-3-fluoro-2-(hydroxymethyl)phenyl)imidazo[1,2-a]pyridin-2-yl)cyclopropanecarboxamide;
N-(6-(6-chloro-3-fluoro-2-(hydroxymethyl)phenyl)imidazo[1,2-a]pyridin-2-yl)-2-fluorocyclopropane-1-carboxamide;
N-(6-(4-fluoro-2-(hydroxymethyl)-3-methylphenyl)imidazo[1,2-a]pyridin-2-yl)cyclopropanecarboxamide;
2-fluoro-N-(6-(4-fluoro-2-(hydroxymethyl)-3-methylphenyl)imidazo[1,2-a]pyridin-2-yl)cyclopropane-1-carboxamide;
N-(6-(5-fluoro-2-(hydroxymethyl)-4-methylphenyl)imidazo[1,2-a]pyridin-2-yl)cyclopropanecarboxamide;
2-fluoro-N-(6-(5-fluoro-2-(hydroxymethyl)-4-methylphenyl)imidazo[1,2-a]pyridin-2-yl)cyclopropane-1-carboxamide;
N-(6-(2-fluoro-6-(hydroxymethyl)-3-methylphenyl)imidazo[1,2-a]pyridin-2-yl)cyclopropanecarboxamide;
2-fluoro-N-(6-(2-fluoro-6-(hydroxymethyl)-3-methylphenyl)imidazo[1,2-a]pyridin-2-yl)cyclopropane-1-carboxamide;
N-(6-(3-fluoro-2-(hydroxymethyl)-6-methylphenyl)imidazo[1,2-a]pyridin-2-yl)cyclopropanecarboxamide;
2-fluoro-N-(6-(3-fluoro-2-(hydroxymethyl)-6-methylphenyl)imidazo[1,2-a]pyridin-2-yl)cyclopropane-1-carboxamide;
N-(6-(4-chloro-3-fluoro-2-(hydroxymethyl)phenyl)imidazo[1,2-a]pyridin-2-yl)cyclopropanecarboxamide;
N-(6-(4-chloro-3-fluoro-2-(hydroxymethyl)phenyl)imidazo[1,2-a]pyridin-2-yl)-2-fluorocyclopropane-1-carboxamide;
N-(6-(3-fluoro-2-(hydroxymethyl)-4-methylphenyl)imidazo[1,2-a]pyridin-2-yl)cyclopropanecarboxamide;
2-fluoro-N-(6-(3-fluoro-2-(hydroxymethyl)-4-methylphenyl)imidazo[1,2-a]pyridin-2-yl)cyclopropane-1-carboxamide;
N-(6-(3,5-difluoro-2-(hydroxymethyl)phenyl)imidazo[1,2-a]pyridin-2-yl)cyclopropanecarboxamide;
N-(6-(3,5-difluoro-2-(hydroxymethyl)phenyl)imidazo[1,2-a]pyridin-2-yl)-2-fluorocyclopropane-1-carboxamide;
N-(6-(5-chloro-3-fluoro-2-(hydroxymethyl)phenyl)imidazo[1,2-a]pyridin-2-yl)cyclopropanecarboxamide;
N-(6-(5-chloro-3-fluoro-2-(hydroxymethyl)phenyl)imidazo[1,2-a]pyridin-2-yl)-2-fluorocyclopropane-1-carboxamide;
N-(6-(3-fluoro-2-(hydroxymethyl)-5-methylphenyl)imidazo[1,2-a]pyridin-2-yl)cyclopropanecarboxamide;
2-fluoro-N-(6-(3-fluoro-2-(hydroxymethyl)-5-methylphenyl)imidazo[1,2-a]pyridin-2-yl)cyclopropane-1-carboxamide;
N-(6-(5-chloro-4-fluoro-2-(hydroxymethyl)phenyl)imidazo[1,2-a]pyridin-2-yl)cyclopropanecarboxamide;
N-(6-(5-chloro-4-fluoro-2-(hydroxymethyl)phenyl)imidazo[1,2-a]pyridin-2-yl)-2-fluorocyclopropane-1-carboxamide;
N-(6-(3,4-difluoro-2-(hydroxymethyl)phenyl)imidazo[1,2-a]pyridin-2-yl)cyclopropanecarboxamide;
N-(6-(3,4-difluoro-2-(hydroxymethyl)phenyl)imidazo[1,2-a]pyridin-2-yl)-2-fluorocyclopropane-1-carboxamide;
N-(6-(2,4-difluoro-6-(hydroxymethyl)phenyl)imidazo[1,2-a]pyridin-2-yl)cyclopropanecarboxamide;
N-(6-(2,4-difluoro-6-(hydroxymethyl)phenyl)imidazo[1,2-a]pyridin-2-yl)-2-fluorocyclopropane-1-carboxamide;
N-(6-(2-chloro-4-fluoro-6-(hydroxymethyl)phenyl)imidazo[1,2-a]pyridin-2-yl)cyclopropanecarboxamide;
N-(6-(2-chloro-4-fluoro-6-(hydroxymethyl)phenyl)imidazo[1,2-a]pyridin-2-yl)-2-fluorocyclopropane-1-carboxamide;
N-(6-(4-fluoro-2-(hydroxymethyl)-6-methylphenyl)imidazo[1,2-a]pyridin-2-yl)cyclopropanecarboxamide;
2-fluoro-N-(6-(4-fluoro-2-(hydroxymethyl)-6-methylphenyl)imidazo[1,2-a]pyridin-2-yl)cyclopropane-1-carboxamide;
N-(6-(2-chloro-3-fluoro-6-(hydroxymethyl)phenyl)imidazo[1,2-a]pyridin-2-yl)cyclopropanecarboxamide;
N-(6-(2-chloro-3-fluoro-6-(hydroxymethyl)phenyl)imidazo[1,2-a]pyridin-2-yl)-2-fluorocyclopropane-1-carboxamide;
N-(6-(3,5-difluoro-2-(hydroxymethyl)-6-methylphenyl)imidazo[1,2-a]pyridin-2-yl)cyclopropanecarboxamide;
N-(6-(3,5-difluoro-2-(hydroxymethyl)-6-methylphenyl)imidazo[1,2-a]pyridin-2-yl)-2-fluorocyclopropane-1-carboxamide;
N-(6-(3-chloro-5-fluoro-2-(hydroxymethyl)phenyl)imidazo[1,2-a]pyridin-2-yl)cyclopropanecarboxamide;
N-(6-(3-chloro-5-fluoro-2-(hydroxymethyl)phenyl)imidazo[1,2-a]pyridin-2-yl)-2-fluorocyclopropane-1-carboxamide;
N-(6-(5-fluoro-2-(hydroxymethyl)-3-methylphenyl)imidazo[1,2-a]pyridin-2-yl)cyclopropanecarboxamide;
2-fluoro-N-(6-(5-fluoro-2-(hydroxymethyl)-3-methylphenyl)imidazo[1,2-a]pyridin-2-yl)cyclopropane-1-carboxamide;

N-(6-(5-fluoro-2-(hydroxymethyl)-4-methylphenyl)imidazo [1,2-a]pyridin-2-yl)cyclopropanecarboxamide;
2-fluoro-N-(6-(5-fluoro-2-(hydroxymethyl)-4-methylphenyl)imidazo[1,2-a]pyridin-2-yl)cyclopropane-1-carboxamide;
N-(6-(3-chloro-6-fluoro-2-(hydroxymethyl)phenyl)imidazo [1,2-a]pyridin-2-yl)cyclopropanecarboxamide;
N-(6-(3-chloro-6-fluoro-2-(hydroxymethyl)phenyl)imidazo [1,2-a]pyridin-2-yl)-2-fluorocyclopropane-1-carboxamide;
N-(6-(6-fluoro-2-(hydroxymethyl)-3-methylphenyl)imidazo [1,2-a]pyridin-2-yl)cyclopropanecarboxamide;
2-fluoro-N-(6-(6-fluoro-2-(hydroxymethyl)-3-methylphenyl)imidazo[1,2-a]pyridin-2-yl)cyclopropane-1-carboxamide;
N-(6-(4-chloro-2-fluoro-6-(hydroxymethyl)phenyl)imidazo [1,2-a]pyridin-2-yl)cyclopropanecarboxamide;
N-(6-(4-chloro-2-fluoro-6-(hydroxymethyl)phenyl)imidazo [1,2-a]pyridin-2-yl)-2-fluorocyclopropane-1-carboxamide;
N-(6-(2-fluoro-6-(hydroxymethyl)-4-methylphenyl)imidazo [1,2-a]pyridin-2-yl)cyclopropanecarboxamide;
2-fluoro-N-(6-(2-fluoro-6-(hydroxymethyl)-4-methylphenyl)imidazo[1,2-a]pyridin-2-yl)cyclopropane-1-carboxamide;
N-(6-(5-(hydroxymethyl)-1H-indol-4-yl)imidazo[1,2-a] pyridin-2-yl)cyclopropanecarboxamide;
2-fluoro-N-(6-(5-(hydroxymethyl)-1H-indol-4-yl)imidazo [1,2-a]pyridin-2-yl)cyclopropane-1-carboxamide;
N-(6-(4-(hydroxymethyl)-1H-pyrazol-3-yl)imidazo[1,2-a] pyridin-2-yl)cyclopropanecarboxamide;
2-fluoro-N-(6-(4-(hydroxymethyl)-1H-pyrazol-3-yl)imidazo[1,2-a]pyridin-2-yl)cyclopropane-1-carboxamide;
N-(6-(2-(hydroxymethyl)-5-(1H-pyrazol-3-yl)phenyl)imidazo[1,2-a]pyridin-2-yl)cyclopropanecarboxamide;
2-fluoro-N-(6-(2-(hydroxymethyl)-5-(1H-pyrazol-3-yl)phenyl)imidazo[1,2-a]pyridin-2-yl)cyclopropane-1-carboxamide;
N-(6-(2-(hydroxymethyl)-5-(1H-pyrrol-3-yl)phenyl)imidazo[1,2-a]pyridin-2-yl)cyclopropanecarboxamide;
2-fluoro-N-(6-(2-(hydroxymethyl)-5-(1H-pyrrol-3-yl)phenyl)imidazo[1,2-a]pyridin-2-yl)cyclopropane-1-carboxamide;
N-(6-(3-(hydroxymethyl)thiophen-2-yl)imidazo[1,2-a]pyridin-2-yl)cyclopropanecarboxamide;
2-fluoro-N-(6-(3-(hydroxymethyl)thiophen-2-yl)imidazo[1, 2-a]pyridin-2-yl)cyclopropane-1-carboxamide;
N-(6-(5-(hydroxymethyl)-2-oxoindolin-4-yl)imidazo[1,2-a] pyridin-2-yl)cyclopropanecarboxamide;
2-fluoro-N-(6-(5-(hydroxymethyl)-2-oxoindolin-4-yl)imidazo[1,2-a]pyridin-2-yl)cyclopropane-1-carboxamide;
N-(6-(3-(hydroxymethyl)-1H-pyrrolo[2,3-b]pyridin-5-yl) imidazo[1,2-a]pyridin-2-yl)cyclopropanecarboxamide;
2-fluoro-N-(6-(3-(hydroxymethyl)-1H-pyrrolo[2,3-b]pyridin-5-yl)imidazo[1,2-a]pyridin-2-yl)cyclopropane-1-carboxamide;
N-(6-(2-(hydroxymethyl)-5-(1H-pyrazol-1-yl)phenyl)imidazo[1,2-a]pyridin-2-yl)cyclopropanecarboxamide;
2-fluoro-N-(6-(2-(hydroxymethyl)-5-(1H-pyrazol-1-yl)phenyl)imidazo[1,2-a]pyridin-2-yl)cyclopropane-1-carboxamide;
N-(6-(5-(hydroxymethyl)-3-methyl-1H-indol-4-yl)imidazo [1,2-a]pyridin-2-yl)cyclopropanecarboxamide;
2-fluoro-N-(6-(5-(hydroxymethyl)-3-methyl-1H-indol-4-yl) imidazo[1,2-a]pyridin-2-yl)cyclopropane-1-carboxamide;
N-(6-(4-(hydroxymethyl)-1H-pyrrolo[2,3-b]pyridin-5-yl) imidazo[1,2-a]pyridin-2-yl)cyclopropanecarboxamide;
2-fluoro-N-(6-(4-(hydroxymethyl)-1H-pyrrolo[2,3-b]pyridin-5-yl)imidazo[1,2-a]pyridin-2-yl)cyclopropane-1-carboxamide;
N-(6-(5-(hydroxymethyl)-1H-indol-6-yl)imidazo[1,2-a]pyridin-2-yl)cyclopropanecarboxamide;
2-fluoro-N-(6-(5-(hydroxymethyl)-1H-indol-6-yl)imidazo [1,2-a]pyridin-2-yl)cyclopropane-1-carboxamide;
N-(6-(6-(hydroxymethyl)-1H-indol-5-yl)imidazo[1,2-a]pyridin-2-yl)cyclopropanecarboxamide;
2-fluoro-N-(6-(6-(hydroxymethyl)-1H-indol-5-yl)imidazo [1,2-a]pyridin-2-yl)cyclopropane-1-carboxamide;
N-(6-(5-(hydroxymethyl)-1H-benzo[d]imidazol-6-yl)imidazo[1,2-a]pyridin-2-yl)cyclopropanecarboxamide;
2-fluoro-N-(6-(5-(hydroxymethyl)-1H-benzo[d]imidazol-6-yl)imidazo[1,2-a]pyridin-2-yl)cyclopropane-1-carboxamide;
N-(6-(5-(hydroxymethyl)benzo[d]oxazol-6-yl)imidazo[1,2-a]pyridin-2-yl)cyclopropanecarboxamide;
2-fluoro-N-(6-(5-(hydroxymethyl)benzo[d]oxazol-6-yl)imidazo[1,2-a]pyridin-2-yl)cyclopropane-1-carboxamide;
N-(6-(5-(hydroxymethyl)-1H-benzo[d]imidazol-4-yl)imidazo[1,2-a]pyridin-2-yl)cyclopropanecarboxamide;
2-fluoro-N-(6-(5-(hydroxymethyl)-1H-benzo[d]imidazol-4-yl)imidazo[1,2-a]pyridin-2-yl)cyclopropane-1-carboxamide;
N-(6-(5-(hydroxymethyl)benzo[d]thiazol-4-yl)imidazo[1,2-a]pyridin-2-yl)cyclopropanecarboxamide;
2-fluoro-N-(6-(5-(hydroxymethyl)benzo[d]thiazol-4-yl)imidazo[1,2-a]pyridin-2-yl)cyclopropane-1-carboxamide;
N-(6-(5-(hydroxymethyl)benzo[d]oxazol-4-yl)imidazo[1,2-a]pyridin-2-yl)cyclopropanecarboxamide;
2-fluoro-N-(6-(5-(hydroxymethyl)benzo[d]oxazol-4-yl)imidazo[1,2-a]pyridin-2-yl)cyclopropane-1-carboxamide;
N-(6-(5-(hydroxymethyl)benzo[d]thiazol-6-yl)imidazo[1,2-a]pyridin-2-yl)cyclopropanecarboxamide;
2-fluoro-N-(6-(5-(hydroxymethyl)benzo[d]thiazol-6-yl)imidazo[1,2-a]pyridin-2-yl)cyclopropane-1-carboxamide;
N-(6-(7-(hydroxymethyl)benzo[d]thiazol-6-yl)imidazo[1,2-a]pyridin-2-yl)cyclopropanecarboxamide;
2-fluoro-N-(6-(7-(hydroxymethyl)benzo[d]thiazol-6-yl)imidazo[1,2-a]pyridin-2-yl)cyclopropane-1-carboxamide;
N-(6-(5-(hydroxymethyl)thiazol-4-yl)imidazo[1,2-a]pyridin-2-yl)cyclopropanecarboxamide; and
2-fluoro-N-(6-(5-(hydroxymethyl)thiazol-4-yl)imidazo[1,2-a]pyridin-2-yl)cyclopropane-1-carboxamide.

In an embodiment, $R^1$ is fluorocyclopropyl; $R^2$ and $R^3$ are —H; $R^4$ is phenyl, indolinyl, oxoindolinyl, or benzothiazolyl, wherein $R^4$ is optionally substituted with one or more groups selected from the group consisting of halo, hydroxyl, alkyl, alkylamino, and pyrrolyl; and $R^5$ is —H, halo, or $C_1$-$C_3$ alkyl. In various embodiments, such compounds include, but are not limited to, the following compounds and salts thereof:

2-fluoro-N-(6-(3-fluoro-2-methylphenyl)imidazo[1,2-a] pyridin-2-yl)cyclopropane-1-carboxamide;
2-fluoro-N-(6-(2-fluoro-6-methylphenyl)imidazo[1,2-a] pyridin-2-yl)cyclopropane-1-carboxamide;
N-(3-chloro-6-(3-fluoro-2-methylphenyl)imidazo[1,2-a] pyridin-2-yl)-2-fluorocyclopropane-1-carboxamide;
N-(3-chloro-6-(2-fluoro-6-methylphenyl)imidazo[1,2-a] pyridin-2-yl)-2-fluorocyclopropane-1-carboxamide;
2-fluoro-N-(6-(3-fluoro-2-methylphenyl)-3-methylimidazo [1,2-a]pyridin-2-yl)cyclopropane-1-carboxamide;
2-fluoro-N-(6-(2-fluoro-6-methylphenyl)-3-methylimidazo [1,2-a]pyridin-2-yl)cyclopropane-1-carboxamide;

2-fluoro-N-(6-(5-fluoro-2-methylphenyl)imidazo[1,2-a]pyridin-2-yl)cyclopropane-1-carboxamide;
2-fluoro-N-(6-(5-hydroxy-2-methylphenyl)imidazo[1,2-a]pyridin-2-yl)cyclopropane-1-carboxamide;
2-fluoro-N-(6-(5-methyl-1H-indol-4-yl)imidazo[1,2-a]pyridin-2-yl)cyclopropane-1-carboxamide;
2-fluoro-N-(6-(3-hydroxy-2-methylphenyl)imidazo[1,2-a]pyridin-2-yl)cyclopropane-1-carboxamide;
N-(6-(2,3-dimethylphenyl)imidazo[1,2-a]pyridin-2-yl)-2-fluorocyclopropane-1-carboxamide;
2-fluoro-N-(6-(2-methyl-5-(methylamino)phenyl)imidazo[1,2-a]pyridin-2-yl)cyclopropane-1-carboxamide;
N-(6-(2,4-dimethylphenyl)imidazo[1,2-a]pyridin-2-yl)-2-fluorocyclopropane-1-carboxamide;
2-fluoro-N-(3-fluoro-6-(3-fluoro-2-methylphenyl)imidazo[1,2-a]pyridin-2-yl)cyclopropane-1-carboxamide;
N-(6-(2,5-dimethylphenyl)imidazo[1,2-a]pyridin-2-yl)-2-fluorocyclopropane-1-carboxamide;
2-fluoro-N-(6-(2-oxoindolin-6-yl)imidazo[1,2-a]pyridin-2-yl)cyclopropane-1-carboxamide;
2-fluoro-N-(6-(2-methyl-5-(1H-pyrrol-3-yl)phenyl)imidazo[1,2-a]pyridin-2-yl)cyclopropane-1-carboxamide;
N-(6-(2,6-dimethylphenyl)imidazo[1,2-a]pyridin-2-yl)-2-fluorocyclopropane-1-carboxamide;
2-fluoro-N-(6-(4-fluoro-5-hydroxy-2-methylphenyl)imidazo[1,2-a]pyridin-2-yl)cyclopropane-1-carboxamide;
2-fluoro-N-(6-(5-methyl-2-oxoindolin-4-yl)imidazo[1,2-a]pyridin-2-yl)cyclopropane-1-carboxamide;
N-(3-bromo-6-(3-fluoro-2-methylphenyl)imidazo[1,2-a]pyridin-2-yl)-2-fluorocyclopropane-1-carboxamide;
N-(6-(3,5-dimethyl-1H-indol-4-yl)imidazo[1,2-a]pyridin-2-yl)-2-fluorocyclopropanecarboxamide;
2-fluoro-N-(6-(3-fluoro-2-methylphenyl)imidazo[1,2-a]pyridin-2-yl)cyclopropanecarboxamide;
2-fluoro-N-(6-(3-fluoro-2-methylphenyl)imidazo[1,2-a]pyridin-2-yl)cyclopropanecarboxamide;
2-fluoro-N-(6-(3-fluoro-2-methylphenyl)imidazo[1,2-a]pyridin-2-yl)cyclopropanecarboxamide;
2-fluoro-N-(6-(5-methyl-1H-indol-6-yl)imidazo[1,2-a]pyridin-2-yl)cyclopropanecarboxamide;
2-fluoro-N-(6-(6-methyl-1H-indol-5-yl)imidazo[1,2-a]pyridin-2-yl)cyclopropanecarboxamide; and
2-fluoro-N-(6-(5-methylbenzo[d]thiazol-6-yl)imidazo[1,2-a]pyridin-2-yl)cyclopropanecarboxamide.

In one embodiment, the compound of Formula (I) is selected from compounds according to Formula (II) and pharmaceutically acceptable salts thereof:

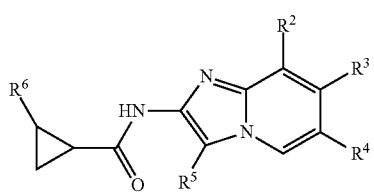

Formula II wherein $R^6$ is selected from the group consisting of halo, $C_1$-$C_3$ alkyl, $C_1$-$C_3$ hydroxyalkyl and $C_1$-$C_3$ haloalkyl and $R^2$, $R^3$, $R^4$, and $R^5$ are as defined above.

In one embodiment, the compound of Formula (I) is a compound of which $R^1$ is cyclopropyl. In an embodiment, the compound of Formula (I) is N-(6-(3-fluoro-2-methylphenyl)imidazo[1,2-a]pyridin-2-yl)cyclopropanecarboxamide or a salt thereof.

In another embodiment, the compound of Formula (I) is a compound of which $R^1$ is cyclobutyl which is optionally substituted with one or more groups selected from the group consisting of halo, alkyl, hydroxyalkyl, haloalkyl, and monoalkylaminoalkyl; and $R^2$, $R^3$, $R^4$, and $R^5$ are as defined above. In various embodiments, the compound of Formula (I) is selected from the group consisting of the following compounds and salts thereof:

N-(6-(3-fluoro-2-methylphenyl)imidazo[1,2-a]pyridin-2-yl)cyclobutanecarboxamide;
3-fluoro-N-(6-(3-fluoro-2-methylphenyl)imidazo[1,2-a]pyridin-2-yl)cyclobutanecarboxamide; and
3,3-difluoro-N-(6-(3-fluoro-2-methylphenyl)imidazo[1,2-a]pyridin-2-yl)cyclobutanecarboxamide.

The compounds of the present disclosure include stereoisomers of the compounds described herein. In some embodiments, the compounds are stereochemically pure compounds such as those substantially free (e.g., greater than 85% ee, greater than 90% ee, greater than 95% ee, greater than 97% ee, or greater than 99% ee) of other stereoisomers. Examples of such stereoisomers include, but are not limited to,

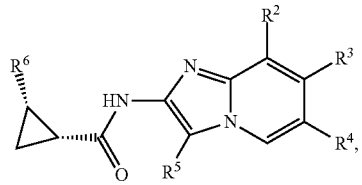

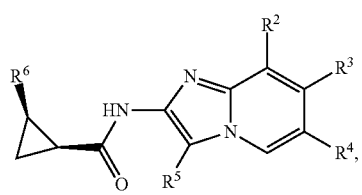

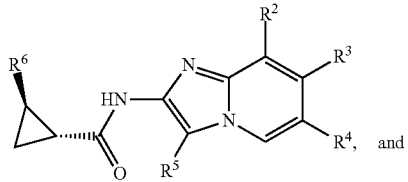

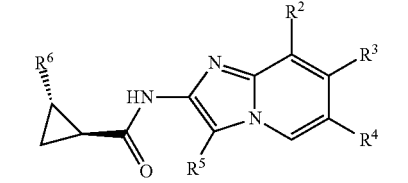

wherein $R^2$, $R^3$, $R^4$, $R^5$, and $R^6$ are as defined above.

In one embodiment, the compound of Formula (I) is selected from compounds according to Formula (III) and pharmaceutically acceptable salts thereof:

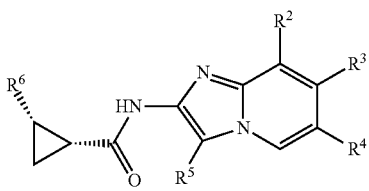

Formula III wherein R⁶ is selected from the group consisting of halo, $C_1$-$C_3$ alkyl, $C_1$-$C_3$ hydroxyalkyl and $C_1$-$C_3$ haloalkyl and $R^2$, $R^3$, $R^4$, and $R^5$ are as defined above. Table 1 shows exemplary compounds having the stereochemistry of Formula (III). Examples of the compound of Formula (III) include, but are not limited to, the following compounds and salts thereof:

(1S,2S)-2-fluoro-N-(6-(3-fluoro-2-methylphenyl)imidazo[1,2-a]pyridin-2-yl)cyclopropane-1-carboxamide;
(1S,2S)-2-fluoro-N-(6-(2-fluoro-6-methylphenyl)imidazo[1,2-a]pyridin-2-yl)cyclopropane-1-carboxamide;
(1S,2S)—N-(3-chloro-6-(3-fluoro-2-methylphenyl)imidazo[1,2-a]pyridin-2-yl)-2-fluorocyclopropane-1-carboxamide;
(1S,2S)—N-(3-chloro-6-(2-fluoro-6-methylphenyl)imidazo[1,2-a]pyridin-2-yl)-2-fluorocyclopropane-1-carboxamide;
(1S,2S)-2-fluoro-N-(3-methyl-6-(4-methylpyridin-3-yl)imidazo[1,2-a]pyridin-2-yl)cyclopropane-1-carboxamide;
(1S,2S)-2-fluoro-N-(6-(4-methylpyridin-3-yl)imidazo[1,2-a]pyridin-2-yl)cyclopropane-1-carboxamide;
(1S,2S)—N-(3-chloro-6-(4-methylpyridin-3-yl)imidazo[1,2-a]pyridin-2-yl)-2-fluorocyclopropane-1-carboxamide;
(1S,2S)-2-fluoro-N-(6-(3-fluoro-2-methylphenyl)-3-methylimidazo[1,2-a]pyridin-2-yl)cyclopropane-1-carboxamide;
(1S,2S)-2-fluoro-N-(6-(2-fluoro-6-methylphenyl)-3-methylimidazo[1,2-a]pyridin-2-yl)cyclopropane-1-carboxamide;
(1S,2S)-2-fluoro-N-(6-(5-fluoro-4-methylpyridin-3-yl)-3-methylimidazo[1,2-a]pyridin-2-yl)cyclopropane-1-carboxamide;
(1S,2S)-2-fluoro-N-(6-(5-fluoro-2-methylphenyl)imidazo[1,2-a]pyridin-2-yl)cyclopropane-1-carboxamide;
(1S,2S)-2-fluoro-N-(6-(5-hydroxy-2-methylphenyl)imidazo[1,2-a]pyridin-2-yl)cyclopropane-1-carboxamide;
methyl 3-(2-((1S,2S)-2-fluorocyclopropane-1-carboxamido)imidazo[1,2-a]pyridin-6-yl)-4-methylbenzoate;
(1S,2S)-2-fluoro-N-(6-(5-fluoro-4-methylpyridin-3-yl)imidazo[1,2-a]pyridin-2-yl)cyclopropane-1-carboxamide;
(1S,2S)-2-fluoro-N-(6-(5-methyl-1H-indol-4-yl)imidazo[1,2-a]pyridin-2-yl)cyclopropane-1-carboxamide;
(1S,2S)—N-(3-chloro-6-(5-fluoro-4-methylpyridin-3-yl)imidazo[1,2-a]pyridin-2-yl)-2-fluorocyclopropane-1-carboxamide;
(1S,2S)—N-(6-(5-cyano-2-methylphenyl)imidazo[1,2-a]pyridin-2-yl)-2-fluorocyclopropane-1-carboxamide;
(1S,2S)—N-(6-(1H-pyrazol-3-yl)imidazo[1,2-a]pyridin-2-yl)-2-fluorocyclopropane-1-carboxamide;
(1S,2S)-2-fluoro-N-(6-(4-methyl-1H-pyrazol-3-yl)imidazo[1,2-a]pyridin-2-yl)cyclopropane-1-carboxamide;
(1S,2S)-2-fluoro-N-(6-(3-hydroxy-2-methylphenyl)imidazo[1,2-a]pyridin-2-yl)cyclopropane-1-carboxamide;
(1S,2S)—N-(6-(4-chloropyridin-3-yl)imidazo[1,2-a]pyridin-2-yl)-2-fluorocyclopropane-1-carboxamide;
(1S,2S)—N-(6-(2,3-dimethylphenyl)imidazo[1,2-a]pyridin-2-yl)-2-fluorocyclopropane-1-carboxamide;
(1S,2S)—N-(6-(5-amino-2-methylphenyl)imidazo[1,2-a]pyridin-2-yl)-2-fluorocyclopropane-1-carboxamide;
(1S,2S)-2-fluoro-N-(6-(2-methyl-5-(methylamino)phenyl)imidazo[1,2-a]pyridin-2-yl)cyclopropane-1-carboxamide;
(1S,2S)—N-(6-(5-acetamido-2-methylphenyl)imidazo[1,2-a]pyridin-2-yl)-2-fluorocyclopropane-1-carboxamide;
(1S,2S)—N-(6-(5-chloro-2-methylphenyl)imidazo[1,2-a]pyridin-2-yl)-2-fluorocyclopropane-1-carboxamide;
(1S,2S)—N-(6-(1H-pyrrolo[2,3-b]pyridin-5-yl)imidazo[1,2-a]pyridin-2-yl)-2-fluorocyclopropane-1-carboxamide;
(1S,2S)-2-fluoro-N-(6-(2-methyl-5-(1H-pyrazol-3-yl)phenyl)imidazo[1,2-a]pyridin-2-yl)cyclopropane-1-carboxamide;
(1S,2S)—N-(6-(4-chloro-2-methylphenyl)imidazo[1,2-a]pyridin-2-yl)-2-fluorocyclopropane-1-carboxamide;
(1S,2S)—N-(6-(3-chloro-2-methylphenyl)imidazo[1,2-a]pyridin-2-yl)-2-fluorocyclopropane-1-carboxamide;
(1S,2S)-2-fluoro-N-(6-(4-(trifluoromethyl)pyridin-3-yl)imidazo[1,2-a]pyridin-2-yl)cyclopropane-1-carboxamide;
(1S,2S)—N-(6-(2,4-dimethylphenyl)imidazo[1,2-a]pyridin-2-yl)-2-fluorocyclopropane-1-carboxamide;
(1S,2S)-2-fluoro-N-(3-fluoro-6-(3-fluoro-2-methylphenyl)imidazo[1,2-a]pyridin-2-yl)cyclopropane-1-carboxamide;
(1S,2S)—N-(6-(2,5-dimethylphenyl)imidazo[1,2-a]pyridin-2-yl)-2-fluorocyclopropane-1-carboxamide;
(1S,2S)-2-fluoro-N-(6-(2-oxoindolin-6-yl)imidazo[1,2-a]pyridin-2-yl)cyclopropane-1-carboxamide;
(1S,2S)—N-(6-(4-cyanopyridin-3-yl)imidazo[1,2-a]pyridin-2-yl)-2-fluorocyclopropane-1-carboxamide;
(1S,2S)-2-fluoro-N-(6-(4-fluoro-2,3-dimethylphenyl)imidazo[1,2-a]pyridin-2-yl)cyclopropane-1-carboxamide;
(1S,2S)-2-fluoro-N-(6-(4-fluoro-2,6-dimethylphenyl)imidazo[1,2-a]pyridin-2-yl)cyclopropane-1-carboxamide;
(1S,2S)-2-fluoro-N-(6-(4-fluoro-2-methylphenyl)imidazo[1,2-a]pyridin-2-yl)cyclopropane-1-carboxamide;
(1S,2S)-2-fluoro-N-(6-(2-methyl-5-(1H-pyrrol-3-yl)phenyl)imidazo[1,2-a]pyridin-2-yl)cyclopropane-1-carboxamide;
(1S,2S)-2-fluoro-N-(6-(3-methylthiophen-2-yl)imidazo[1,2-a]pyridin-2-yl)cyclopropane-1-carboxamide;
(1S,2S)—N-(6-(2,6-dimethylphenyl)imidazo[1,2-a]pyridin-2-yl)-2-fluorocyclopropane-1-carboxamide;
(1S,2S)-2-fluoro-N-(6-(4-fluoro-5-hydroxy-2-methylphenyl)imidazo[1,2-a]pyridin-2-yl)cyclopropane-1-carboxamide;
(1S,2S)—N-(6-(3,4-difluoro-2-methylphenyl)imidazo[1,2-a]pyridin-2-yl)-2-fluorocyclopropane-1-carboxamide;
(1S,2S)—N-(6-(3,6-difluoro-2-methylphenyl)imidazo[1,2-a]pyridin-2-yl)-2-fluorocyclopropane-1-carboxamide;
(1S,2S)—N-(6-(4-chloro-3-fluoro-2-methylphenyl)imidazo[1,2-a]pyridin-2-yl)-2-fluorocyclopropane-1-carboxamide;
(1S,2S)-2-fluoro-N-(6-(2-fluoro-4-methylpyridin-3-yl)imidazo[1,2-a]pyridin-2-yl)cyclopropane-1-carboxamide;
(1S,2S)-2-fluoro-N-(6-(4-methoxypyridin-3-yl)imidazo[1,2-a]pyridin-2-yl)cyclopropane-1-carboxamide;
(1S,2S)—N-(6-(6-amino-4-methylpyridin-3-yl)imidazo[1,2-a]pyridin-2-yl)-2-fluorocyclopropane-1-carboxamide;
(1S,2S)—N-(6-(5-amino-3-fluoro-2-methylphenyl)imidazo[1,2-a]pyridin-2-yl)-2-fluorocyclopropane-1-carboxamide;
(1S,2S)-2-fluoro-N-(6-(5-methyl-2-oxoindolin-4-yl)imidazo[1,2-a]pyridin-2-yl)cyclopropane-1-carboxamide;

(1S,2S)—N-(6-(2-chloro-6-methylphenyl)imidazo[1,2-a]pyridin-2-yl)-2-fluorocyclopropane-1-carboxamide;
(1S,2S)-2-fluoro-N-(6-(3-methyl-1H-pyrrolo[2,3-b]pyridin-5-yl)imidazo[1,2-a]pyridin-2-yl)cyclopropane-1-carboxamide;
(1S,2S)-2-fluoro-N-(6-(2-oxo-2,3-dihydrobenzo[d]thiazol-5-yl)imidazo[1,2-a]pyridin-2-yl)cyclopropane-1-carboxamide;
(1S,2S)—N-(6-(6-aminopyridin-3-yl)imidazo[1,2-a]pyridin-2-yl)-2-fluorocyclopropane-1-carboxamide;
(1S,2S)-2-fluoro-N-(6-(2-methyl-5-(1H-pyrazol-1-yl)phenyl)imidazo[1,2-a]pyridin-2-yl)cyclopropane-1-carboxamide;
(1S,2S)-2-fluoro-N-(6-(3-fluoro-2-(hydroxymethyl)phenyl)imidazo[1,2-a]pyridin-2-yl)cyclopropane-1-carboxamide;
(1S,2S)—N-(3-bromo-6-(3-fluoro-2-methylphenyl)imidazo[1,2-a]pyridin-2-yl)-2-fluorocyclopropane-1-carboxamide;
(1S,2S)-2-fluoro-N-(6-(3-fluoro-2-methoxyphenyl)imidazo[1,2-a] pyridin-2-yl)cyclopropanecarboxamide;
(1S,2S)—N-(6-(2-cyano-3-fluorophenyl)imidazo[1,2-a]pyridin-2-yl)-2-fluorocyclopropanecarboxamide;
(1S,2S)—N-(6-(2-chloro-3-fluorophenyl)imidazo[1,2-a]pyridin-2-yl)-2-fluorocyclopropanecarboxamide;
(1S,2S)—N-(6-(2,3-difluorophenyl)imidazo[1,2-a]pyridin-2-yl)-2-fluorocyclopropanecarboxamide;
(1S,2S)—N-(6-(3,5-dimethyl-1H-indol-4-yl)imidazo[1,2-a]pyridin-2-yl)-2-fluorocyclopropanecarboxamide;
(1S,2S)-2-fluoro-N-(6-(3-fluoro-2-(methoxymethyl)phenyl)imidazo[1,2-a]pyridin-2-yl)cyclopropanecarboxamide;
(1S,2S)-2-fluoro-N-(6-(3-fluoro-2-(furan-2-yl)phenyl)imidazo[1,2-a]pyridin-2-yl)cyclopropanecarboxamide;
(1S,2S)-2-fluoro-N-(6-(3-fluoro-2-(methylthio)phenyl)imidazo[1,2-a]pyridin-2-yl)cyclopropanecarboxamide;
(1S,2S)-2-fluoro-N-(6-(6-fluoro-4-methyl pyridin-3-yl)imidazo[1,2-a]pyridin-2-yl)cyclopropanecarboxamide;
(1S,2S)—N-(6-(2-acetyl-3-fluorophenyl)imidazo[1,2-a]pyridin-2-yl)-2-fluorocyclopropanecarboxamide;
(1S,2S)—N-(6-(6-(dimethylamino)-4-methyl pyridin-3-yl)imidazo[1,2-a]pyridin-2-yl)-2-fluorocyclopropanecarboxamide;
N-(6-(3-fluoro-2-methylphenyl)imidazo[1,2-a]pyridin-2-yl)cyclopropanecarboxamide
(1S,2S)—N-(6-(2-(aminomethyl)-3-fluorophenyl)imidazo[1,2-a]pyridin-2-yl)-2-fluorocyclopropanecarboxamide;
(1S,2S)—N-(6-(2-(acetamidomethyl)-3-fluorophenyl)imidazo[1,2-a]pyridin-2-yl)-2-fluorocyclopropanecarboxamide;
(1S,2S)-2-fluoro-N-(6-(3-fluoro-2-((methylamino)methyl)phenyl)imidazo[1,2-a]pyridin-2-yl)cyclopropanecarboxamide;
(1S,2S)-2-fluoro-N-(6-(3-fluoro-2-((isopropylamino)methyl)phenyl)imidazo[1,2-a]pyridin-2-yl)cyclopropanecarboxamide;
(1S,2S)-2-fluoro-N-(6-(3-fluoro-2-((2-methoxyethoxy)methyl)phenyl)imidazo[1,2-a]pyridin-2-yl)cyclopropanecarboxamide;
(1S,2S)-2-fluoro-N-(6-(3-fluoro-2-((2-hydroxyethoxy)methyl)phenyl)imidazo[1,2-a]pyridin-2-yl)cyclopropanecarboxamide;
(1S,2S)—N-(6-(2-((dimethylamino)methyl)-3-fluorophenyl)imidazo[1,2-a]pyridin-2-yl)-2-fluorocyclopropanecarboxamide;
(1S,2S)—N-(6-(1H-pyrrolo[2,3-b]pyridin-5-yl)imidazo[1,2-a]pyridin-2-yl)-2-fluorocyclopropanecarboxamide;
(1S,2S)-2-fluoro-N-(6-(4-methyl-1H-pyrrolo[2,3-b]pyridin-5-yl)imidazo[1,2-a]pyridin-2-yl)cyclopropanecarboxamide;
(1S,2S)—N-(6-(4-chloro-1H-pyrrolo[2,3-b]pyridin-5-yl)imidazo[1,2-a]pyridin-2-yl)-2-fluorocyclopropanecarboxamide;
(1S,2S)-2-fluoro-N-(6-(o-tolyl)imidazo[1,2-a]pyridin-2-yl)cyclopropanecarboxamide;
(1S,2S)-2-fluoro-N-(6-(3-fluoro-2-hydroxyphenyl)imidazo[1,2-a]pyridin-2-yl)cyclopropanecarboxamide;
(1S,2S)—N-(6-(2-amino-3-fluorophenyl)imidazo[1,2-a]pyridin-2-yl)-2-fluorocyclopropanecarboxamide;
(1S,2S)-2-fluoro-N-(6-(5-methyl-1H-indol-6-yl)imidazo[1,2-a]pyridin-2-yl)cyclopropanecarboxamide;
(1S,2S)-2-fluoro-N-(6-(6-methyl-1H-indol-5-yl)imidazo[1,2-a]pyridin-2-yl)cyclopropanecarboxamide;
(1S,2S)—N-(6-(2-(dimethylamino)-3-fluorophenyl)imidazo[1,2-a]pyridin-2-yl)-2-fluorocyclopropanecarboxamide;
(1S,2S)-2-fluoro-N-(6-(5-methyl-1H-benzo[d]imidazol-6-yl)imidazo[1,2-a]pyridin-2-yl)cyclopropanecarboxamide;
(1S,2S)—N-(6-(2-ethyl-3-fluorophenyl)imidazo[1,2-a]pyridin-2-yl)-2-fluorocyclopropanecarboxamide;
(1S,2S)-2-fluoro-N-(6-(3-fluoro-2-(trifluoromethyl)phenyl)imidazo[1,2-a]pyridin-2-yl)cyclopropanecarboxamide;
(1S,2S)—N-(6-(2-cyclopropyl-3-fluorophenyl)imidazo[1,2-a]pyridin-2-yl)-2-fluorocyclopropanecarboxamide;
(1S,2S)-2-fluoro-N-(6-(3-fluoro-2-(methylamino)phenyl)imidazo[1,2-a]pyridin-2-yl)cyclopropanecarboxamide;
(1S,2S)-2-fluoro-N-(6-(5-methylbenzo[d]oxazol-6-yl)imidazo[1,2-a]pyridin-2-yl)cyclopropanecarboxamide;
(1S,2S)-2-fluoro-N-(6-(5-methyl-1H-benzo[d]imidazol-4-yl)imidazo[1,2-a]pyridin-2-yl)cyclopropane-1-carboxamide;
(1S,2S)-2-fluoro-N-(6-(6-methylbenzo[d]thiazol-5-yl)imidazo[1,2-a]pyridin-2-yl)cyclopropanecarboxamide;
(1S,2S)-2-fluoro-N-(6-(5-methylbenzo[d]oxazol-4-yl)imidazo[1,2-a]pyridin-2-yl)cyclopropanecarboxamide;
(1S,2S)-2-fluoro-N-(6-(5-methylbenzo[d]thiazol-6-yl)imidazo[1,2-a]pyridin-2-yl)cyclopropanecarboxamide;
(1S,2S)-2-fluoro-N-(6-(7-methylbenzo[d]thiazol-6-yl)imidazo[1,2-a]pyridin-2-yl)cyclopropanecarboxamide; and
(1S,2S)-2-fluoro-N-(6-(3-fluoro-2-isopropylphenyl)imidazo[1,2-a]pyridin-2-yl)cyclopropanecarboxamide.

In particular embodiments, the compound of Formula (I) is selected from the group consisting of the following compounds and salts thereof:
(1S,2S)-2-fluoro-N-(6-(3-fluoro-2-methylphenyl)imidazo[1,2-a]pyridin-2-yl)cyclopropane-1-carboxamide;
(1S,2S)-2-fluoro-N-(6-(5-fluoro-2-methylphenyl)imidazo[1,2-a]pyridin-2-yl)cyclopropane-1-carboxamide;
(1S,2S)-2-fluoro-N-(6-(5-hydroxy-2-methylphenyl)imidazo[1,2-a]pyridin-2-yl)cyclopropane-1-carboxamide;
(1S,2S)-2-fluoro-N-(6-(5-methyl-1H-indol-4-yl)imidazo[1,2-a]pyridin-2-yl)cyclopropane-1-carboxamide;
(1S,2S)-2-fluoro-N-(6-(2-methyl-5-(methylamino)phenyl)imidazo[1,2-a]pyridin-2-yl)cyclopropane-1-carboxamide;
(1S,2S)—N-(6-(2,5-dimethylphenyl)imidazo[1,2-a]pyridin-2-yl)-2-fluorocyclopropane-1-carboxamide;
(1S,2S)-2-fluoro-N-(6-(2-methyl-5-(1H-pyrrol-3-yl)phenyl)imidazo[1,2-a]pyridin-2-yl)cyclopropane-1-carboxamide;
(1S,2S)-2-fluoro-N-(6-(4-fluoro-5-hydroxy-2-methylphenyl)imidazo[1,2-a]pyridin-2-yl)cyclopropane-1-carboxamide;

(1S,2S)-2-fluoro-N-(6-(6-methyl-1H-indol-5-yl)imidazo[1,2-a]pyridin-2-yl)cyclopropanecarboxamide; and (1S,2S)-2-fluoro-N-(6-(5-methylbenzo[d]thiazol-6-yl)imidazo[1,2-a]pyridin-2-yl)cyclopropanecarboxamide.

The present disclosure provides pharmaceutically acceptable salts of the compounds described above. The pharmaceutically acceptable salts are as defined above in the definition section. In some embodiments, the salt is hydrochloric acid salt, tartaric acid salt, phosphoric acid salt, or maleic acid salt.

Methods of Treatment

The present disclosure further provides methods for treating a neurodegenerative disease or disorder in a subject having or susceptible to having such a disease or disorder, by administering to the subject a therapeutically effective amount of one or more compounds as described above. In one embodiment, the treatment is preventative treatment. In another embodiment, the treatment is palliative treatment. In another embodiment, the treatment is restorative treatment.

1. Diseases or Conditions

The compound of the present disclosure for inhibiting c-abl and/or LRRK2 activity is useful for treatment or prevention of a neurodegenerative disease or disorder. The compound can be used for inhibiting or hindering c-abl and/or LRRK2 kinase activity, and for treating a neurodegenerative disease or disorder, or for preventing aggravation of such disease. Thus, the present disclosure provides a method for inhibiting or hindering c-abl and/or LRRK2 activity in a cell, wherein the cell is contacted with an effective amount of a compound of the present disclosure. In one embodiment, such cell is present in a subject (for example, Alzheimer patients). In another embodiment, there is provided a medical use for treating or preventing a neurodegenerative disease or disorder in a subject, using the compound according to the present disclosure. The method of the present disclosure comprises administering to a subject in need of treatment or prevention of a neurodegenerative disease or disorder with a pharmaceutical composition containing a therapeutically or prophylactically effective amount of c-abl and/or LRRK2 inhibitor. The neurodegenerative disease or disorder includes, but is not limited to, α-synucleinopathy, Parkinson's disease, dementia with Lewy body, multiple system atrophy (MSA), Alzheimer's disease or amyotrophic lateral sclerosis (ALS). And also a medical use for the present disclosure includes the inflammatory disease, inflammatory bowel disease, Crohn's disease, ulcerative colitis, rheumatoid arthritis, psoriasis, contact dermatitis or delayed hypersensitivity reactions.

2. Subjects

Suitable subjects to be treated according to the present disclosure include mammalian subjects. Mammals according to the present disclosure include, but are not limited to, human, canine, feline, bovine, caprine, equine, ovine, porcine, rodents, lagomorphs, primates, and the like, and encompass mammals in utero. Subjects may be of either gender and at any stage of development. In one embodiment, the suitable subject to be treated according to the present disclosure is human.

3. Administration and Dosing

The compounds of the present disclosure are generally administered in a therapeutically effective amount. The compounds of the present disclosure can be administered by any suitable route in the form of a pharmaceutical composition adapted to such a route, and in a dose effective for the treatment intended. An effective dosage is typically in the range of about 0.001 to about 100 mg per kg body weight per day, preferably about 0.01 to about 50 mg/kg/day, in single or divided doses. Depending on age, species and disease or condition being treated, dosage levels below the lower limit of this range may be suitable. In other cases, still larger doses may be used without harmful side effects. Larger doses may also be divided into several smaller doses, for administration throughout the day. Methods for determining suitable doses are well known in the art to which the present disclosure pertains. For example, Remington: The Science and Practice of Pharmacy, Mack Publishing Co., 20th ed., 2000 can be used.

Pharmaceutical Compositions, Dosage Forms and Administration Routes

For the treatment of the diseases or conditions referred to above, the compounds described herein or pharmaceutically acceptable salts thereof can be administered as follows:

Oral Administration

The compounds of the present disclosure may be administered orally, including by swallowing, so that the compound enters the gastrointestinal tract, or absorbed into the blood stream directly from the mouth (e.g., buccal or sublingual administration).

Suitable compositions for oral administration include solid, liquid, gel or powder formulations, and have a dosage form such as tablet, lozenge, capsule, granule or powder.

Compositions for oral administration may be formulated as immediate or modified release, including delayed or sustained release, optionally with enteric coating.

Liquid formulations can include solutions, syrups and suspensions, which can be used in soft or hard capsules. Such formulations may include a pharmaceutically acceptable carrier, for example, water, ethanol, polyethylene glycol, cellulose, or an oil. The formulation may also include one or more emulsifying agents and/or suspending agents.

In a tablet dosage form the amount of drug present may be from about 0.05% to about 95% by weight, more typically from about 2% to about 50% by weight of the dosage form. In addition, tablets may contain a disintegrant, comprising from about 0.5% to about 35% by weight, more typically from about 2% to about 25% of the dosage form. Examples of disintegrants include, but are not limited to, lactose, starch, sodium starch glycolate, crospovidone, croscarmellose sodium, maltodextrin, or mixtures thereof.

Suitable lubricants, for use in a tablet, may be present in amounts from about 0.1% to about 5% by weight, and include, but are not limited to, talc, silicon dioxide, stearic acid, calcium, zinc or magnesium stearate, sodium stearyl fumarate and the like.

Suitable binders, for use in a tablet, include, but are not limited to, gelatin, polyethylene glycol, sugars, gums, starch, polyvinyl pyrrolidone, hydroxypropyl cellulose, hydroxypropylmethyl cellulose and the like. Suitable diluents, for use in a tablet, include, but are not limited to, mannitol, xylitol, lactose, dextrose, sucrose, sorbitol, microcrystalline cellulose and starch.

Suitable solubilizers, for use in a tablet, may be present in amounts from about 0.1% to about 3% by weight, and include, but are not limited to, polysorbates, sodium lauryl sulfate, sodium dodecyl sulfate, propylene carbonate, diethyleneglycol monoethyl ether, dimethyl isosorbide, polyethylene glycol (natural or hydrogenated) castor oil, HCOR™ (Nikkol), oleyl ester, Gelucire™, caprylic/caprylic acid mono/diglyceride, sorbitan fatty acid esters, and Solutol HS™.

Parenteral Administration

Compounds of the present disclosure may be administered directly into the blood stream, muscle, or internal organs. Suitable means for parenteral administration include intravenous, intra-muscular, subcutaneous intraarterial, intraperitoneal, intrathecal, intracranial, and the like. Suitable devices for parenteral administration include injectors (including needle and needle-free injectors) and infusion methods.

Compositions for parenteral administration may be formulated as immediate or modified release, including delayed or sustained release. Most parenteral formulations are aqueous solutions containing excipients, including salts, buffering agents and isotonic agents. Parenteral formulations may also be prepared in a dehydrated form (e.g., by lyophilization) or as sterile non-aqueous solutions. These formulations can be used with a suitable vehicle, such as sterile water. Solubility-enhancing agents may also be used in preparation of parenteral solutions.

Transdermal Administration

Compounds of the present disclosure may be administered topically to the skin or transdermally. Formulations for this topical administration can include lotions, solutions, creams, gels, hydrogels, ointments, foams, implants, patches and the like. Pharmaceutically acceptable carriers for topical administration formulations can include water, alcohol, mineral oil, glycerin, polyethylene glycol and the like. Topical or transdermal administration can also be performed by electroporation, iontophoresis, phonophoresis and the like.

Compositions for topical administration may be formulated as immediate or modified release, including delayed or sustained release.

Combination Therapy

A pharmaceutical composition according to the present disclosure may contain one or more additional therapeutic agents, for example, to increase the efficacy or decrease the side effects. In some embodiments, accordingly, a pharmaceutical composition further contains one or more additional therapeutic agents selected from active ingredients useful to treat or inhibit diseases mediated directly or indirectly by c-abl and/or LRRK2 kinase. Examples of such active ingredients are, without limitation, agents such as DNL151 and DNL201 to treat a neurodegenerative disease or disorder.

References for Preparing Pharmaceutical Compositions

Methods for preparing pharmaceutical compositions for treating or preventing a disease or condition are well known in the art to which the present disclosure pertains. For example, based on *Handbook of Pharmaceutical Excipients* (7$^{th}$ ed.), *Remington: The Science and Practice of Pharmacy* (20$^{th}$ ed.), *Encyclopedia of Pharmaceutical Technology* (3$^{rd}$ ed.), or *Sustained and Controlled Release Drug Delivery Systems* (1978), pharmaceutically acceptable excipients, carriers, additives and so on can be selected and then mixed with the compounds of the present disclosure for making the pharmaceutical compositions.

The present disclosure provides a compound having various pharmacological effects by inhibiting c-abl and/or LRRK2 activity, a pharmaceutical composition having the compound as an effective agent, a medical use, particularly for treating a neurodegenerative disease or disorder, of the compound, and a method of treatment or prevention comprising administering the compound to a subject in need of such treatment or prevention. The compounds of the present disclosure and pharmaceutically acceptable salts thereof have good safety and high selectivity for c-abl and/or LRRK2, and thus exhibit superior property as a drug.

EXAMPLES

Hereinafter, the present disclosure is described in considerable detail with examples to help those skilled in the art understand the present disclosure. However, the following examples are offered by way of illustration and are not intended to limit the scope of the invention. It is apparent that various changes may be made without departing from the spirit and scope of the invention or sacrificing all of its material advantages.

Synthesis of Formula (I) Compounds

Synthetic methods A to N were used to prepare the compounds of the following. Below, the illustrating synthetic examples of some compounds of the present disclosure are described, and other compounds can be prepared by the similar method to the one described below with different starting or reacting materials.

Synthetic Method A

Example 1. (1S,2S)-2-fluoro-N-(6-(3-fluoro-2-methylphenyl)imidazo[1,2-a]pyridin-2-yl)cyclopropane-1-carboxamide Hydrochloride

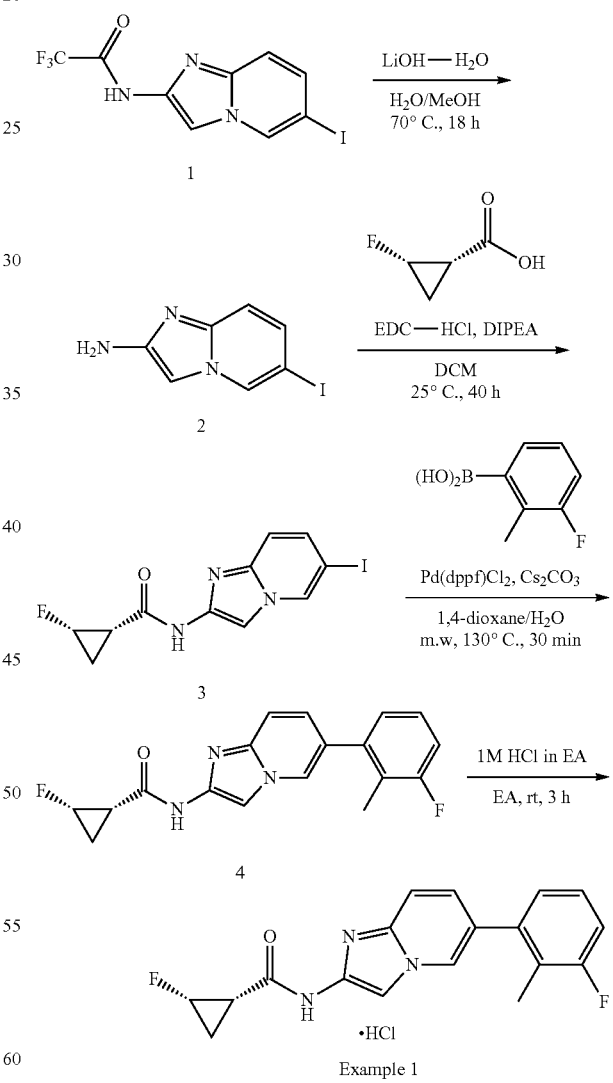

Example 1

Step 1) 6-iodoimidazo[1,2-a]pyridin-2-amine

A mixture of Compound 1 (10.000 g, 28.164 mmol) and lithium hydroxide monohydrate (4.727 g, 112.657 mmol) in water (100 mL)/methanol (300 mL) was heated at reflux for 18 hr, cooled down to the room temperature, concentrated under the reduced pressure, and partitioned between ethyl acetate and saturated aqueous ammonium chloride solution. The organic layer was washed with aqueous saturated sodium chloride solution, separated, dried with anhydrous MgSO₄, filtered, and concentrated in vacuo. The residue was diluted with dichloromethane (30 mL) and hexane (200 mL) and stirred at the ambient temperature. The resulting precipitates were collected by filtration, washed by hexane, and dried to give Compound 2 as brown solid (5.890 g, 80.7%).

Step 2) (1S,2S)-2-fluoro-N-(6-iodoimidazo[1,2-a]pyridin-2-yl)cyclopropane-1-carboxamide A mixture of Compound 2 (5.890 g, 22.737 mmol), (1S,2S)-2-fluorocyclopropane-1-carboxylic acid (3.076 g, 29.558 mmol) and 1-Ethyl-3-(3-dimethylaminopropyl)carbodiimide hydrochloride (EDC·HCl, 6.538 g, 34.105 mmol) in dichloromethane (100 mL) was treated at the room temperature with N,N-diisopropylethylamine (2.376 mL, 13.642 mmol), stirred at the same temperature for 40 hr. The precipitates were collected by filtration, washed by dichloromethane, and dried to give Compound 3 as beige solid (3.870 g, 49.3%).

1H NMR (400 MHz, DMSO-d6) δ 10.99 (s, 1H), 8.87 (s, 1H), 8.02 (s, 1H), 7.36~7.23 (m, 2H), 4.97~4.77 (m, 1H), 2.09~2.07 (m, 1H), 1.65~1.57 (m, 1H), 1.16~1.09 (m, 1H).

Step 3) (1S,2S)-2-fluoro-N-(6-(3-fluoro-2-methylphenyl)imidazo[1,2-a]pyridin-2-yl)cyclopropane-1-carboxamide Compound 3 (1.000 g, 2.898 mmol), (3-fluoro-2-methylphenyl)boronic acid (0.535 g, 3.477 mmol), [1,1'-bis(diphenylphosphino)ferrocene]dichloropalladium(II) (Pd(dppf)Cl₂, 0.212 g, 0.290 mmol) and cesium carbonate (1.416 g, 4.346 mmol) in tetrahydrofuran (12 mL)/water (3 mL) was mixed at the room temperature and then heated at 100° C. under the microwaves for 30 min, cooled down to the room temperature, filtered through a celite pad to remove solids, and partitioned between ethyl acetate and saturated aqueous sodium bicarbonate solution. The organic layer was washed with aqueous saturated sodium chloride solution, separated, dried (anhydrous MgSO₄), filtered, and concentrated in vacuo. The residue was chromatographed (SiO₂, 45 g cartridge; ethyl acetate/hexane=70% to 100%) to give the crude product which was crystallized at the room temperature using diethylether (5 mL). The resulting precipitates were filtered, washed by diethylether, and dried to give Compound 4 as white solid (0.700 g, 73.8%)

Step 4) (1S,2S)-2-fluoro-N-(6-(3-fluoro-2-methylphenyl)imidazo[1,2-a]pyridin-2-yl)cyclopropane-1-carboxamide Hydrochloride A solution of Compound 4 (0.600 g, 1.833 mmol) in ethyl acetate (100 mL) was mixed at the room temperature with hydrochloric acid (1.00 M solution in EtOAc, 1.925 mL, 1.925 mmol). The reaction mixture was stirred at the same temperature for 3 hr. The precipitates were collected by filtration, washed by diethylether, and dried to give Example 1 as white solid (0.665 g, 99.7%).

1H NMR (400 MHz, DMSO-d6) δ 11.67 (s, 1H), 8.74 (s, 1H), 8.13 (s, 1H), 7.69 (d, J=9.2 Hz, 1H), 7.55 (d, J=9.2 Hz, 1H), 7.35~7.30 (m, 1H), 7.23 (t, J=9.2 Hz, 1H), 7.15 (d, J=7.2 Hz, 1H), 5.05~4.85 (m, 1H), 7.21~7.14 (m, 4H), 1.69~1.63 (m, 1H), 1.21~1.18 (m, 1H).

Synthetic Method B

Example 3. (1S,2S)—N-(3-chloro-6-(3-fluoro-2-methylphenyl)imidazo[1,2-a]pyridin-2-yl)-2-fluoro-cyclopropane-1-carboxamide

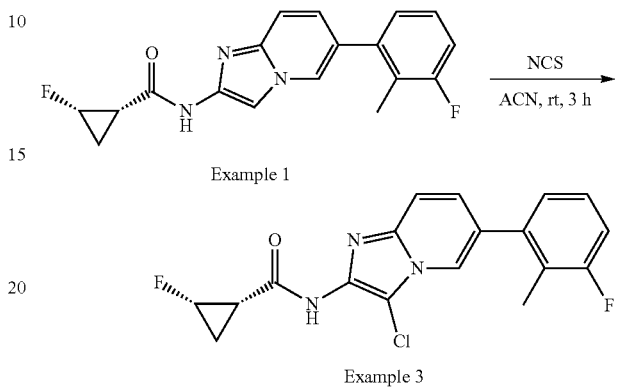

Step 1) (1S,2S)—N-(3-chloro-6-(3-fluoro-2-methylphenyl)imidazo[1,2-a]pyridin-2-yl)-2-fluorocyclopropane-1-carboxamide A solution of Example 1 (0.060 g, 0.183 mmol) in acetonitrile (8 mL) was mixed at the room temperature with 1-chloropyrrolidine-2,5-dione (NCS, 0.027 g, 0.202 mmol), stirred at the same temperature for 3 hr, and partitioned between ethyl acetate and saturated aqueous sodium bicarbonate solution. The organic layer was washed with aqueous saturated sodium chloride solution, separated, dried (anhydrous MgSO₄), filtered, and concentrated in vacuo. The residue was chromatographed (SiO₂, 12 g cartridge; ethyl acetate/hexane=70% to 100%) to give the crude product which was crystallized at the room temperature using diethylether (5 mL). The resulting precipitates were filtered, washed by diethylether, and dried to give Example 3 as white solid (0.015 g, 22.6%).

1H NMR (400 MHz, DMSO-d6) δ 10.44 (s, 1H), 8.21 (s, 1H), 7.62 (d, J=9.6 Hz, 1H), 7.35 (dd, J=9.2, 1.6 Hz, 1H), 7.30 (t, J=7.0 Hz, 1H), 7.24~7.19 (m, 2H), 5.01~4.83 (m, 1H), 2.15 (d, J=2.4 Hz, 3H), 2.06~2.03 (m, 1H), 1.64~1.56 (m, 1H), 1.15~1.08 (m, 1H).

Synthetic Method C

Example 5. (1S,2S)-2-fluoro-N-(3-methyl-6-(4-methylpyridin-3-yl)imidazo [1,2-a]pyridin-2-yl)cyclopropane-1-carboxamide

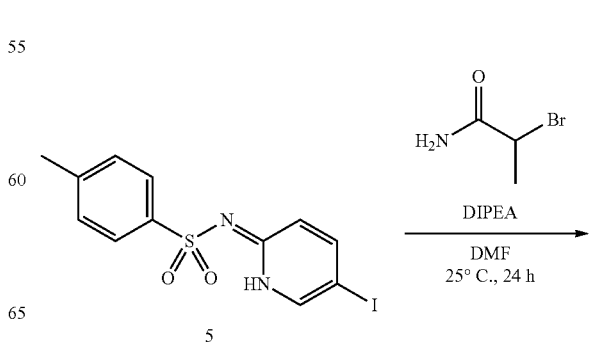

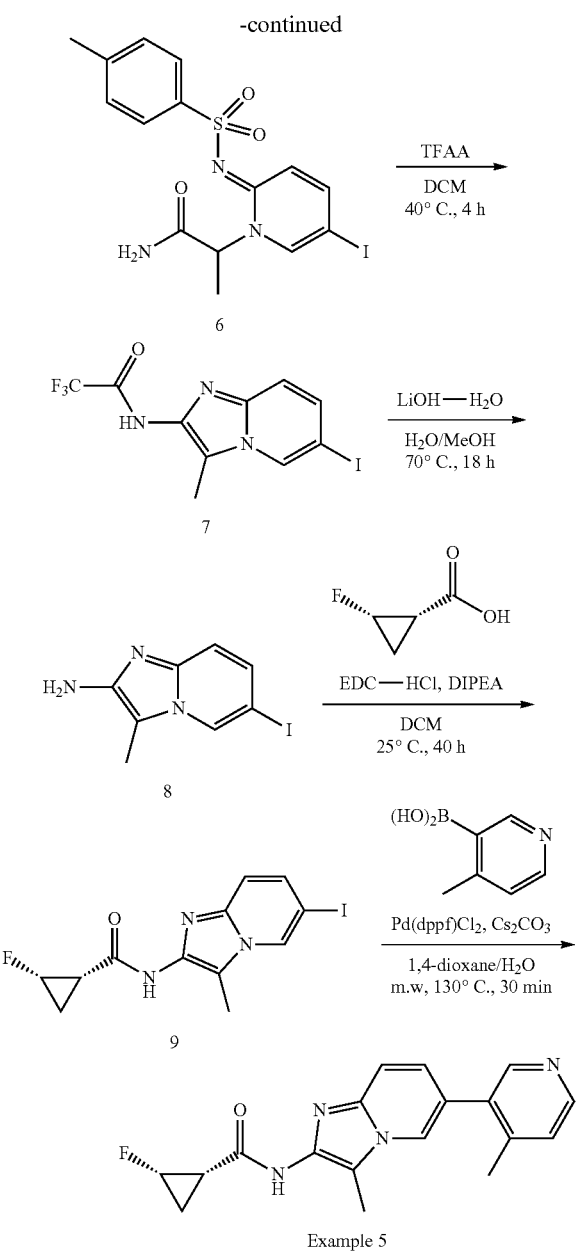

Example 5

Step 1) (E)-2-(5-iodo-2-(tosylimino)pyridin-1(2H)-yl)propanamide

A mixture of Compound 5 and 2-bromopropanamide (4.549 g, 29.931 mmol) in N,N-dimethylformamide (40 mL) was treated at the room temperature with N,N-diisopropylethylamine (5.213 mL, 29.931 mmol), stirred at the same temperature for 24 hr. The reaction mixture was diluted with water (500 mL) and stirred at the ambient temperature. The resulting precipitates were collected by filtration, washed by water, and dried to give the crude product which was re-dissolved in ethyl acetate (100 mL) and diethylether (300 mL) and stirred at the ambient temperature. The resulting precipitates were collected by filtration, washed by diethylether, and dried to give Compound 6 as pale pink solid (4.220 g, 35.5%).

1H NMR (400 MHz, DMSO-d6) δ 8.15 (d, J=1.6 Hz, 1H), 7.87 (dd, J=9.6, 2.4 Hz, 1H), 7.75 (s, 1H), 7.62 (d, J=8.0 Hz, 2H), 7.38 (s, 1H), 7.24 (d, J=8.4 Hz, 2H), 7.16 (d, J=9.6 Hz, 1H), 5.63 (m, 1H), 2.30 (s, 3H), 1.60 (d, J=7.2 Hz, 3H).

Step 2) 2,2,2-trifluoro-N-(6-iodo-3-methylimidazo[1,2-a]pyridin-2-yl)acetamide A stirred slurry of Compound 6 (4.220 g, 9.477 mmol) in dichloromethane (50 mL) was mixed at the room temperature with trifluoroacetic anhydride (8.032 mL, 56.863 mmol). The reaction mixture was heated at reflux for 4 hr, cooled down to the room temperature, and concentrated under the reduced pressure. The residue was diluted with diethylether (300 mL) and stirred at the ambient temperature. The resulting precipitates were collected by filtration, washed by diethylether, and dried to give the crude product which was re-dissolved in water (300 mL) and stirred at the ambient temperature. The resulting precipitates were collected by filtration, washed by water, and dried to give Compound 7 as beige solid (3.098 g, 88.6%).

Step 3) 6-iodo-3-methylimidazo[1,2-a]pyridin-2-amine

Compound 7 (3.098 g, 8.394 mmol) and lithium hydroxide monohydrate (1.057 g, 25.181 mmol) in water (15 mL)/ethanol (30 mL) was mixed at the room temperature and then heated at 140° C. under the microwaves for 30 min, cooled down to the room temperature, and concentrated under the reduced pressure. The residue was diluted with aqueous saturated ammonium chloride solution (20 mL) and stirred at the ambient temperature. The resulting precipitates were collected by filtration, washed by water, and dried to give Compound 8 as light yellow solid (1.400 g, 61.1%).

Step 4) (1S,2S)-2-fluoro-N-(6-iodo-3-methylimidazo[1,2-a]pyridin-2-yl)cyclopropane-1-carboxamide A mixture of Compound 8 (1.400 g, 5.127 mmol), (1S,2S)-2-fluorocyclopropane-1-carboxylic acid (0.640 g, 6.152 mmol) and 1-[bis (dimethylamino)methylene]-1H-1,2,3-triazolo[4,5-b]pyridinium 3-oxide hexafluorophosphate (HATU, 2.924 g, 7.690 mmol) in N,N-dimethylformamide (20 mL) was treated at the room temperature with N,N-diisopropylethylamine (2.679 mL, 15.380 mmol), stirred at 60° C. for 48 hr, cooled down to the room temperature, and concentrated under the reduced pressure. The residue was diluted with water (100 mL) and stirred at the ambient temperature. The resulting precipitates were collected by filtration, washed by water, and dried to give the crude product which was re-dissolved in ethyl acetate (50 mL) and stirred at the ambient temperature. The resulting precipitates were collected by filtration, washed by ethyl acetate, and dried to give Compound 9 as white solid (1.070 g, 58.1%).

1H NMR (400 MHz, DMSO-d6) δ 10.24 (s, 1H), 8.51 (s, 1H), 7.36 (dd, J=9.2, 1.6 Hz, 1H), 7.27 (d, J=9.2 Hz, 1H), 4.97~4.80 (m, 1H), 2.25 (s, 3H), 2.03 (m, 1H), 1.60~1.53 (m, 1H), 1.11~1.06 (m, 1H).

Step 5) (1S,2S)-2-fluoro-N-(3-methyl-6-(4-methylpyridin-3-yl)imidazo[1,2-a]pyridin-2-yl)cyclopropane-1-carboxamide Compound 9 (0.200 g, 0.557 mmol), (4-methylpyridin-3-yl)boronic acid (0.099 g, 0.724 mmol), [1,1'-bis(diphenylphosphino)ferrocene]dichloropalladium(II) (Pd(dppf)Cl₂, 0.041 g, 0.056 mmol) and potassium carbonate (0.231 g, 1.671 mmol) in water (3 mL)/tetrahydrofuran (12 mL) was mixed at the room temperature and then heated at 120° C. under the microwaves for 1 hr, cooled down to the room temperature, and partitioned between ethyl acetate and water. The organic layer was washed with aqueous saturated sodium chloride solution, separated, dried (anhydrous MgSO$_4$), filtered, and concentrated in vacuo. The residue was chromatographed (SiO$_2$, 10 g cartridge; tetrahydrofuran/ethyl acetate=0% to 10%) to give the crude product which was dissolved in diethylether (5 mL) and hexane (20 mL) and stirred at the ambient temperature. The resulting precipitates were collected by filtration, washed by hexane, and dried to give Example 5 as beige solid (0.100 g, 55.4%).

1H NMR (400 MHz, DMSO-d6) δ 10.25 (s, 1H), 8.47 (s, 1H), 8.44 (d, J=5.2 Hz, 1H), 8.26 (s, 1H), 7.51 (d, J=9.2 Hz, 1H), 7.34 (d, J=5.2 Hz, 1H), 7.24 (d, J=9.2 Hz, 1H), 4.99~4.81 (m, 1H), 2.29 (s, 6H), 2.07~2.03 (m, 1H), 1.63~1.56 (m, 1H), 1.15~1.05 (m, 1H).

Synthetic Method D

Example 29. (1S,2S)-2-fluoro-N-(6-(2-methyl-5-(1H-pyrazol-3-yl)phenyl)imidazo[1,2-a]pyridin-2-yl)cyclopropane-1-carboxamide

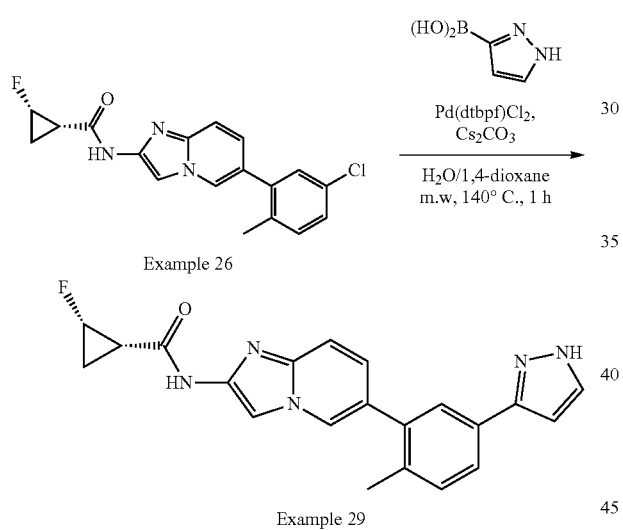

Step 1) (1S,2S)-2-fluoro-N-(6-(2-methyl-5-(1H-pyrazol-3-yl)phenyl)imidazo[1,2-a]pyridin-2-yl)cyclopropane-1-carboxamide Example 26 (0.100 g, 0.291 mmol), (1H-pyrazol-3-yl)boronic acid (0.042 g, 0.378 mmol), [1,1'-bis(di-tert-butylphosphino)ferrocene]palladium(II) dichloride (Pd(dtbpf)Cl$_2$, 0.019 g, 0.029 mmol) and cesium carbonate (0.284 g, 0.873 mmol) in 1,4-dioxane (12 mL)/water (3 mL) was mixed at the room temperature and then heated at 140° C. under the microwaves for 1 hr, cooled down to the room temperature, and partitioned between ethyl acetate and water. The organic layer was washed with aqueous saturated sodium chloride solution, separated, dried (anhydrous MgSO$_4$), filtered, and concentrated in vacuo. The residue was chromatographed (SiO$_2$, 10 g cartridge; tetrahydrofuran/ethyl acetate=0% to 20%) to give the crude product which was dissolved in dichloromethane (3 mL) and hexane (20 mL) and stirred at the ambient temperature. The resulting precipitates were collected by filtration, washed by diethylether, and dried to give Example 29 as beige solid (0.005 g, 4.6%).

1H NMR (400 MHz, DMSO-d6) δ 12.82 (s, 1H), 10.99 (s, 1H), 8.58 (s, 1H), 8.08 (s, 1H), 7.73~7.69 (m, 2H), 7.46~7.23 (m, 4H), 6.70 (s, 1H), 4.97~4.80 (m, 1H), 2.25 (s, 3H), 2.14~2.09 (m, 1H), 1.66~1.59 (m, 1H), 1.13~1.08 (m, 1H).

Synthetic Method E

Example 34. (1S,2S)-2-fluoro-N-(3-fluoro-6-(3-fluoro-2-methylphenyl)imidazo[1,2-a]pyridin-2-yl)cyclopropanecarboxamide

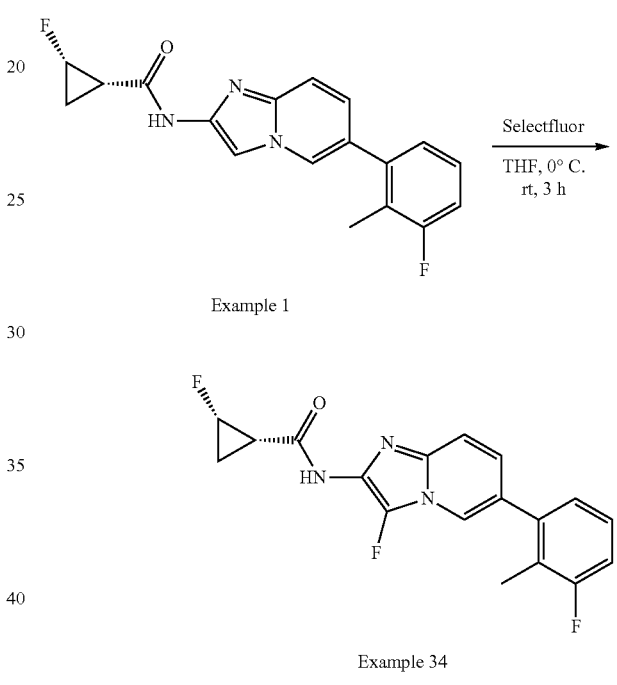

Step 1) (1S,2S)-2-fluoro-N-(3-fluoro-6-(3-fluoro-2-methylphenyl)imidazo[1,2-a]pyridin-2-yl)cyclopropanecarboxamide A solution of Example 1 (0.1 g, 0.3055 mmol) in tetrahydrofuran (4 mL) was mixed at 0° C. with 1-(chloromethyl)-4-fluoro-1,4-diazoniabicyclo[2.2.2]octane ditetrafluoroborate (Selectfluor®, 0.162 g, 0.4582 mmol), stirred at the room temperature for 3 hr, and partitioned between dichloromethane and saturated aqueous sodium bicarbonate solution. The organic layer was washed with aqueous saturated sodium chloride solution, separated, dried (anhydrous Na$_2$SO$_4$), filtered, and concentrated in vacuo. The residue was chromatographed (SiO$_2$, 12 g cartridge; ethyl acetate/hexane=0% to 30%) to give Example 34 as yellow solid (0.021 g, 15%).

1H NMR (400 MHz, DMSO-d6) δ 10.56 (s, 1H), 8.23 (s, 1H), 7.49 (d, J=9.6 Hz, 1H), 7.33~7.27 (m, 1H), 7.24~7.16 (m, 3H), 5.01~4.81 (m, 1H), 2.15 (s, 3H), 2.05~2.05 (m, 1H), 1.63~1.56 (m, 1H), 1.17~1.09 (m, 1H).

Synthetic Method F

Example 41. (1S,2S)-2-fluoro-N-(6-(2-methyl-5-(1H-pyrrol-3-yl)phenyl)imidazo[1,2-a]pyridin-2-yl)cyclopropane-1-carboxamide

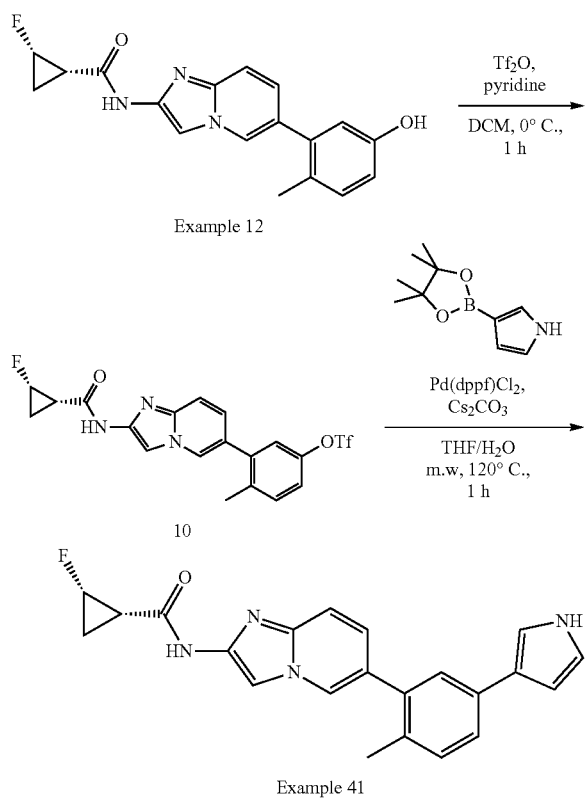

Step 1) 3-(2-((1S,2S)-2-fluorocyclopropane-1-carboxamido)imidazo[1,2-a]pyridin-6-yl)-4-methylphenyl Trifluoromethanesulfonate A mixture of Example 12 (0.842 g, 2.588 mmol) and pyridine (0.313 mL, 3.882 mmol) in dichloromethane (100 mL) was treated at 0° C. with Trifluoromethanesulfonic anhydride (0.479 mL, 2.847 mmol), stirred at the same temperature for 1 hr, and partitioned between dichloromethane and saturated aqueous sodium bicarbonate solution. The organic layer was washed with aqueous saturated sodium chloride solution, separated, dried (anhydrous MgSO₄), filtered, and concentrated in vacuo. The residue was chromatographed (SiO₂, 10 g cartridge; ethyl acetate/hexane=80% to 100%) to give Compound 10 as purple solid (0.056 g, 4.7%).

Step 2) (1S,2S)-2-fluoro-N-(6-(2-methyl-5-(1H-pyrrol-3-yl)phenyl)imidazo[1,2-a]pyridin-2-yl)cyclopropane-1-carboxamide Compound 10 (0.056 g, 0.122 mmol), 3-(4,4,5,5-tetramethyl-1,3,2-dioxaborolan-2-yl)-1H-pyrrole (0.031 g, 0.159 mmol), [1,1'-bis(diphenylphosphino) ferrocene]dichloropalladium(II) (Pd(dppf)Cl₂, 0.009 g, 0.012 mmol) and potassium carbonate (0.051 g, 0.367 mmol) in water (3 mL)/tetrahydrofuran (12 mL) was mixed at the room temperature and then heated at 120° C. under the microwaves for 30 min, cooled down to the room temperature, and partitioned between ethyl acetate and water. The organic layer was washed with aqueous saturated sodium chloride solution, separated, dried (anhydrous MgSO₄), filtered, and concentrated in vacuo. The residue was chromatographed (SiO₂, 10 g cartridge; tetrahydrofuran/ethyl acetate=0% to 10%) to give the crude product which was dissolved in diethylether (5 mL) and hexane (5 mL) and stirred at the ambient temperature. The resulting precipitates were collected by filtration, washed by diethylether, and dried to give Example 41 as white solid (0.005 g, 10.9%).

1H NMR (400 MHz, DMSO-d6) δ 10.97 (s, 1H), 10.86 (bs, 1H), 8.54 (s, 1H), 8.07 (s, 1H), 7.44~7.40 (m, 3H), 7.23~7.19 (m, 3H), 6.74 (dd, J=4.4, 2.8 Hz, 1H), 6.41 (dd, J=4.4, 2.8 Hz, 1H), 4.97~4.79 (m, 1H), 2.20 (s, 3H), 2.11 (m, 1H), 1.66~1.59 (m, 1H), 1.15~1.10 (m, 1H).

Synthetic Method G

Example 44. (1S,2S)-2-fluoro-N-(6-(4-fluoro-5-hydroxy-2-methylphenyl)imidazo[1,2-a]pyridin-2-yl)cyclopropanecarboxamide

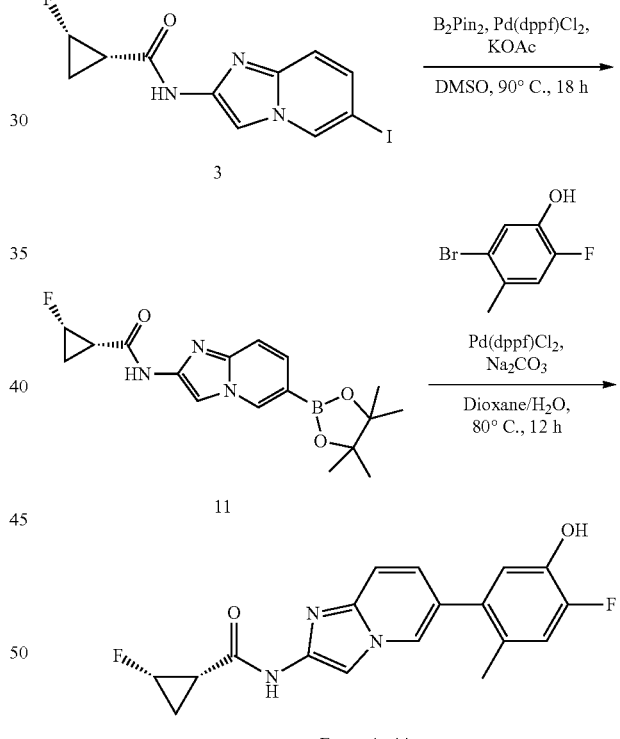

Step 1) (1S,2S)-2-fluoro-N-(6-(4,4,5,5-tetramethyl-1,3,2-dioxaborolan-2-yl)imidazo[1,2-a]pyridin-2-yl)cyclopropane-1-carboxamide Compound 3 (0.800 g, 2.318 mmol), 4,4,4',4',5,5,5',5'-octamethyl-2,2'-bi(1,3,2-dioxaborolane, 1.177 g, 4.636 mmol), [1,1'-bis(diphenylphosphino)ferrocene]dichloropalladium(II) (Pd(dppf)Cl₂, 0.169 g, 0.231 mmol) and potassium acetate (0.796 g, 8.113 mmol) were mixed at the room temperature in DMSO (20 mL) and then stirred at 90° C. for 24 hr, cooled down to the room temperature, filtered through a celite pad to remove solids, and partitioned between ethyl acetate and water. The organic layer was washed with aqueous saturated sodium chloride solution, separated, dried with anhydrous MgSO₄, filtered, and concentrated in vacuo. The residue was chromatographed (SiO2, 12 g cartridge; ethyl acetate/hexane=0% to 100%) to give Compound 11 as brown solid (0.560 g, 69.9%).

Step 2) (1S,2S)-2-fluoro-N-(6-(4-fluoro-5-hydroxy-2-methylphenyl) imidazo[1,2-a]pyridin-2-yl)cyclopropanecarboxamide Compound 11 (0.080 g, 0.231 mmol), 5-bromo-2-fluoro-4-methylphenol (0.056 g, 0.277 mmol), [1,1'-bis(diphenylphosphino)ferrocene]dichloropalladium(II) (Pd(dppf)Cl₂, 0.017 g, 0.023 mmol) and Na₂CO₃ (0.049 g, 0.462 mmol) in dioxane (2 mL)/water (0.5 mL) was mixed at the room temperature and then the mixture was degassed and purged with N₂ for 1 minutes, after then the mixture was stirred at 80° C. for 12 hours under N₂ atmosphere. The reaction mixture was concentrated to give a residue. The residue was purified. The residue was chromatographed (SiO₂, 12 g cartridge; ethyl acetate/hexane=80% to 100%) to give Example 44 as white solid (0.031 g, 39.8%).

1H NMR (400 MHz, DMSO-d6) δ 10.98 (s, 1H), 9.75 (bs, 1H), 8.47 (s, 1H), 8.05 (s, 1H), 7.40 (d, J=9.2 Hz, 1H), 7.13 (dd, J=9.2, 2.0 Hz, 1H), 7.06 (d, J=12.4 Hz, 1H), 6.81 (d, J=9.2 Hz, 1H), 4.98~4.78 (m, 1H), 2.14~2.07 (m, 4H), 1.65~1.58 (m, 1H), 1.16~1.07 (m, 1H).

Synthetic Method H

Example 66. (1S,2S)-2-fluoro-N-(6-(3-fluoro-2-(methoxymethyl)phenyl) imidazo[1,2-a]pyridin-2-yl)cyclopropanecarboxamide

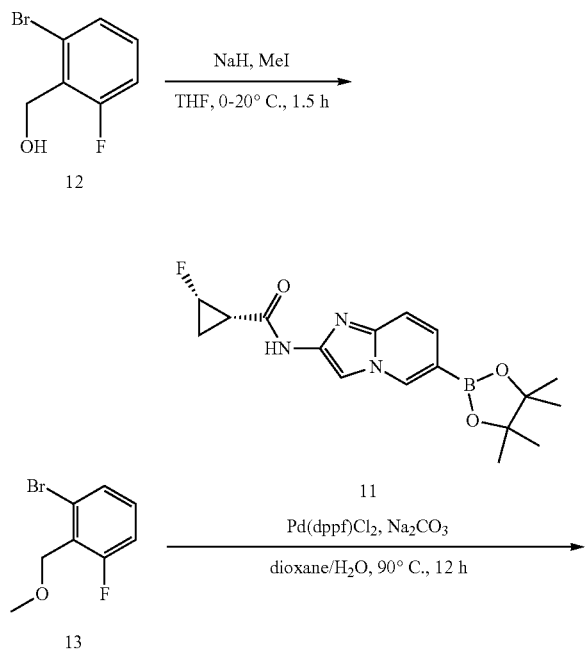

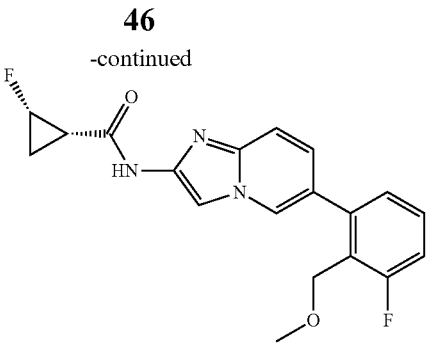

Example 66

Step 1)
1-bromo-3-fluoro-2-(methoxymethyl)benzene

To a solution of Compound 12 (500 mg, 2.44 mmol, 1 eq) in THF (10 mL) was added NaH (146.31 mg, 3.66 mmol, 60% purity, 1.5 eq) in portions at 0° C. under N₂, and reaction mixture was stirred at 0° C. for 0.5 hour under N₂, after then MeI (692.30 mg, 4.88 mmol, 303.64 μL, 2 eq) was added dropwise, then the mixture was stirred at 20° C. for another 1 hour under N₂. Saturated aqueous solution of NH₄Cl (30 mL) was added into the reaction mixture, then the mixture was extracted with ethyl acetate (20 mL*2), the combined organic layers were dried over Na₂SO₄, filtered and concentrated under reduced pressure to give a residue. Compound 13 (510 mg, crude) was obtained as a yellow oil.

1H NMR (400 MHz, CDCl₃) δ 7.41 (d, J=8.1 Hz, 1H), 7.18 (dt, J=5.9, 8.2 Hz, 1H), 7.10-7.00 (m, 1H), 4.64 (d, J=2.3 Hz, 2H), 3.42 (s, 3H).

Step 2) (1S,2S)-2-fluoro-N-(6-(3-fluoro-2-(methoxymethyl)phenyl) imidazo[1,2-a]pyridin-2-yl)cyclopropanecarboxamide To a solution of Compound 13 (80 mg, 365.21 μmol, 1 eq) and Compound 11 (151.27 mg, 438.25 μmol, 1.2 eq) in dioxane (2 mL) and H₂O (0.4 mL) were added Pd(dppf)Cl₂ (26.72 mg, 36.52 μmol, 0.1 eq) and Na₂CO₃ (77.42 mg, 730.42 μmol, 2 eq), then the mixture was stirred at 90° C. for 12 hours under N₂. The reaction mixture was diluted with ethyl acetate (300 mL), then the mixture was filtered with silica gel, and the filtrate was concentrated to give a residue. The residue was purified by prep-HPLC (column: Phenomenex luna C18 150*40 mm*15 um; mobile phase: [water (0.1% TFA)-ACN]; B %: 17%-47%, 10 min). Example 66 (91.3 mg, 193.69 μmol, 53.03% yield, 100% purity, TFA) was obtained as a white solid.

1H NMR (400 MHz, DMSO-d6) δ 11.25 (s, 1H), 8.68 (s, 1H), 8.14 (s, 1H), 7.60 (d, J=9.2 Hz, 1H), 7.52 (dt, J=6.0, 7.9 Hz, 1H), 7.44 (dd, J=1.6, 9.2 Hz, 1H), 7.33 (d, J=8.7 Hz, 1H), 7.30-7.25 (m, 1H), 5.11-4.76 (m, 1H), 4.30 (br d, J=1.3 Hz, 2H), 3.25 (s, 3H), 2.23-2.08 (m, 1H), 1.76-1.59 (m, 1H), 1.20 (tdd, J=6.3, 9.1, 12.4 Hz, 1H).

Synthetic Method I

Example 67. (1S,2S)-2-fluoro-N-(6-(3-fluoro-2-(furan-2-yl)phenyl)imidazo [1,2-a]pyridin-2-yl)cyclopropanecarboxamide

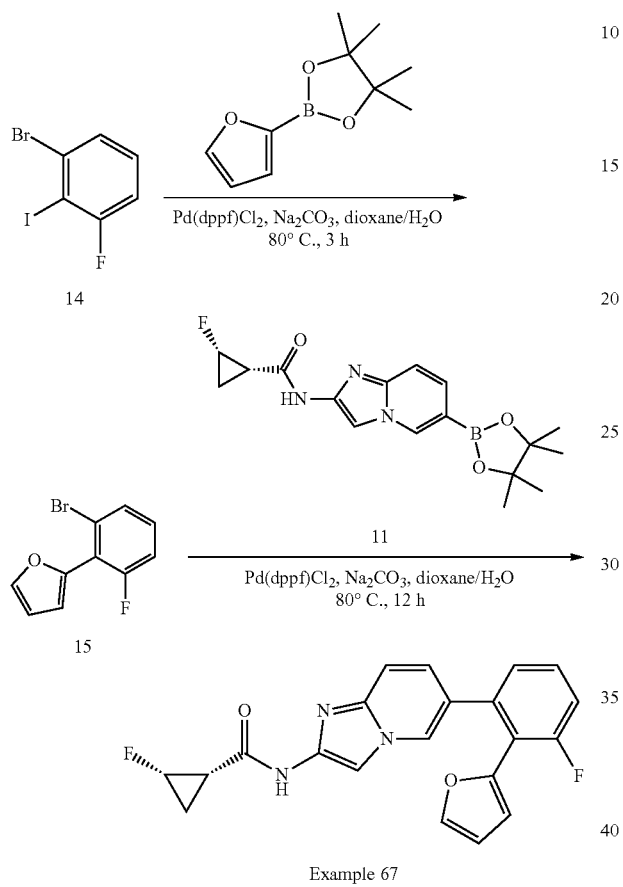

Example 67

Step 1) 2-(2-bromo-6-fluorophenyl)furan

To a solution of Compound 14 (511.74 mg, 1.70 mmol, 1.1 eq) and 2-(furan-2-yl)-4,4,5,5-tetramethyl-1,3,2-dioxaborolane (300 mg, 1.55 mmol, 1 eq) in dioxane (3 mL) and H$_2$O (0.6 mL) were added Pd(dppf)Cl$_2$ (113.13 mg, 154.61 μmol, 0.1 eq) and Na$_2$CO$_3$ (491.61 mg, 4.64 mmol, 3 eq), then the reaction mixture was stirred at 80° C. for 3 hr under N$_2$. The reaction mixture was poured into water (50 mL), then the mixture was extracted with ethyl acetate (50 mL*2), the combined organic layers were dried over Na$_2$SO$_4$, filtered and concentrated under reduced pressure to give a residue. The residue was purified by prep-TLC (SiO$_2$, Petroleum ether:Ethyl acetate=3:1). The residue was purified by prep-TLC (SiO$_2$, Petroleum ether:Ethyl acetate=1:0). Compound 15 (70 mg, 290.39 μmol, 18.78% yield) was obtained as a yellow oil.

1H NMR (400 MHz, CDCl$_3$) δ 7.61 (dd, J=0.8, 1.8 Hz, 1H), 7.48 (td, J=1.1, 8.0 Hz, 1H), 7.21 (dt, J=5.8, 8.1 Hz, 1H), 7.15-7.08 (m, 1H), 6.70 (td, J=0.9, 3.3 Hz, 1H), 6.56 (dd, J=1.8, 3.3 Hz, 1H).

Step 2) (1S,2S)-2-fluoro-N-(6-(3-fluoro-2-(furan-2-yl)phenyl)imidazo[1,2-a]pyridin-2-yl)cyclopropanecarboxamide To a solution of Compound 15 (70 mg, 290.39 μmol, 1 eq) and Compound 11 (110.26 mg, 319.43 μmol, 1.1 eq) in dioxane (1 mL) and H$_2$O (0.2 mL) were added Pd(dppf)Cl$_2$ (21.25 mg, 29.04 μmol, 0.1 eq) and Na$_2$CO$_3$ (92.33 mg, 871.17 μmol, 3 eq), then the reaction mixture was stirred at 80° C. for 12 hr under N$_2$. The reaction mixture was poured into brine (10 mL), then the mixture was extracted with ethyl acetate (10 mL*2), the combined organic layers were dried over Na$_2$SO$_4$, filtered and concentrated under reduced pressure to give a residue. The residue was dissolved with methanol:dichloromethane (1:10, 100 mL), then the mixture was filtered with silica gel, and the filtrate was concentrated to give a residue. The residue was purified by prep-HPLC (column: Phenomenex Synergi C18 150*25*10 um; mobile phase: [water (0.1% TFA)-ACN]; B %: 34%-54%, 9 min). Example 67 (38.3 mg, 77.63 μmol, 26.73% yield, 100% purity, TFA) was obtained as a white solid.

1H NMR (400 MHz, DMSO-d6) δ 11.20 (s, 1H), 8.61 (s, 1H), 8.08 (s, 1H), 7.61 (dd, J=0.9, 1.6 Hz, 1H), 7.60-7.54 (m, 1H), 7.45-7.41 (m, 1H), 7.40-7.36 (m, 2H), 6.93 (dd, J=1.3, 9.3 Hz, 1H), 6.56-6.48 (m, 2H), 5.05-4.83 (m, 1H), 2.19-2.09 (m, 1H), 1.75-1.59 (m, 1H), 1.19 (tdd, J=6.3, 9.1, 12.4 Hz, 1H).

Synthetic Method J

Example 72. N-(6-(3-fluoro-2-methylphenyl)imidazo[1,2-a]pyridin-2-yl)cyclopropanecarboxamide

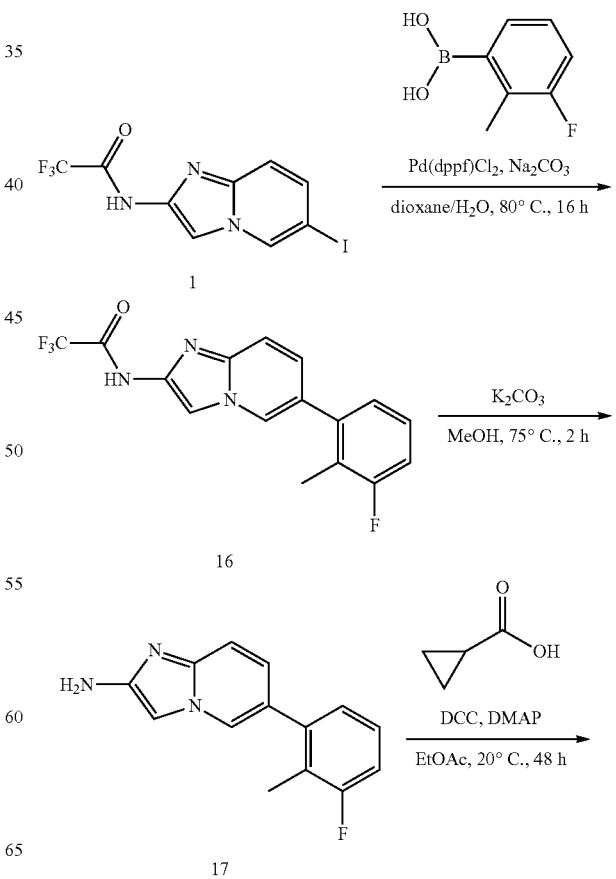

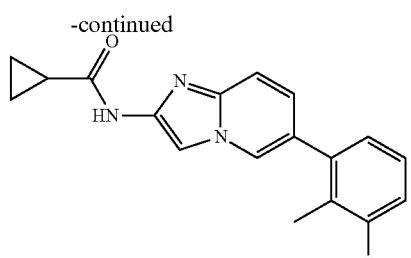

Example 72

Step 1) 2,2,2-trifluoro-N-(6-(3-fluoro-2-methylphenyl)imidazo[1,2-a]pyridin-2-yl)acetamide To a solution of Compound 1 (1 g, 2.82 mmol, 1 eq) in dioxane (10 mL) and H₂O (1 mL) was added Compound 2 (520.30 mg, 3.38 mmol, 1.2 eq), Pd(dppf)Cl₂ (206.08 mg, 281.65 μmol, 0.1 eq) and Na₂CO₃ (298.52 mg, 2.82 mmol, 1 eq). The mixture was stirred at 80° C. for 16 hr under N₂ atmosphere. The reaction mixture diluted with water 30 mL and extracted with Ethyl acetate (30 mL*2). The combined organic layers were washed with brine (30 mL*2), dried over Na₂SO₄, filtered and the filtrate was concentrated under reduced pressure to give a residue. The residue was purified by column chromatography (Silica gel, Petroleum ether: Ethyl acetate=20:1 to 5:1). Compound 16 (500 mg, 1.48 mmol, 52.64% yield) was obtained as a white solid.

Step 2) 6-(3-fluoro-2-methylphenyl)imidazo[1,2-a]pyridin-2-amine

To a solution of Compound 16 (500 mg, 1.48 mmol, 1 eq) in MeOH (10 mL) and H₂O (10 mL) was added K₂CO₃ (1.02 g, 7.41 mmol, 5 eq). The mixture was stirred at 75° C. for 2 hr. The reaction mixture was added with water 50 mL, and extracted with Ethyl acetate (50 mL*2). The combined organic layers were washed with brine (50 mL*2), dried over Na₂SO₄, filtered and the filtrate was concentrated under reduced pressure to give a residue. Compound 17 (300 mg, 1.24 mmol, 83.88% yield) was obtained as a yellow solid

Step 3) N-(6-(3-fluoro-2-methylphenyl)imidazo[1,2-a]pyridin-2-yl)cyclopropanecarboxamide To a solution of Compound 17 (100 mg, 414.49 μmol, 1 eq) in EtOAc (2 mL) was added cyclopropanecarboxylic acid (53.52 mg, 621.73 μmol, 49.10 μL, 1.5 eq) and DCC (85.52 mg, 414.49 μmol, 83.84 μL, 1 eq). The mixture was stirred at 20° C. for 32 hr. Then DMAP (5.06 mg, 41.45 μmol, 0.1 eq) was added to the mixture and stirred at 20° C. for 16 hr. The reaction mixture was diluted with water 20 mL and extracted with Ethyl acetate (20 mL*2). The combined organic layers were washed with brine (20 mL*2), dried over Na2SO4, filtered and the filtrate was concentrated under reduced pressure to give a residue. The residue was purified by prep-HPLC (column: Phenomenex Luna C18 150*25 mm*10 um; mobile phase: [water (0.1% TFA)-ACN]; B %: 22%-52%, 10 min). Example 72 (45.9 mg, 106.25 μmol, 25.63% yield, 98% purity, TFA) was obtained as a pink solid.

1H NMR (400 MHz, DMSO-d6) δ 11.22 (br s, 1H), 8.66 (s, 1H), 8.09 (s, 1H), 7.59 (d, J=9.2 Hz, 1H), 7.40 (br d, J=9.3 Hz, 1H), 7.38-7.30 (m, 1H), 7.28-7.21 (m, 1H), 7.17 (d, J=7.5 Hz, 1H), 2.18 (d, J=2.3 Hz, 3H), 1.94 (quin, J=6.2 Hz, 1H), 0.85 (d, J=6.1 Hz, 4H).

Synthetic Method K

Example 77. (1S,2S)—N-(6-(2-(acetamidomethyl)-3-fluorophenyl)imidazo[1,2-a]pyridin-2-yl)-2-fluorocyclopropanecarboxamide

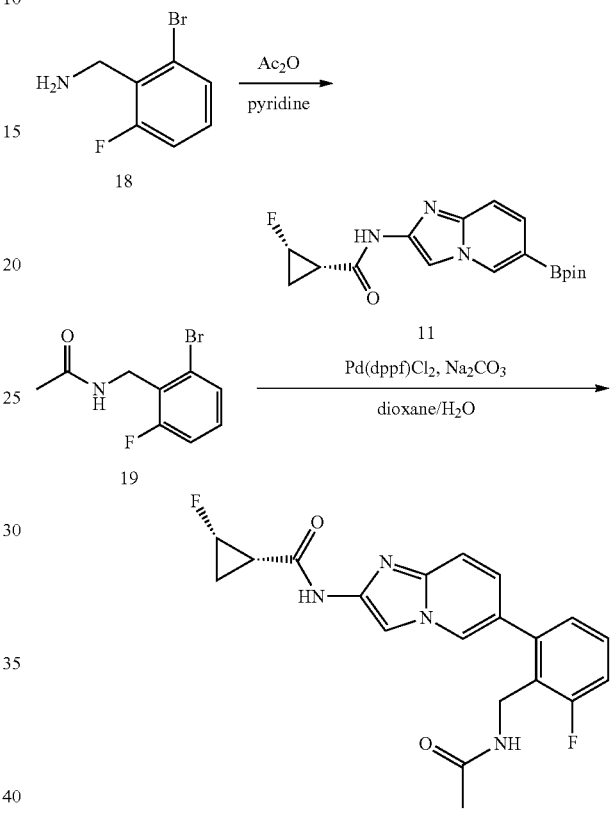

Example 77

Step 1) N-(2-bromo-6-fluorobenzyl)acetamide

To a solution of Compound 18 (200 mg, 695.94 μmol, 1 eq) in Py (5 mL) was added Ac2O (85.26 mg, 835.13 μmol, 78.22 μL, 1.2 eq). The mixture was stirred at 25° C. for 3 hr. Desired MS was detected by LC-MS. The mixture was concentrated under reduced pressure to give a residue. The residue was adjusted to pH=6 with HCl, and extracted with EA (30 mL*3). The organic phase was concentrated under reduced pressure to give a residue. Compound 19 (130 mg, 412.07 μmol, 59.21% yield, 78% purity) was obtained as light yellow solid.

Step 2) (1S,2S)—N-(6-(2-(acetamidomethyl)-3-fluorophenyl)imidazo[1,2-a]pyridin-2-yl)-2-fluorocyclopropanecarboxamide A mixture of Compound 19 (100 mg, 361.68 μmol, 1 eq), Compound 11 (122.35 mg, 354.44 μmol, 0.98 eq), Pd(dppf)Cl₂ (26.46 mg, 36.17 μmol, 0.1 eq) and Na₂CO₃ (76.67 mg, 723.35 μmol, 2 eq) in Water (1 mL) and dioxane (4 mL) was degassed and purged with N₂ for 3 times, and then the mixture was stirred at 80° C. for 16 hr under N₂ atmosphere.

Desired MS was detected by LC-MS. The mixture was filtered, and the filtrate was concentrated under reduced pressure to give a residue. The residue was purified by prep-HPLC (column: Phenomenex luna C18 250*50 mm*10 um; mobile phase: [water (0.1% TFA)-ACN]; B %: 10%-40%, 9 min). Example 77 (15.3 mg, 29.84 μmol, 8.25% yield, 97.2% purity, TFA) was obtained as white solid 1H NMR (400 MHz, CD3OD) δ 8.67 (s, 1H), 7.81-7.71 (m, 2H), 7.49-7.47 (m, 1H), 7.31-7.22 (m, 2H), 5.04-5.01 (m, 0.5H), 4.87-4.85 (m, 0.5H), 4.38 (s, 2H), 2.16-2.12 (m, 1H), 1.90-1.84 (m, 1H), 1.31-1.28 (m, 1H).

Synthetic Method L

Example 84. (1S,2S)-2-fluoro-N-(6-(3-fluoro-2-((2-methoxyethoxy)methyl) phenyl)imidazo[1,2-a]pyridin-2-yl)cyclopropanecarboxamide. TFA Salt

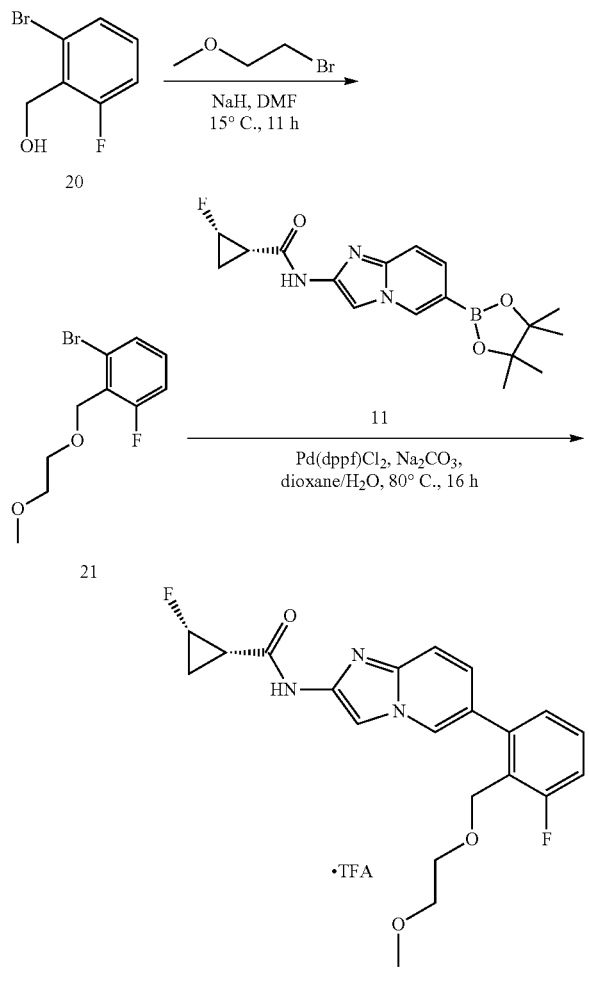

Example 84

Step 1) 1-bromo-3-fluoro-2-((2-methoxyethoxy)methyl)benzene

Compound 20 (445.00 mg, 2.17 mmol, 1 eq) was dissolved in DMF (15 mL), to which NaH (130.22 mg, 3.26 mmol, 60% purity, 1.5 eq) was added at 0° C. in portions. The resulting mixture was then stirred under N₂ atmosphere for 30 min, before 1-bromo-2-methoxy-ethane (362.01 mg, 2.60 mmol, 244.60 μL, 1.2 eq) was added at 0° C. The mixture was then stirred under N₂ atmosphere at 15° C. for another 11.5 hr. The mixture was quenched with EtOH (5 mL), diluted with water (20 mL) and extracted with EA (20 mL×3). The combined organic layers were concentrated under reduced pressure. The residue was purified by silica gel chromatography (pure PE to PE/EA=4/1) to afford Compound 21 (178 mg, 676.54 μmol, 31.17% yield) as a light yellow oil.

Step 2) (1S,2S)-2-fluoro-N-(6-(3-fluoro-2-((2-methoxyethoxy)methyl)phenyl) imidazo[1,2-a]pyridin-2-yl)cyclopropanecarboxamide. TFA Salt The mixture of Compound 21 (178 mg, 676.54 μmol, 1 eq) and Compound 11 (210.17 mg, 608.89 μmol, 0.9 eq) was dissolved in dioxane (10 mL) and H₂O (2 mL), to which Pd(dppf)Cl₂ (99.01 mg, 135.31 μmol, 0.2 eq) and Na₂CO₃ (215.12 mg, 2.03 mmol, 3 eq) were added in portions. The resulting mixture was then stirred under N₂ atmosphere at 80° C. for 16 hr. Desired m/z was detected by LC-MS. The mixture was filtered and the filtrate was diluted with water (20 mL) and extracted with EA (20 mL×3). The combined organic layers were concentrated under reduced pressure. The residue was purified by silica gel chromatography (PE/EA=10/1 to 1/1) and then Prep-HPLC (column: Phenomenex Gemini-NX C18 75*30 mm*3 um; mobile phase: [water (0.1% TFA)-ACN]; B %: 18%-48%, 7 min) and lyophilized to afford Example 84 (32.2 mg, 62.10 μmol, 9.18% yield, 99.4% purity, TFA) as an off-white solid.

1H NMR (400 MHz, DMSO) δ 11.23-11.19 (br s, 1H), 8.72 (s, 1H), 8.10 (s, 1H), 7.56-7.50 (m, 3H), 7.32-7.28 (m, 2H), 5.04-4.84 (m, 1H), 4.35 (s, 2H), 3.47-3.44 (m, 4H), 3.25 (s, 3H), 2.16-2.11 (m, 1H), 1.70-1.64 (m, 1H), 1.21-1.16 (m, 1H).

Synthetic Method M

Example 85. (1S,2S)-2-fluoro-N-(6-(3-fluoro-2-((2-hydroxyethoxy)methyl) phenyl)imidazo[1,2-a]pyridin-2-yl)cyclopropanecarboxamide

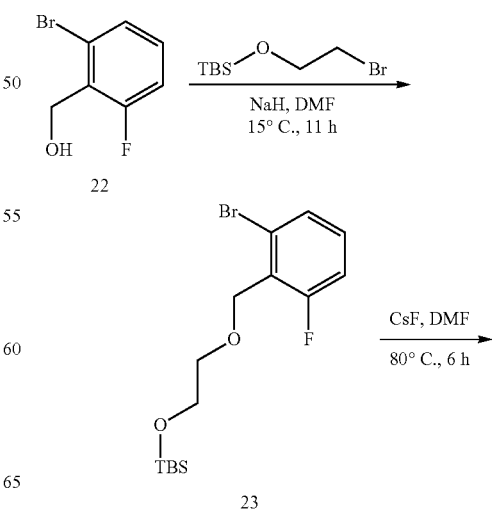

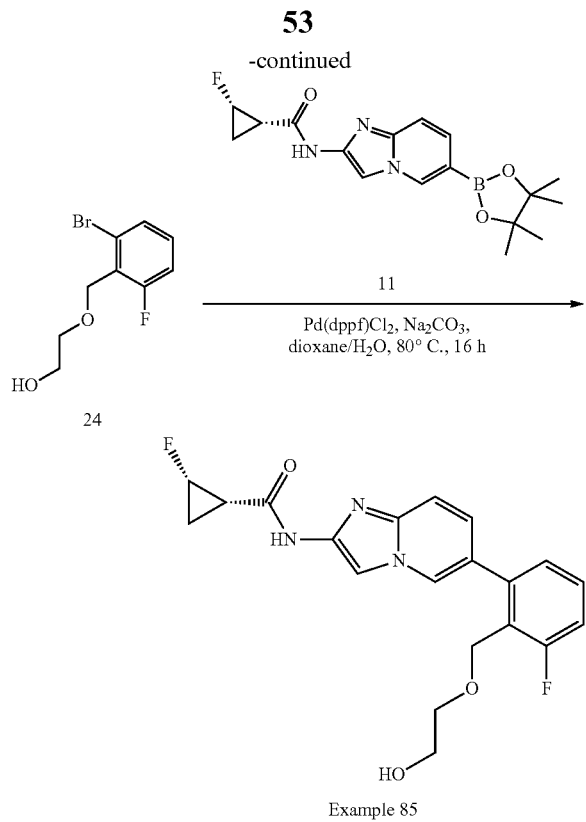

Example 85

Step 1) (2-((2-bromo-6-fluorobenzyl)oxy)ethoxy)(tert-butyl)dimethylsilane

Compound 22 (1 g, 4.88 mmol, 1 eq) was dissolved in DMF (50 mL), NaH (292.65 mg, 7.32 mmol, 60% purity, 1.5 eq) was added at 0° C. in portions. The resulting mixture was then stirred under $N_2$ atmosphere for 30 min, before 2-bromoethoxy-tert-butyl-dimethyl-silane (1.40 g, 5.85 mmol, 109.93 μL, 1.2 eq) was added at 0° C. The mixture was then stirred under $N_2$ atmosphere at 15° C. for another 11.5 hr. New spots were formed according to the result of TLC (PE/EA=4/1). The mixture was quenched with EtOH (5 mL), diluted with water (20 mL) and extracted with EA (20 mL×3). The combined organic layers were concentrated under reduced pressure. The residue was purified together with the former batch by silica gel chromatography (pure PE to PE/EA=4/1) to afford Compound 23 (372 mg, 1.02 mmol, 20.99% yield) as a white solid.

1H NMR (400 MHz, DMSO-d6) δ 7.52-7.50 (m, 1H), 7.37-7.36 (m, 1H), 7.34-7.30 (m, 1H), 4.61-4.60 (m, 2H), 3.90-3.80 (m, 2H), 3.58-3.47 (m, 2H), 0.835 (s, 9H), 0.02 (s, 6H).

Step 2) 2-((2-bromo-6-fluorobenzyl)oxy)ethanol

Compound 23 (352 mg, 968.80 μmol, 1 eq) was dissolved in DMF (10 mL), CsF (147.16 mg, 968.80 μmol, 35.72 μL, 1 eq) was added. The resulting mixture was then stirred at 80° C. for 12 hr. The starting material was consumed according to the result of TLC (PE/EA=4/1). The mixture was filtered and the filtrate was concentrated under reduced pressure. The residue was purified by silica gel chromatography (PE to PE/EA=5/1) to afford Compound 24 (120 mg, 481.78 μmol, 49.73% yield) as an off-white solid.

1H NMR (400 MHz, DMSO-d6) δ 7.52-7.50 (m, 1H), 7.36-7.28 (m, 2H), 4.60-4.59 (m, 2H), 3.52-3.47 (m, 4H).

Step 3 (1S,2S)-2-fluoro-N-(6-(3-fluoro-2-((2-hydroxyethoxy)methyl)phenyl) imidazo[1,2-a]pyridin-2-yl)cyclopropanecarboxamide The mixture of Compound 24 (120 mg, 481.78 μmol, 1 eq) and Compound 11 (149.67 mg, 433.60 μmol, 0.9 eq) was dissolved in the mixture of dioxane (10 mL) and $H_2O$ (2 mL), Pd(dppf)Cl$_2$ (35.25 mg, 48.18 μmol, 0.1 eq) and Na$_2$CO$_3$ (153.19 mg, 1.45 mmol, 3 eq) were added in portions. The resulting mixture was then stirred under $N_2$ atmosphere at 80° C. for 12 hr. Desired m/z was detected by LC-MS. The mixture was filtered and the filtrate was diluted with water (20 mL) and extracted with EA (20 mL×3). The combined organic layers were concentrated under reduced pressure. The residue was purified by silica gel chromatography (PE/EA=2/1 to EA/MeOH=10/1) and then by Prep-HPLC (column: Phenomenex Gemini-NX C18 75*30 mm*3 um; mobile phase: [water (0.1% TFA)-ACN]; B %: 12%-42%, 9 min) and lyophilized to afford Example 85 (74.1 mg, 143.65 μmol, 29.82% yield, 97.2% purity, TFA) as an off-white solid.

1H NMR (400 MHz, DMSO-d6) δ 11.21 (s, 1H), 8.78 (s, 1H), 8.14 (s, 1H), 7.58-7.47 (m, 3H), 7.33-7.29 (m, 2H), 5.05-4.85 (m, 1H), 4.36 (s, 2H), 3.55-3.52 (m, 2H), 3.47-3.45 (m, 2H), 2.16-2.13 (m, 1H), 1.71-1.69 (m, 1H), 1.65-1.64 (m, 1H).

Synthetic Method N

Example 105. (1S,2S)-2-fluoro-N-(6-(2-methyl-5-(1H-pyrazol-1-yl)phenyl) imidazo[1,2-a]pyridin-2-yl)cyclopropane-1-carboxamide

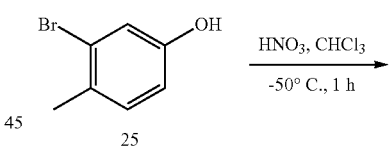

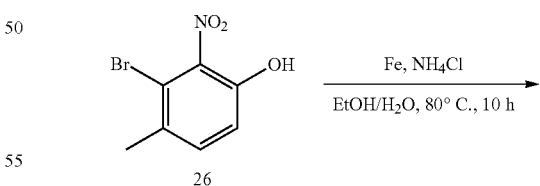

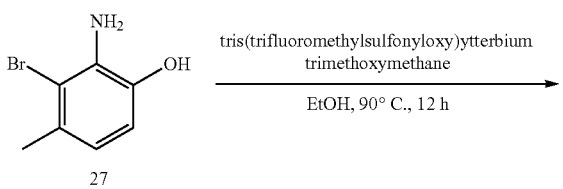

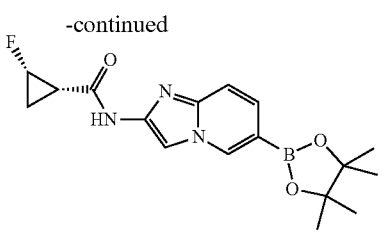

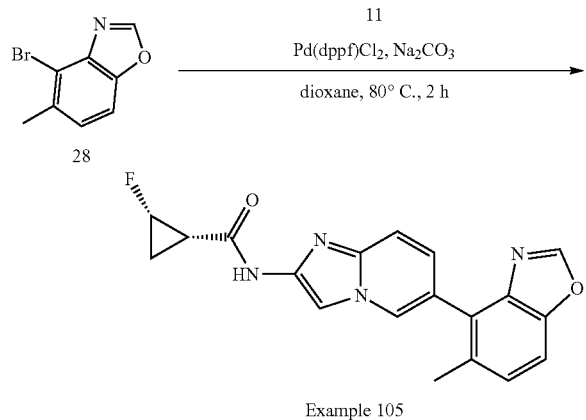

Example 105

Step 1) 3-bromo-4-methyl-2-nitrophenol

To a solution of Compound 25 (5 g, 26.73 mmol, 1 eq) in CHCl₃ (50 mL) was added HNO3 (2.85 g, 29.41 mmol, 2.04 mL, 1.1 eq) dropwise at −50° C., then the reaction mixture was stirred at −50° C. for 1 hr. The reaction mixture was slowly poured into ice water (200 mL), then the mixture was extracted with dichloromethane (100 mL*2), the combined organic layers were dried over Na₂SO₄, filtered and concentrated under reduced pressure to give a residue. The residue was purified by column chromatography (SiO₂, Petroleum ether/Ethyl acetate=1/0 to 100/1). Compound 26 (550 mg, 2.37 mmol, 8.87% yield) was obtained as a yellow oil.

1H NMR (400 MHz, CDCl₃) δ 8.84-8.20 (m, 1H), 7.31 (d, J=8.7 Hz, 1H), 7.00 (d, J=8.6 Hz, 1H), 2.41 (s, 3H).

Step 2) 2-amino-3-bromo-4-methylphenol

To a solution of Compound 26 (450 mg, 1.94 mmol, 1 eq) in EtOH (5 mL) and H₂O (5 mL) were added Fe (649.83 mg, 11.64 mmol, 6 eq) and NH₄Cl (622.44 mg, 11.64 mmol, 6 eq). The suspension was degassed and purged with N₂ for 3 times. The reaction mixture was stirred under N₂ at 80° C. for 2 hours. The reaction mixture was filtered, the filter cake was washed with methanol (50 mL*3) and the filtrate was concentrated under reduced pressure to give a residue. The residue was poured into water (50 mL), then the mixture was extracted with ethyl acetate (50 mL*2), the combined organic layers were dried over Na₂SO₄, filtered and concentrated under reduced pressure to give a residue. The residue was purified by reverse flase (MeCN/H₂O, CF₃COOH), then the mixture was concentrated to remove MeCN, after then the mixture's pH was adjust to pH=7 by using saturated aqueous solution of sodium bicarbonate, then the mixture was extracted with ethyl acetate (100 mL*2), the combined organic layers were dried over saturated sodium sulfate, filtered and concentrated under reduced pressure to give a residue. Compound 27 (210 mg, 1.02 mmol, 52.52% yield, 98% purity) was obtained as a yellow solid.

1H NMR (400 MHz, CDCl₃) δ 6.64-6.59 (m, 1H), 6.54-6.50 (m, 1H), 2.30 (s, 3H).

Step 3) 4-bromo-5-methylbenzo[d]oxazole

To a solution of Compound 27 (210 mg, 1.02 mmol, 1 eq) and trimethoxymethane (162.14 mg, 1.53 mmol, 167.50 μL, 1.5 eq) in EtOH (3 mL) was added tris(trifluoromethylsulfonyloxy)ytterbium (14.19 mg, 22.87 μmol, 2.25e-2 eq), then the reaction mixture was stirred at 90° C. for 12 hr. LCMS showed 19% of Compound 3 was remained and 81% of desired mass was detected. trimethoxymethane (108.09 mg, 1.02 mmol, 111.66 μL, 1 eq) was added to the reaction mixture, then the reaction mixture was stirred at 90° C. for another 2 hr. The reaction mixture was concentrated under reduced pressure to remove solvent. Saturated aqueous solution of NaHCO₃ (50 mL) was added into the residue, then the mixture was extracted with ethyl acetate (30 mL*3), the combined organic layers were dried over Na₂SO₄, filtered and concentrated under reduced pressure to give a residue. Compound 28 (160 mg, crude) was obtained as a brown solid.

1H NMR (400 MHz, CDCl₃) δ 8.12 (s, 1H), 7.43 (d, J=8.3 Hz, 1H), 7.29 (d, J=8.4 Hz, 1H), 2.54 (s, 3H).

Step 4) (1S,2S)-2-fluoro-N-(6-(5-methylbenzo[d]oxazol-4-yl)imidazo[1,2-a]pyridin-2-yl)cyclopropanecarboxamide To a solution of Compound 28 (130 mg, 613.08 μmol, 1 eq) and Compound 11 (253.95 mg, 735.70 μmol, 1.2 eq) in dioxane (2 mL) and H₂O (0.4 mL) were added Pd(dppf)Cl₂ (44.86 mg, 61.31 μmol, 0.1 eq) and Na₂CO₃ (194.94 mg, 1.84 mmol, 3 eq), then the reaction mixture was stirred at 90° C. for 12 hr under N₂. The reaction mixture was poured into brine (30 mL), then the mixture was extracted with ethyl acetate (30 mL*2), the combined organic layers were dried over Na₂SO₄, filtered and concentrated under reduced pressure to give a residue. The residue was dissolved with methanol:dichloromethane (1:10, 100 mL), then the mixture was filtered with silica gel, and the filtrate was concentrated to give a residue. The residue was purified by prep-HPLC (column: Xtimate C18 150*40 mm*10 um; mobile phase: [water (0.05% ammonia hydroxide v/v)-ACN]; B %: 25%-55%, 10 min). Example 105 (118.4 mg, 333.33 μmol, 54.37% yield, 98.633% purity) was obtained as a white solid.

1H NMR (400 MHz, DMSO-d6) δ 11.07 (s, 1H), 8.70 (s, 1H), 8.65 (s, 1H), 8.13 (s, 1H), 7.71 (d, J=8.3 Hz, 1H), 7.53 (d, J=9.2 Hz, 1H), 7.43 (d, J=8.4 Hz, 1H), 7.29 (dd, J=1.6, 9.2 Hz, 1H), 5.05-4.81 (m, 1H), 2.38 (s, 3H), 2.20-2.10 (m, 1H), 1.73-1.59 (m, 1H), 1.17 (tdd, J=6.2, 9.1, 12.2 Hz, 1H).

Table 1 below shows the compounds of Examples along with general synthetic methods used to make the compound and characterization data.

TABLE 1

| Ex # | Structure/Name | 1H NMR/MS (M + 1) | Synthetic Method |
|---|---|---|---|
| 1 | 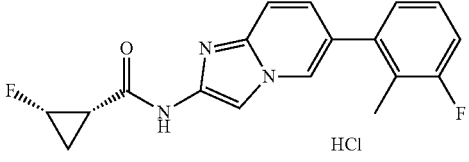<br>(1S,2S)-2-fluoro-N-(6-(3-fluoro-2-methylphenyl)imidazo[1,2-a]pyridin-2-yl)cyclopropane-1-carboxamide. 1 HCl salt | 1H NMR (400 MHz, DMSO-d6) δ 11.67 (s, 1H), 8.74 (s, 1H), 8.13 (s, 1H), 7.69 (d, J = 9.2 Hz, 1H), 7.55 (d, J = 9.2 Hz, 1H), 7.35~7.30 (m, 1H), 7.23 (t, J = 9.2 Hz, 1H), 7.15 (d, J = 7.2 Hz, 1H), 5.05~4.85 (m, 1H), 7.21~7.14 (m, 4H), 1.69~1.63 (m, 1H), 1.21~1.18 (m, 1H); LCMS (electrospray) m/z 327.88 (M + H)+. | A |
| 2 | 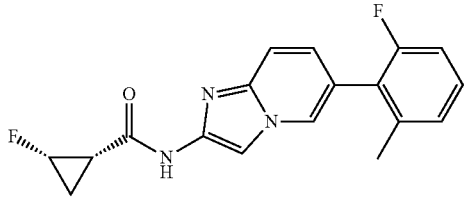<br>(1S,2S)-2-fluoro-N-(6-(2-fluoro-6-methylphenyl)imidazo[1,2-a]pyridin-2-yl)cyclopropane-1-carboxamide | 1H NMR (400 MHz, DMSO-d6) δ 11.00 (s, 1H), 8.53 (s, 1H), 8.06 (s, 1H), 7.46 (d, J = 9.2 Hz, 1H), 7.35~7.29 (m, 1H), 7.17~7.09 (m, 3H), 4.98~4.78 (m, 1H), 2.16~2.09 (m, 4H), 1.66~1.59 (m, 1H), 1.16~1.08 (m, 1H); LCMS (electrospray) m/z 327.96 (M + H)+. | A |
| 3 | 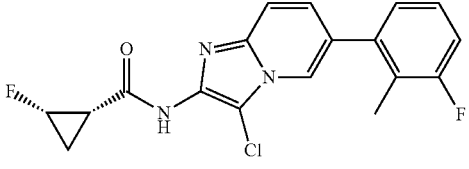<br>(1S,2S)-3-(chloro-6-(3-fluoro-2-methylphenyl)imidazo[1,2-a]pyridin-2-yl)-2-fluorocyclopropane-1-carboxamide | 1H NMR (400 MHz, DMSO-d6); δ 10.44 (s, 1H), 8.21 (s, 1H), 7.62 (d, J = 9.6 Hz, 1H), 7.35 (dd, J = 9.2, 1.6 Hz, 1H), 7.30 (t, J = 7.0 Hz, 1H), 7.24~7.19 (m, 2H), 5.01~4.83 (m, 1H), 2.15 (d, J = 2.4 Hz, 3H), 2.06~2.03 (m, 1H), 1.64~1.56 (m, 1H), 1.15~1.08 (m, 1H); LCMS (electrospray) m/z 361.95 (M + H)+. | B |
| 4 | 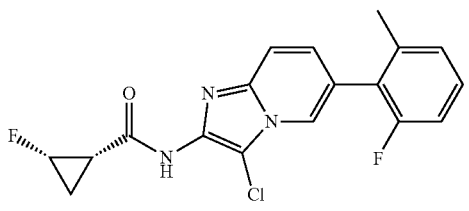<br>(1S,2S)-N-(3-(chloro-6-(2-fluoro-6-methylphenyl)imidazo[1,2-a]pyridin-2-yl)-2-fluorocyclopropane-1-carboxamide | 1H NMR (400 MHz, DMSO-d6); δ 10.46 (s, 1H), 8.27 (s, 1H), 7.64 (d, J = 8.4 Hz, 1H), 7.38~7.33 (m, 1H), 7.27 (d, J = 8.8 Hz, 1H), 7.19~7.12 (m, 2H), 5.01~4.83 (m, 1H), 2.17 (s, 3H), 2.12~2.05 (m, 1H), 1.63~1.56 (m, 1H), 1.20~1.10 (m, 1H); LCMS (electrospray) m/z 361.95 (M + H)+. | B |
| 5 | 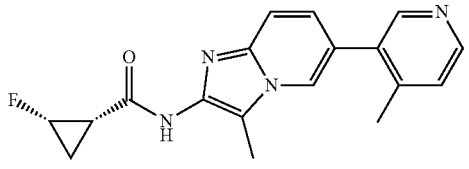<br>(1S,2S)-2-flouro-N-(3-(methyl-6-(4-methylpyridin-3-yl)imidazo[1,2-a]pyridin-2-yl)-2-cyclopropane-1-carboxamide | 1H NMR (400 MHz, DMSO-d6); δ 10.25 (s, 1H), 8.47 (s, 1H), 8.44 (d, J = 5.2 Hz, 1H), 8.26 (s, 1H), 7.51 (d, J = 9.2 Hz, 1H), 7.34 (d, J = 5.2 Hz, 1H), 7.24 (d, J = 9.2 Hz, 1H), 4.99~4.81 (m, 1H), 2.29 (s, 6H), 2.07~2.03 (m, 1H), 1.63~1.56 (m, 1H), 1.15~1.05 (m, 1H); LCMS (electrospray) m/z 324.95 (M + H)+. | C |

TABLE 1-continued

Compounds of Examples

| Ex # | Structure/Name | 1H NMR/MS (M + 1) | Synthetic Method |
|---|---|---|---|
| 6 | 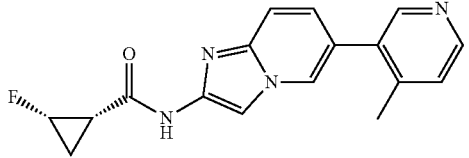<br>(1S,2S)-2-fluoro-N-(6-(4-methylpyridin-3-yl)imidazo[1,2-a]pyridin-2-yl)cyclopropane-1-carboxamide | 1H NMR (400 MHz, DMSO-d6); δ 11.01 (s, 1H), 8.61 (s, 1H), 8.44~8.42 (m, 2H), 7.47 (d, J = 9.2 Hz, 1H), 7.33 (d, J = 5.2 Hz, 1H), 7.25 (dd, J = 9.2, 2.0 Hz, 1H), 4.99~4.78 (m, 1H), 2.28 (s, 3H), 2.15~2.08 (m, 1H), 1.66~1.59 (m, 1H), 1.15~1.12 (m, 1H)); LCMS (electrospray) m/z 311.00 (M + H)+. | A |
| 7 | 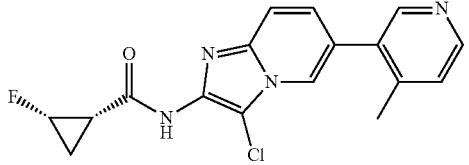<br>(1S,2S)-N-(3-chloro-6-(4-methylpyridin-3-yl)imidazo[1,2-a]pyridin-2-yl)-2-fluorocyclopropane-1-carboxamide | 1H NMR (400 MHz, DMSO-d6); δ 10.46 (s, 1H), 8.47 (s, 1H), 8.30 (s, 1H), 7.63 (d, J = 9.2 Hz, 1H), 7.40 (dd, J = 9.2, 1.6 Hz, 1H), 7.35 (d, J = 4.8 Hz, 1H), 5.01~4.83 (m, 1H), 2.28 (s, 3H), 2.08~2.01 (m, 1H), 1.63~1.56 (m, 1H), 1.20~1.05 (m, 1H); LCMS (electrospray) m/z 344.91 (M + H)+. | B |
| 8 | 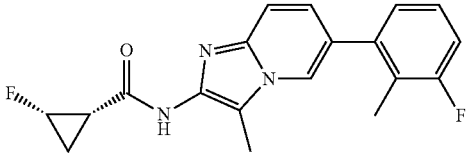<br>(1S,2S)-2-flouro-N-(6-(3-flouro-2-methylphenyl)-3-methylimidazo[1,2-a]pyridin-2-yl)cyclopropane-1-carboxamide | 1H NMR (400 MHz, DMSO-d6); δ 10.24 (s, 1H), 8.19 (s, 1H), 7.49 (d, J = 9.2 Hz, 1H), 7.29 (m, 1H), 7.22~7.18 (m, 3H), 4.99~4.81 (m, 1H), 2.29 (s, 3H), 2.15 (s, 3H), 2.07~2.03 (m, 1H), 1.63~1.56 (m, 1H), 1.12~1.05 (m, 1H); LCMS (electrospray) m/z 341.99 (M + H)+. | C |
| 9 | 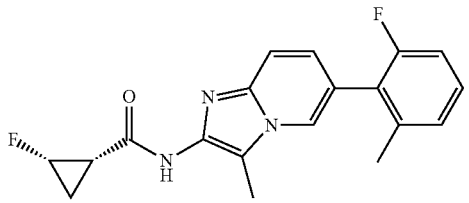<br>(1S,2S)-2-flouro-N-(6-(2-flouro-6-methylphenyl)-3-methylimidazo[1,2-a]pyridin-2-yl)cyclopropane-1-carboxamide | 1H NMR (400 MHz, DMSO); δ 10.25 (s, 1H), 8.22 (s, 1H), 7.51 (d, J = 8.0 Hz, 1H), 7.33 (dd, J = 14.2, 7.8 Hz, 1H), 7.18~7.08 (m, 3H), 4.99~4.81 (m, 1H), 2.27 (s, 3H), 2.17 (s, 3H), 2.06 (m, 1H), 1.64~1.56 (m, 1H), 1.12~1.05 (m, 1H); LCMS (electrospray) m/z 341.99 (M + H)+. | C |
| 10 | 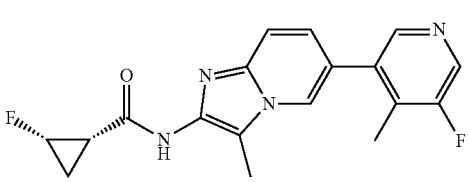<br>(1S,2S)-2-flouro-N-(6-(5-flouro-4-methylpyridin-3-yl)-3-methylimidazo[1,2-a]pyridin-2-yl)cyclopropane-1-carboxamide | $^1$H NMR (400 MHz, DMSO-d$_6$) δ 10.27 (s, 1H), 8.52 (s, 1H), 8.41 (s, 1H), 8.32 (s, 1H), 7.53 (d, J = 9.2 Hz, 1H), 7.26 (dd, J = 9.4, 1.4 Hz, 1H), 4.99~4.81 (m, 1H), 2.30 (s, 3H), 2.23 (s, 3H), 2.07~2.04 (m, 1H), 1.63~1.56 (m, 1H), 1.10~1.09 (m, 1H); LCMS (electrospray) m/z 342.96 (M + H)+. | C |

TABLE 1-continued

Compounds of Examples

| Ex # | Structure/Name | 1H NMR/MS (M + 1) | Synthetic Method |
|---|---|---|---|
| 11 | 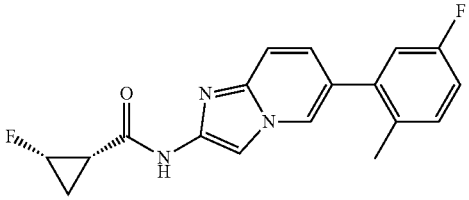<br>(1S,2S)-2-flouro-N-(6-(5-flouro-2-methylphenyl)imidazo[1,2-a]pyridin-2-yl)cyclopropane-1-carboxamide | $^1$H NMR (400 MHz, DMSO-$d_6$) δ 11.00 (s, 1H), 8.56 (s, 1H), 8.06 (s, 1H), 7.44 (d, J = 9.2 Hz, 1H), 7.32 (t, J = 7.2 Hz, 1H), 7.22 (dd, J = 9.2, 2.0 Hz, 1H), 7.12~7.09 (m, 2H), 4.99~4.78 (m, 1H), 2.21 (s, 3H), 2.11~2.10 (m, 1H), 1.66~1.59 (m, 1H), 1.17~1.12 (m, 1H); LCMS (electrospray) m/z 327.92 (M + H)+. | A |
| 12 | 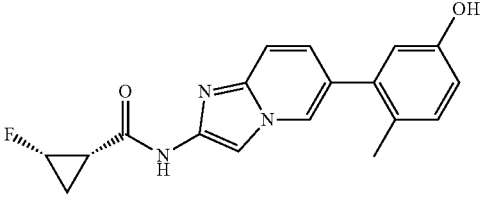<br>(1S,2S)-2-flouro-N-(6-(5-hydroxy-2-methylphenyl)imidazo[1,2-a]pyridin-2-yl)cyclopropane-1-carboxamide | $^1$H NMR (400 MHz, DMSO-$d_6$) δ 10.97 (s, 1H), 8.48 (s, 1H), 8.06 (s, 1H), 7.41 (d, J = 8.8 Hz, 1H), 7.15 (dd, J = 9.4, 1.4 Hz, 1H), 7.06 (d, J = 8.4 Hz, 1H), 6.69~6.64 (m, 2H), 4.98~4.78 (m, 1H), 2.12~2.07 (m, 4H), 1.66~1.58 (m, 1H), 1.16~1.09 (m, 1H); LCMS (electrospray) m/z 325.90 (M + H)+. | A |
| 13 | 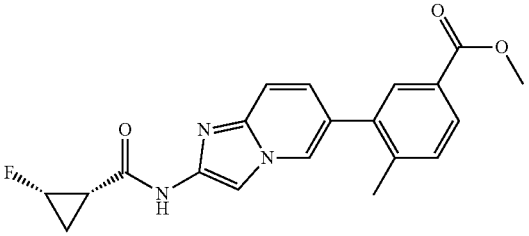<br>methyl 3-(2-((1S,2S)-2-flourocyclopropane-1-carboxamido)imidazo[1,2-a]pyridin-6-yl)-4-methylbenzoate | $^1$H NMR (400 MHz, DMSO-$d_6$) δ 11.00 (s, 1H), 8.59 (s, 1H), 7.86 (dd, J = 7.8, 1.8 Hz, 1H), 7.81 (d, J = 1.6 Hz, 1H), 7.48~7.44 (m, 2H), 7.22 (dd, J = 9.2, 1.6 Hz, 1H), 4.99~4.78 (m, 1H), 3.82 (s, 3H), 2.32 (s, 3H), 2.12~2.11 (m, 1H), 1.65~1.59 (m, 1H), 1.15~1.10 (m, 1H); LCMS (electrospray) m/z 367.98 (M + H)+. | A |
| 14 | 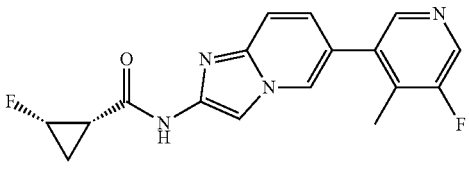<br>(1S,2S)-2-flouro-N-(6-(5-fluoro-4-methylpyridin-3-yl)imidazo[1,2-a]pyridin-2-yl)cyclopropane-1-carboxamide | $^1$H NMR (400 MHz, DMSO-$d_6$) δ 11.03 (s, 1H), 8.66 (s, 1H), 8.50 (s, 1H), 8.35 (s, 1H), 8.35 (s, 1H), 8.08 (s, 1H), 7.49 (d, J = 9.2 Hz, 1H), 7.27 (dd, J = 9.0, 1.8 Hz, 1H), 4.99~4.79 (m, 1H), 2.23 (s, 3H), 2.12~2.11 (m, 1H), 1.66~1.59 (m, 1H), 1.16~1.10 (m, 1H); LCMS (electrospray) m/z 328.96 (M + H)+. | A |
| 15 | 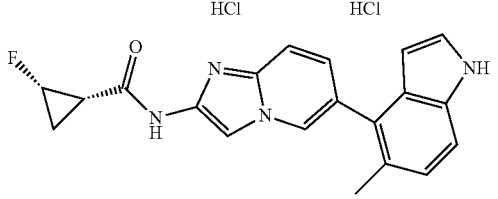<br>(1S,2S)-2-flouro-N-(6-(5-methyl-1H-indol-4-yl)imidazo[1,2-a]pyridin-2-yl)cyclopropane-1-carboxamide. 2 HCl salt | $^1$H NMR (400 MHz, DMSO-$d_6$) δ 11.68 (bs, 1H), 11.16 (s, 1H), 8.74 (s, 1H), 8.15 (s, 1H), 7.75 (d, J = 9.2 Hz, 1H), 7.59 (d, J = 9.2 Hz, 1H), 7.34 (d, J = 8.4 Hz, 1H), 7.29 (t, J = 2.8 Hz, 1H), 7.04 (d, J = 8.4 Hz, 1H), 6.08 (s, 1H), 5.07~4.87 (m, 1H), 2.24 (s, 3H), 2.17 (m, 1H), 1.71~1.65 (m, 1H), 1.25~1.19 (m, 1H); LCMS (electrospray) m/z 349.04 (M + H)+. | A |

TABLE 1-continued

Compounds of Examples

| Ex # | Structure/Name | 1H NMR/MS (M + 1) | Synthetic Method |
|---|---|---|---|
| 16 | 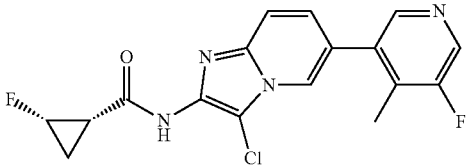<br>(1S,2S)-N-(3-chloro-6-(5-fluoro-4-methylpyridin-3-yl)imidazo[1,2-a]pyridin-2-yl)-2-fluorocyclopropane-1-carboxamide | $^1$H NMR (400 MHz, DMSO-d$_6$) δ 10.48 (s, 1H), 8.53 (s, 1H), 8.40 (s, 1H), 8.37 (s, 1H), 7.66 (d, J = 10.0 Hz, 1H), 7.41 (dd, J = 9.0, 1.4 Hz, 1H), 5.01~4.83 (m, 1H), 2.22 (d, J = 2.0 Hz, 3H), 2.11~2.03 (m, 1H), 1.63~1.56 (m, 1H), 1.14~1.11 (m, 1H); LCMS (electrospray) m/z 362.92 (M + H)+. | B |
| 17 | 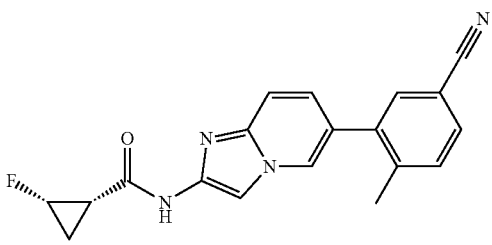<br>(1S,2S)-N-(6-(5-cyano-2-methylphenyl)imidazo[1,2-a]pyridin-2-yl)-2-fluorocyclopropane-1-carboxamide | $^1$H NMR (400 MHz, DMSO-d$_6$) δ 8.59 (s, 1H), 8.06 (s, 1H), 7.76~7.74 (m, 2H), 7.52 (d, J = 8.4 Hz, 1H), 7.46 (d, J = 9.2 Hz, 1H), 7.23 (dd, J = 9.2, 1.6 Hz, 1H), 4.99~4.78 (m, 1H), 2.33 (s, 3H), 2.14~2.08 (m, 1H), 1.66~1.59 (m, 1H), 1.17~1.03 (m, 1H); LCMS (electrospray) m/z 335.01 (M + H)+. | A |
| 18 | 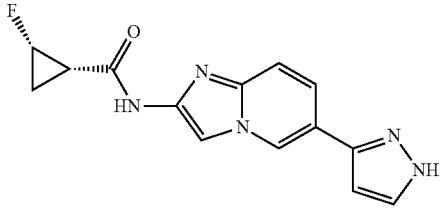<br>(1S,2S)-N-(6-(1H-pyrazol-3-yl)imidazo[1,2-a]pyridin-2-yl)-2-fluorocyclopropane-1-carboxamide | $^1$H NMR (400 MHz, DMSO-d$_6$) δ 12.90 (s, 1H), 10.97 (s, 1H), 8.94 (s, 1H), 8.05 (s, 1H), 7.78 (s, 1H), 7.67 (d, J = 9.2 Hz, 1H), 7.41 (d, J = 9.2 Hz, 1H), 6.67 (s, 1H), 4.98~4.78 (m, 1H), 2.11~2.09 (m, 1H), 1.65~1.59 (m, 1H), 1.51~1.09 (m, 1H); LCMS (electrospray) m/z 285.93 (M + H)+. | A |
| 19 | 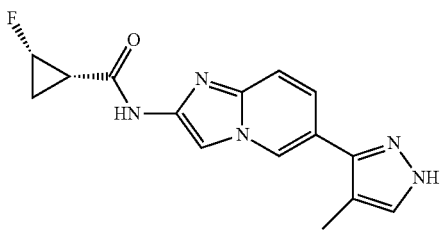<br>(1S,2S)-2-fluoro-N-(6-(4-methyl-1H-pyrazol-3-yl)imidazo[1,2-a]pyridin-2-yl)cyclopropane-1-carboxamide | $^1$H NMR (400 MHz, DMSO-d$_6$) δ 12.50 (s, 1H), 10.67 (s, 1H), 8.65 (s, 1H), 8.09 (s, 1H), 7.53~7.39 (m, 3H), 4.93~4.76 (m, 1H), 2.19~2.11 (m, 4H), 1.69~1.62 (m, 1H), 1.15~1.07 (m, 1H); LCMS (electrospray) m/z 299.96 (M + H)+ | A |
| 20 | 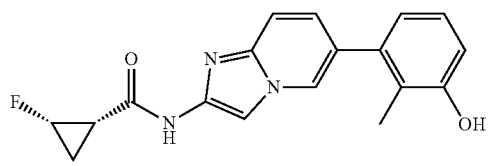<br>(1S,2S)-2-flouro-N-(6-(3-hydroxy-2-methylphenyl)imidazo[1,2-a]pyridin-2-yl)cyclopropane-1-carboxamide | $^1$H NMR (400 MHz, DMSO-d$_6$) δ 10.69 (s, 1H), 9.44 (s, 1H), 8.45 (s, 1H), 8.05 (s, 1H), 7.40 (d, J = 9.2 Hz, 1H), 7.13 (dd, J = 9.2, 2.0 Hz, 1H), 7.08~7.01 (m, 1H), 6.81 (d, J = 7.6 Hz, 1H), 6.69 (d, J = 6.8 Hz, 1H), 4.98~4.79 (m, 1H), 2.13~2.09 (m, 1H), 2.02 (s, 3H), 1.65~1.58 (m, 1H), 1.14~1.09 (m, 1H); LCMS (electrospray) m/z 326.00 (M + H)+ | A |

TABLE 1-continued

Compounds of Examples

| Ex # | Structure/Name | 1H NMR/MS (M + 1) | Synthetic Method |
|---|---|---|---|
| 21 | 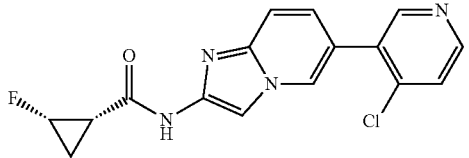<br>(1S,2S)-N-(6-(4-chloropyridin-3-yl)imidazo[1,2-a]pyridin-2-yl)-2-fluorocyclopropane-1-carboxamide | $^1$H NMR (400 MHz, DMSO-d$_6$) δ 11.04 (s, 1H), 8.73 (s, 1H), 8.65 (s, 1H), 8.55 (d, J = 5.2 Hz, 1H), 8.09 (s, 1H), 7.68 (d, J = 5.6 Hz, 1H), 7.50 (d, J = 9.2 Hz, 1H), 7.32 (dd, J = 9.2, 2.0 Hz, 1H), 4.99~4.79 (m, 1H), 2.11~2.10 (m, 1H), 1.65~1.59 (m, 1H), 1.17~1.10 (m, 1H); LCMS (electrospray) m/z 330.88 (M + H)+ | A |
| 22 | 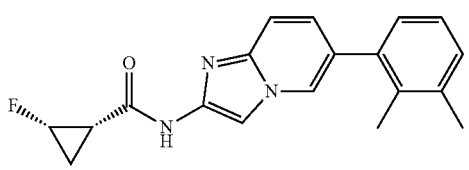<br>(1S,2S)-N-(6-(2,3-dimethylphenyl)imidazo[1,2-a]pyridin-2-yl)-2-fluorocyclopropane-1-carboxamide | $^1$H NMR (400 MHz, DMSO-d$_6$) δ 10.97 (s, 1H), 8.45 (s, 1H), 8.06 (s, 1H), 7.42 (d, J = 9.2 Hz, 1H), 7.19~7.06 (m, 4H), 4.98~4.78 (m, 1H), 2.27 (s, 3H), 2.21~2.11 (m, 4H), 1.66~1.58 (m, 1H), 1.16~1.11 (m, 1H); LCMS (electrospray) m/z 323.83 (M + H)+. | A |
| 23 | 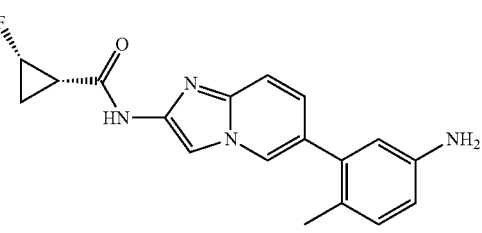<br>(1S,2S)-N-(6-(5-amino-2-methylphenyl)imidazo[1,2-a]pyridin-2-yl)-2-fluorocyclopropane-1-carboxamide | $^1$H NMR (400 MHz, DMSO-d$_6$) δ 10.96 (s, 1H), 8.44 (s, 1H), 8.06 (s, 1H), 7.39 (d, J = 8.0 Hz, 1H), 7.12 (dd, J = 9.2, 1.6 Hz, 1H), 6.91 (d, J = 8.4 Hz, 1H), 6.50~6.46 (m, 2H), 4.98~4.78 (m, 3H), 2.12~2.09 (m, 1H), 2.05 (s, 3H), 1.66~1.58 (m, 1H), 1.14~1.11 (m, 1H); LCMS (electrospray) m/z 324.95 (M + H)+. | A |
| 24 | 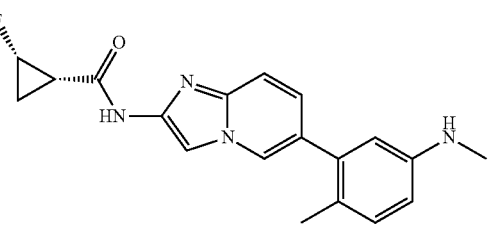<br>(1S,2S)-2-fluoro-N-(6-(2-methyl-5-(methylamino)phenyl)imidazo[1,2-a]pyridin-2-yl)-2-cyclopropane-1-carboxamide | $^1$H NMR (400 MHz, DMSO-d$_6$) δ 10.97 (s, 1H), 8.46 (s, 1H), 8.06 (s, 1H), 7.39 (d, J = 9.2 Hz, 1H), 7.14 (d, J = 9.2 Hz, 1H), 6.98 (d, J = 8.0 Hz, 1H), 6.46 (d, J = 7.6 Hz, 1H), 6.41 (s, 1H), 5.49 (d, J = 5.2 Hz, 1H), 4.96~4.80 (m, 1H), 2.63 (d, J = 4.4 Hz, 3H), 2.10~2.07 (m, 4H), 1.64~1.59 (m, 1H), 1.12 (m, 1H); LCMS (electrospray) m/z 338.99 (M + H)+. | A |
| 25 | 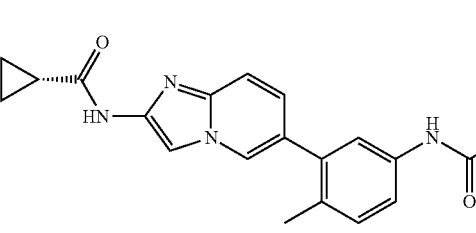<br>(1S,2S)-N-(6-(5-acetamino-2-methylphenyl)imidazo[1,2-a]pyridin-2-yl)-2-fluorocyclopropane-1-carboxamide | $^1$H NMR (400 MHz, DMSO-d$_6$) δ 10.99 (s, 1H), 9.90 (s, 1H), 8.50 (s, 1H), 8.07 (s, 1H), 7.49~7.42 (m, 3H), 7.19 (d, J = 8.4 Hz, 1H), 7.16 (dd, J = 9.2, 1.6 Hz, 1H), 4.99~4.78 (m, 1H), 2.17 (s, 3H), 2.13~2.11 (m, 1H), 1.99 (s, 3H), 1.66~1.58 (m, 1H), 1.15~1.10 (m, 1H); LCMS (electrospray) m/z 366.98 (M + H)+. | A |

TABLE 1-continued

Compounds of Examples

| Ex # | Structure/Name | 1H NMR/MS (M + 1) | Synthetic Method |
|---|---|---|---|
| 26 | 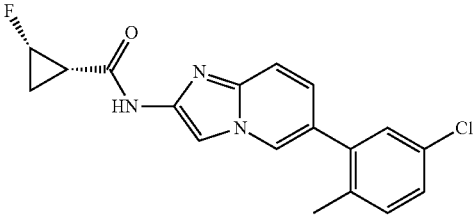<br>(1S,2S)-N-(6-(5-chloro-2-methylphenyl)imidazo[1,2-a]pyridin-2-yl)-2-fluorocyclopropane-1-carboxamide | $^1$H NMR (400 MHz, DMSO-d$_6$) δ 11.00 (s, 1H), 8.56 (s, 1H), 8.05 (s, 1H), 7.43 (d, J = 9.2 Hz, 1H), 7.36~7.31 (m, 3H), 7.20 (dd, J = 9.2, 1.6 Hz, 1H), 4.99~4.78 (m, 1H), 2.22 (s, 3H), 2.12~2.10 (m, 1H), 1.66~1.59 (m, 1H), 1.13~1.07(m, 1H); LCMS (electrospray) m/z 343.94 (M + H)+. | A |
| 27 | 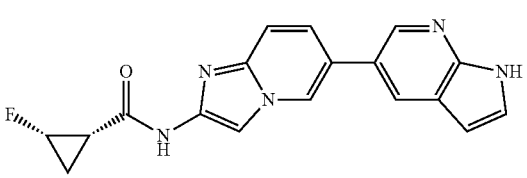<br>(1S,2S)-N-(6-(1H-pyrrolo[2,3-b]pyridin-5-yl)imidazo[1,2-a]pyridin-2-yl)-2-fluorocyclopropane-1-carboxamide | $^1$H NMR (400 MHz, DMSO-d$_6$) δ 11.71 (s, 1 H), 10.99 (s, 1 H), 8.89 (s, 1 H), 8.50 (d, J = 1.6 Hz, 1 H), 8.20 (d, J = 1.6 Hz, 1 H), 8.07 (s, 1 H), 7.59 (d, J = 1.6 Hz, 1 H), 7.50~7.47 (m, 2 H), 4.99~4.79 (m, 1 H), 2.12~2.11 (m, 1 H), 1.67~1.59 (m, 1 H), 1.17~1.09 (m, 1 H); LCMS (electrospray) m/z 335.91 (M + H)+. | A |
| 28 | 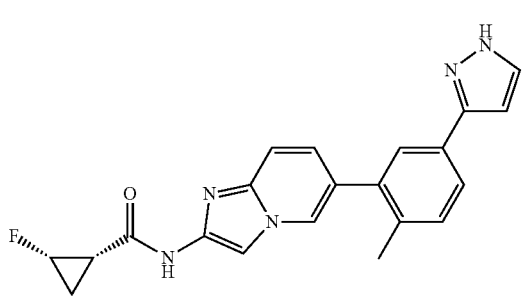<br>(1S,2S)-2-fluoro-N-(6-(2-methyl-5-(1H-pyrazol-3-yl)phenyl)imidazo[1,2-a]pyridin-2-yl)cyclopropane-1-carboxamide | $^1$H NMR (400 MHz, DMSO-d$_6$) δ 12.82 (s, 1H), 10.99 (s, 1H), 8.58 (s, 1H), 8.08 (s, 1H), 7.73~7.69 (m, 2H), 7.46~7.23 (m, 4H), 6.70 (s, 1H), 4.97~4.80 (m, 1H), 2.25 (s, 3H), 2.14~2.09 (m, 1H), 1.66~1.59 (m, 1H), 1.13~1.08 (m, 1H); LCMS (electrospray) m/z 376.00 (M + H)+. | D |
| 29 | 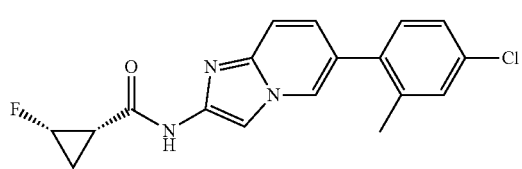<br>(1S,2S)-N-(6-(4-chloro-2-methylphenyl)imidazo[1,2-a]pyridin-2-yl)-2-fluorocyclopropane-1-carboxamide | $^1$H NMR (400 MHz, DMSO-d$_6$) δ 10.99 (s, 1H), 8.52 (dd, J = 1.8, 1.0 Hz, 1H), 8.06 (s, 1H), 7.44~7.40 (m, 2H), 7.33~7.26 (m, 2H), 7.18 (dd, J = 9.2, 2.0 Hz, 1H), 4.98~4.78 (m, 1H), 2.24 (s, 3H), 2.11 (m, 1H), 1.66~1.58 (m, 1H), 1.13~1.09 (m, 1H); LCMS (electrospray) m/z 343.94 (M + H)+. | A |
| 30 | 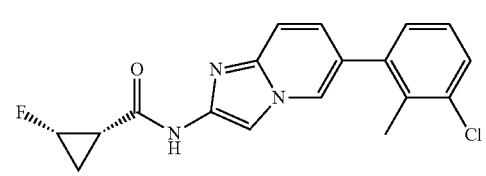<br>(1S,2S)-N-(6-(4-chloro-2-methylphenyl)imidazo[1,2-a]pyridin-2-yl)-2-fluorocyclopropane-1-carboxamide | $^1$H NMR (400 MHz, DMSO-d$_6$) δ 11.00 (s, 1H), 8.53 (s, 1H), 8.06 (s, 1H), 7.48~7.43 (m, 2H), 7.30~7.24 (m, 2H), 7.18 (dd, J = 9.2, 1.2 Hz, 1H), 4.98~4.79 (m, 1H), 2.25 (s, 3H), 2.11 (m, 1H), 1.65~1.58 (m, 1H), 1.15~1.10 (m, 1H); LCMS (electrospray) m/z 343.94 (M + H)+. | A |

TABLE 1-continued

Compounds of Examples

| Ex # | Structure/Name | 1H NMR/MS (M + 1) | Synthetic Method |
|---|---|---|---|
| 31 | (1S,2S)-2-flouro-N-(6-(4-(trifluoromethyl)pyridin-3-yl)imidazo[1,2-a]pyridin-2-yl)cyclopropane-1-carboxamide | $^1$H NMR (400 MHz, DMSO-$d_6$) δ 11.05 (s, 1H), 8.89 (d, J = 5.6 Hz, 1H), 8.65 (s, 1H), 8.10 (s, 1H), 7.86 (d, J = 5.6 Hz, 1H), 7.49 (d, J = 9.2 Hz, 1H), 7.19 (d, J = 10.0 Hz, 1H), 4.99~4.79 (m, 1H), 2.13~2.10 (m, 1H), 1.66~1.59 (m, 1H), 1.16~1.11 (m, 1H); LCMS (electrospray) m/z 364.86 (M + H)+. | A |
| 32 | (1S,2S)-N-(6-(2-4-dimethylphenyl)imidazo[1,2-a]pyridin-2-yl)-2-fluorocyclopropane-1-carboxamide | $^1$H NMR (400 MHz, DMSO-$d_6$) δ 10.97 (s, 1H), 8.47 (s, 1H), 8.05 (s, 1H), 7.41 (d, J = 9.2 Hz, 1H), 7.16~7.04 (m, 4H), 4.97~4.79 (m, 1H), 2.28 (s, 3H), 2.20 (s, 3H), 2.14~2.10 (m, 1H), 1.65~1.58 (m, 1H), 1.16~1.05 (m, 1H); LCMS (electrospray) m/z 323.75 (M + H)+. | A |
| 33 | (1S,2S)-2-flouro-N-(3-fluoro-6-(3-fluoro-2-methylphenyl)imidazo[1,2-a]pyridin-2-yl)cyclopropane-1-carboxamide | $^1$H NMR (400 MHz, DMSO-$d_6$) δ 10.56 (s, 1H), 8.23 (s, 1H), 7.49 (d, J = 9.6 Hz, 1H), 7.33~7.27 (m, 1H), 7.24~7.16 (m, 3H), 5.01~4.81 (m, 1H), 2.15 (s, 3H), 2.05~2.05 (m, 1H), 1.63~1.56 (m, 1H), 1.17~1.09 (m, 1H); LCMS (electrospray) m/z 345.96 (M + H)+. | E |
| 34 | (1S,2S)-N-(6-(2-5-dimethylphenyl)imidazo[1,2-a]pyridin-2-yl)-2-fluorocyclopropane-1-carboxamide | $^1$H NMR (400 MHz, DMSO-$d_6$) δ 10.97 (s, 1H), 8.49 (s, 1H), 8.05 (s, 1H), 7.41 (d, J = 8.8 Hz, 1H), 7.17 (dd, J = 9.2, 1.6 Hz, 2H), 7.08 (d, J = 7.6 Hz, 2H), 4.98~4.78 (m, 1H), 2.27 (s, 3H), 2.19 (s, 3H), 2.11~2.11 (m, 1H), 1.65~1.58 (m, 1H), 1.15~1.09 (m, 1H); LCMS (electrospray) m/z 323.68 (M + H)+. | A |
| 35 | (1S,2S)-2-fluoro-N-(6-(2-oxoindolin-6-yl)imidazo[1,2-a]pyridin-2-yl)cyclopropane-1-carboxamide | $^1$H NMR (400 MHz, DMSO-$d_6$) δ 10.98 (s, 1H), 10.50 (s, 1H), 8.83 (t, J = 1.2 Hz, 1H), 8.08 (s, 1H), 7.45 (d, J = 1.2 Hz, 2H), 7.27 (d, J = 7.2 Hz, 1H), 7.20 (dd, J = 7.6, 1.6 Hz, 1H), 7.02 (d, J = 1.2 Hz, 1H), 4.99~4.78 (m, 1H), 3.49 (s, 2H), 2.12~2.09 (m, 1H), 1.66~1.59 (m, 1H), 1.15~1.10 (m, 1H); LCMS (electrospray) m/z 350.99 (M + H)+. | A |
| 36 | (1S,2S)-N-(6-(4-cyanopyridin-3-yl)imidazo[1,2-a]pyridin-2-yl)-2-fluorocyclopropane-1-carboxamide | $^1$H NMR (400 MHz, DMSO-$d_6$) δ 11.09 (s, 1H), 8.95 (s, 1H), 8.91 (s, 1H), 8.82 (d, J = 4.8 Hz, 1H), 8.13 (s, 1H), 7.99 (dd, J = 4.8, 0.8 Hz, 1H), 7.58 (d, J = 9.2 Hz, 1H), 7.49 (dd, J = 9.2, 2.0 Hz, 1H), 5.00~4.79 (m, 1H), 2.14~2.10 (m, 1H), 1.67~1.60 (m, 1H), 1.18~1.10 (m, 1H); LCMS (electrospray) m/z 321.95 (M + H)+. | A |

TABLE 1-continued

Compounds of Examples

| Ex # | Structure/Name | 1H NMR/MS (M + 1) | Synthetic Method |
|---|---|---|---|
| 37 | 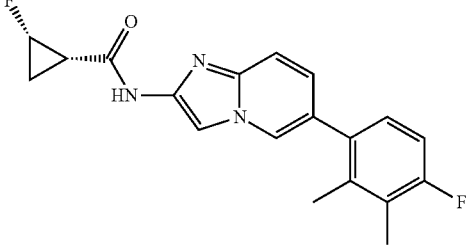<br>(1S,2S)-2-fluoro-N-(6-(4-fluoro-2,3-dimethylphenyl)imidazo[1,2-a]pyridin-2-yl)cyclopropane-1-carboxamide | $^1$H NMR (400 MHz, DMSO-d$_6$) δ 10.98 (s, 1H), 8.44 (dd, J = 1.8, 1.0 Hz, 1H), 8.05 (s, 1H), 7.42 (d, J = 9.2 Hz, 1H), 7.14~7.09 (m, 2H), 7.04 (m, 1H), 4.98~4.78 (m, 1H), 2.18 (d, J = 2.0 Hz, 3H), 2.14~2.08 (m, 4H), 1.65~1.58 (m, 1H), 1.15~1.09 (m, 1H); LCMS (electrospray) m/z 341.99 (M + H)+. | A |
| 38 | 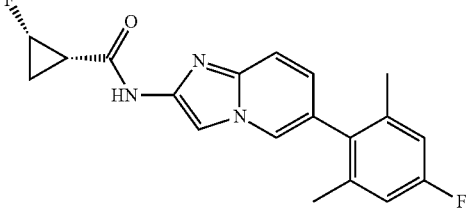<br>(1S,2S)-2-fluoro-N-(6-(4-fluoro-2,6-dimethylphenyl)imidazo[1,2-a]pyridin-2-yl)cyclopropane-1-carboxamide | $^1$H NMR (400 MHz, DMSO-d$_6$) δ 10.99 (s, 1H), 8.35 (s, 1H), 8.03 (s, 1H), 7.45 (d, J = 9.2 Hz, 1H), 6.99~6.94 (m, 3H), 4.97~4.79 (m, 1H), 2.11 (m, 1H), 2.03 (s, 3H), 2.02 (s, 3H), 1.66~1.58 (m, 1H), 1.13~1.11 (m, 1H); LCMS (electrospray) m/z 341.84 (M + H)+. | A |
| 39 | 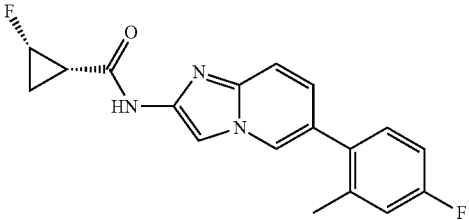<br>(1S,2S)-2-fluoro-N-(6-(4-fluoro-2-methylphenyl)imidazo[1,2-a]pyridin-2-yl)cyclopropane-1-carboxamide | $^1$H NMR (400 MHz, DMSO-d$_6$) δ 10.98 (s, 1H), 8.50 (s, 1H), 8.05 (s, 1H), 7.42 (d, J = 9.2 Hz, 1H), 7.31~7.27 (m, 1H), 7.17 (dd, J = 9.2, 1.6 Hz, 2H), 7.08 (dt, J = 14.4, 4.2 Hz, 1H), 4.98~4.78 (m, 1H), 2.24 (s, 3H), 2.11~2.09 (m, 1H), 1.66~1.58 (m, 1H), 1.16~1.08 (m, 1H); LCMS (electrospray) m/z 328.10 (M + H)+. | A |
| 40 | 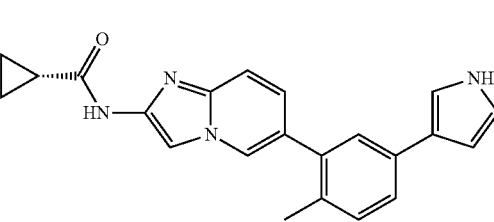<br>(1S,2S)-2-fluoro-N-(6-(2-methyl-5-(1H-pyrrol-3-yl)phenyl)imidazo[1,2-a]pyridin-2-yl)cyclopropane-1-carboxamide | $^1$H NMR (400 MHz, DMSO-d$_6$) δ 10.97 (s, 1H), 10.86 (bs, 1H), 8.54 (s, 1H), 8.07 (s, 1H), 7.44~7.40 (m, 3H), 7.23~7.19 (m, 3H), 6.74 (dd, J = 4.4, 2.8 Hz, 1H), 6.41 (dd, J = 4.4, 2.8 Hz, 1H), 4.97~4.79 (m, 1H), 2.20 (s, 3H), 2.11 (m, 1H), 1.66~1.59 (m, 1H), 1.15~1.10 (m, 1H); LCMS (electrospray) m/z 375.10 (M + H)+. | F |

TABLE 1-continued

Compounds of Examples

| Ex # | Structure/Name | 1H NMR/MS (M + 1) | Synthetic Method |
|---|---|---|---|
| 41 | 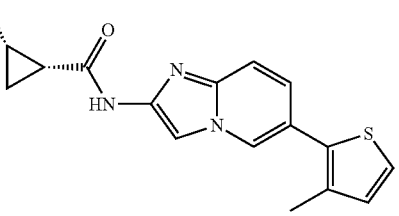<br>(1S,2S)-2-fluoro-N-(6-(3-methylthiophen-2-yl)imidazo[1,2-a]pyridin-2-yl)cyclopropane-1-carboxamide | $^1$H NMR (400 MHz, DMSO-$d_6$) δ 11.00 (s, 1H), 8.66 (t, J = 0.8 Hz, 1H), 8.11 (s, 1H), 7.47~7.44 (m, 2H), 7.26 (dd, J = 9.2, 2.0 Hz, 1H), 6.99 (d, J = 4.8 Hz, 1H), 4.99~4.78 (m, 1H), 2.26 (s, 3H), 2.11 (m, 1H), 1.66~1.59 (m, 1H), 1.15~1.10 (m, 1H); LCMS (electrospray) m/z 316.10 (M + H)+. | A |
| 42 | 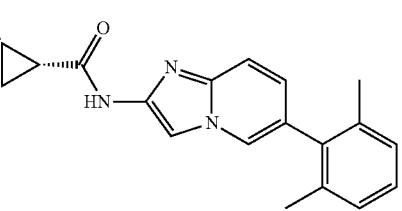<br>(1S,2S)-N-(6-(2,6-dimethylphenyl)imidazo[1,2-a]pyridin-2-yl)-2-fluorocyclopropane-1-carboxamide | $^1$H NMR (400 MHz, DMSO-d6) δ 10.98 (s, 1H), 8.35 (s, 1H), 8.03 (s, 1H), 7.45 (d, J = 9.2 Hz, 1H), 7.19~7.10 (m, 3H), 6.97 (dd, J = 9.0, 1.8 Hz, 1H), 4.98~4.78 (m, 1H), 2.11~2.10 (m, 1H), 2.02 (s, 3H), 2.01 (s, 3H), 1.64~1.58 (m, 1H), 1.44~1.10 (m, 1H); LCMS (electrospray) m/z 325.00 (M + H)+. | A |
| 43 | 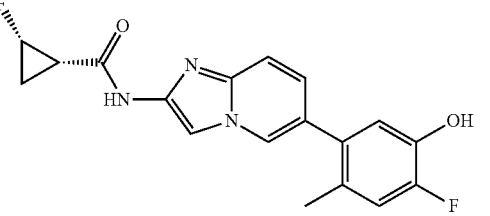<br>(1S,2S)-2-fluoro-N-(6-(4-fluoro-5-hydroxy-2-methylphenyl)imidazo[1,2-a]pyridin-2-yl)cyclopropane-1-carboxamide | $^1$H NMR (400 MHz, DMSO-$d_6$) δ 10.98 (s, 1H), 9.75 (bs, 1H), 8.47 (s, 1H), 8.05 (s, 1H), 7.40 (d, J = 9.2 Hz, 1H), 7.13 (dd, J = 9.2, 2.0 Hz, 1H), 7.06 (d, J = 12.4 Hz, 1H), 6.81 (d, J = 9.2 Hz, 1H), 4.98~4.78 (m, 1H), 2.14~2.07 (m, 4H), 1.65~1.58 (m, 1H), 1.16~1.07 (m, 1H); LCMS (electrospray) m/z 343.90 (M + H)+. | G |
| 44 | 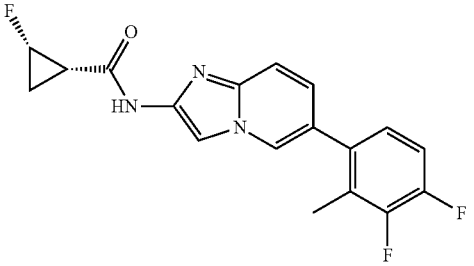<br>(1S,2S)-N-(6-(3,4-difluoro-2-methylphenyl)imidazo[1,2-a]pyridin-2-yl)-2-fluorocyclopropane-1-carboxamide | $^1$H NMR (400 MHz, DMSO-$d_6$) δ 11.00 (s, 1H), 8.54 (s, 1H), 8.07 (s, 1H), 7.45 (d, J = 9.2 Hz, 1H), 7.36 (m, 1H), 7.19~7.13 (m, 2H), 4.99~4.78 (m, 1H), 2.19 (d, J = 2.8 Hz, 3H), 2.11 (m, 1H), 1.66~1.58 (m, 1H), 1.15~1.10 (m, 1H); LCMS (electrospray) m/z 346.00 (M + H)+. | G |

TABLE 1-continued

Compounds of Examples

| Ex # | Structure/Name | 1H NMR/MS (M + 1) | Synthetic Method |
|---|---|---|---|
| 45 | 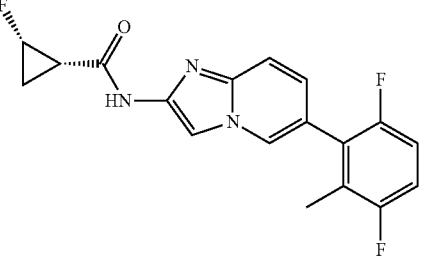<br>(1S,2S)-N-(6-(3,6-difluoro-2-methylphenyl)imidazo[1,2-a]pyridin-2-yl)-2-fluorocyclopropane-1-carboxamide | $^1$H NMR (400 MHz, DMSO-d$_6$) δ 11.02 (s, 1H), 8.57 (s, 1H), 8.07 (s, 1H), 7.49 (d, J = 9.2 Hz, 1H), 7.26 (m, 1H), 7.19 (m, 1H), 7.12 (dd, J = 9.0, 1.0 Hz, 1H), 4.99~4.78 (m, 1H), 2.10 (m, 1H), 2.06 (d, J = 2.4 Hz, 3H), 1.66~1.59 (m, 1H), 1.15~1.10 (m, 1H); LCMS (electrospray) m/z 345.96 (M + H)+. | G |
| 46 | 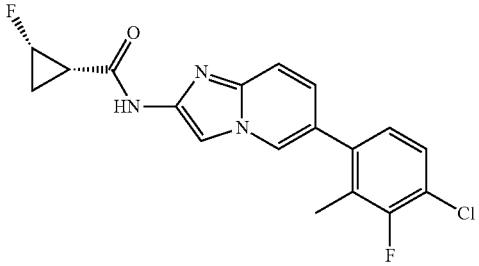<br>(1S,2S)-N-(6-(4-chloro-3-fluoro-2-methylphenyl)imidazo[1,2-a]pyridin-2-yl)-2-fluorocyclopropane-1-carboxamide | 1H NMR (400 MHz, DMSO-d6) δ 11.01 (s, 1H), 8.56 (s, 1H), 8.07 (s, 1H), 7.49~7.44 (m, 2H), 7.20~7.15 (m, 2H), 4.98~4.79 (m, 1H), 2.19 (d, J = 2.8 Hz, 3H), 2.11 (m, 1H), 1.65~1.59 (m, 1H), 1.15~1.10 (m, 1H); LCMS (electrospray) m/z 362.00 (M + H)+. | G |
| 47 | 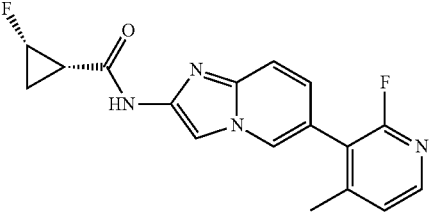<br>(1S,2S)-2-fluoro-N-(6-(2-fluoro-4-methylpyridin-3-yl)imidazo[1,2-a]pyridin-2-yl)cyclopropane-1-carboxamide | $^1$H NMR (400 MHz, DMSO-d$_6$) δ 11.03 (s, 1H), 8.61 (s, 1H), 8.11 (d, J = 5.2 Hz, 1H), 8.06 (s, 1H), 7.49 (d, J = 9.2 Hz, 1H), 7.34 (d, J = 5.2 Hz, 1H), 7.16 (d, J = 9.2 Hz, 1H), 4.99~4.78 (m, 1H), 2.24 (s, 3H), 2.17~2.09 (m, 1H), 1.66~1.59 (m, 1H), 1.17~1.11 (m, 1H); LCMS (electrospray) m/z 329.01 (M + H)+. | A |
| 48 | 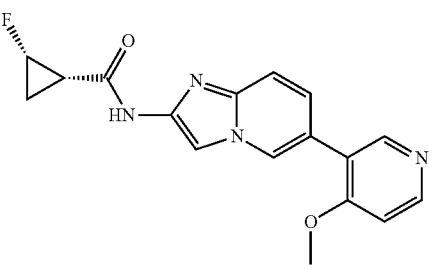<br>(1S,2S)-2-fluoro-N-(6-(4-methoxypyridin-3-yl)imidazo[1,2-a]pyridin-2-yl)cyclopropane-1-carboxamide | $^1$H NMR (400 MHz, DMSO-d$_6$) 11.00 (s, 1H), 8.46 (s, 1H), 8.06 (s, 1H), 7.47 (d, J = 9.2 Hz, 1H), 7.40~7.38 (m, 1H), 7.31~7.30 (m, 2H), 7.02 (dd, J = 9.2, 1.6 Hz, 1H), 4.99~4.78 (m, 1H), 2.13~2.09 (m, 4H), 1.71~1.58 (m, 1H), 1.15~1.10 (m, 1H); LCMS (electrospray) m/z 343.94 (M + H)+. | A |

TABLE 1-continued

Compounds of Examples

| Ex # | Structure/Name | 1H NMR/MS (M + 1) | Synthetic Method |
|---|---|---|---|
| 49 | (1S,2S)-N-(6-(6-amino-4-methylpyridin-3-yl)imidazo[1,2-a]pyridin-2-yl)-2-fluorocyclopropane-1-carboxamide | $^1$H NMR (400 MHz, DMSO-d$_6$) δ 11.03 (s, 1H), 8.55 (s, 1H), 7.88 (s, 1H), 7.80 (bs, 2H), 7.47 (d, J = 9.2 Hz, 1H), 7.21 (dd, J = 9.2, 2.0 Hz, 1H), 6.84 (s, 1H), 4.99~4.79 (m, 1H), 2.25 (s, 3H), 2.14~2.07 (m, 1H), 1.65~1.58 (m, 1H), 1.16~1.05 (m, 1H); LCMS (electrospray) m/z 325.70 (M + H)+. | A |
| 50 | (1S,2S)-N-(6-(5-amino-3-fluoro-2-methylphenyl)imidazo[1,2-a]pyridin-2-yl)-2-fluorocyclopropane-1-carboxamide | $^1$H NMR (400 MHz, DMSO-d$_6$) δ 10.98 (s, 1H), 8.48 (dd, J = 1.6, 0.8 Hz, 1H), 8.07 (s, 1H), 7.41 (d, J = 9.2 Hz, 1H), 7.12 (dd, J = 9.2, 2.0 Hz, 1H), 6.35~6.31 (m, 2H), 5.26 (bs, 2H), 4.97~4.78 (m, 1H), 2.10 (m, 1H), 1.93 (d, J = 2.0 Hz, 3H), 1.65~1.58 (m, 1H), 1.15~1.09 (m, 1H); LCMS (electrospray) m/z 343.10 (M + H)+. | G |
| 51 | (1S,2S)-2-fluoro-N-(6-(5-methyl-2-oxoindolin-4-yl)imidazo[1,2-a]pyridin-2-yl)cyclopropane-1-carboxamide | $^1$H NMR (400 MHz, DMSO-d$_6$) δ 10.97 (s, 1H), 10.32 (s, 1H), 8.50 (s, 1H), 8.03 (s, 1H), 7.43 (d, J = 9.2 Hz, 1H), 7.14~7.10 (m, 2H), 6.73 (d, J = 8.0 Hz, 1H), 4.98~4.78 (m, 1H), 3.30 (s, 2H), 2.11~2.09 (m, 4H), 1.66~1.59 (m, 1H), 1.16~1.11 (m, 1H); LCMS (electrospray) m/z 365.02 (M + H)+. | G |
| 52 | (1S,2S)-N-(6-(2-chloro-6-methylphenyl)imidazo[1,2-a]pyridin-2-yl)-2-fluorocyclopropane-1-carboxamide | $^1$H NMR (400 MHz, DMSO-d$_6$) δ 11.00 (s, 1H), 8.46 (s, 1H), 8.06 (s, 1H), 7.47 (d, J = 9.2 Hz, 1H), 7.40~7.38 (m, 1H), 7.31~7.30 (m, 2H), 7.02 (dd, J = 9.2, 1.6 Hz, 1H), 4.99~4.78 (m, 1H), 2.13~2.09 (m, 4H), 1.71~1.58 (m, 1H), 1.15~1.10 (m, 1H); LCMS (electrospray) m/z 343.94 (M + H)+. | A |

TABLE 1-continued

Compounds of Examples

| Ex # | Structure/Name | 1H NMR/MS (M + 1) | Synthetic Method |
|---|---|---|---|
| 53 | 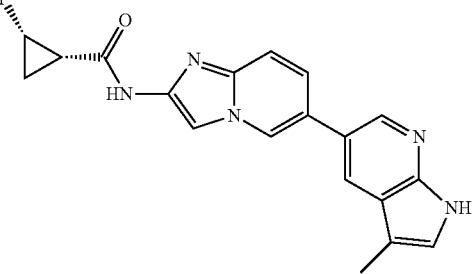<br>(1S,2S)-2-fluoro-N-(6-(3-methyl-1H-pyrrolo[2,3-b]pyridin-5-yl)imidazo[1,2-a]pyridin-2-yl)cyclopropane-1-carboxamide | $^1$H NMR (400 MHz, DMSO-d$_6$) δ 11.35 (s, 1H), 10.99 (s, 1H), 8.91 (d, J = 0.8 Hz, 1H), 8.48 (d, J = 2.0 Hz, 1H), 8.16 (d, J = 2.4 Hz, 1H), 8.07 (s, 1H), 7.61 (dd, J = 9.2, 1.6 Hz, 1H), 7.48 (d, J = 9.2 Hz, 1H), 7.25 (s, 1H), 4.99~4.49 (m, 1H), 2.28 (s, 3H), 2.11 (m, 1H), 1.66~1.60 (m, 1H), 1.16~1.10 (m, 1H); LCMS (electrospray) m/z 350.17 (M + H)+. | G |
| 54 | 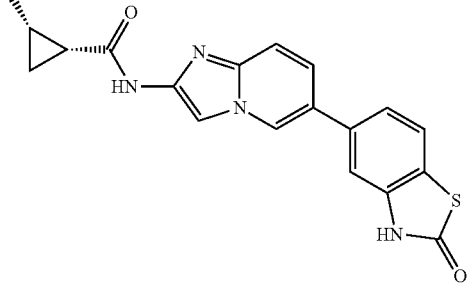<br>(1S,2S)-2-fluoro-N-(6-(2-oxo-2,3-dihydorbenzo[d]thiazol-5-yl)imidazo[1,2-a]pyridin-2-yl)cyclopropane-1-carboxamide | $^1$H NMR (400 MHz, DMSO-d$_6$) δ 11.00 (s, 1H), 8.86 (s, 1H), 7.64 (d, J = 8.4 Hz, 1H), 7.47 (s, 2H), 7.39 (dd, J = 8.4, 1.2 Hz, 1H), 7.30 (s, 1H), 4.99~4.78 (m, 1H), 2.14~2.07 (m, 1H), 1.67~1.59 (m, 1H), 1.17~1.08 (m, 1H); LCMS (electrospray) m/z 369.00 (M + H)+. | G |
| 55 | 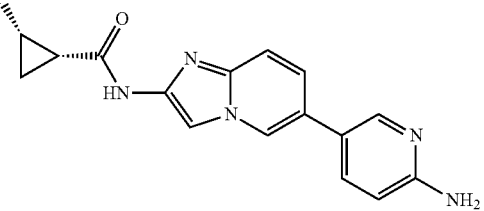<br>(1S,2S)-N-(6-(6-aminopyridin-3-yl)imidazo[1,2-a]pyridin-2-yl)-2-fluorocyclopropane-1-carboxamide | $^1$H NMR (400 MHz, DMSO-d$_6$) δ 10.96 (s, 1H), 8.73 (s, 1H), 8.21 (d, J = 2.4 Hz, 1H), 8.01 (s, 1H), 7.66 (dd, J = 8.8, 2.8 Hz, 1H), 7.42 (s, 2H), 6.51 (s, 1H), 6.06 (s, 2H), 4.98~4.78 (m, 1H), 2.12~2.04 (m, 1H), 1.66~1.58 (m, 1H), 1.16~1.58 (m, 1H); LCMS (electrospray) m/z 311.67 (M + H)+. | G |
| 56 | 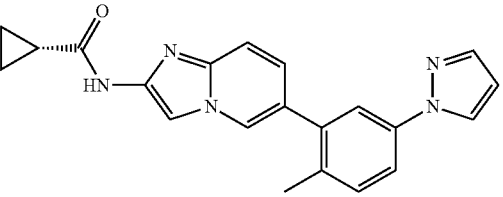<br>(1S,2S)-2-fluoro-N-(6-(2-methyl-5-(1H-pyrazol-1-yl)phenyl)imidazo[1,2-a]pyridin-2-yl)cyclopropane-1-carboxamide | $^1$H NMR (400 MHz, DMSO-d$_6$) δ 11.00 (s, 1H), 8.62 (t, J = 0.8 Hz, 1H), 8.50 (d, J = 2.4 Hz, 1H), 8.08 (s, 1H), 7.77~7.74 (m, 2H), 7.69 (d, J = 2.0 Hz, 1H), 7.47~7.40 (m, 2H), 7.27 (dd, J = 9.2, 2.0 Hz, 1H), 6.50 (t, J = 2.0 Hz, 1H ), 4.99-4.78 (m, 1H), 2.27 (s, 3H), 2.13-2.09 (m, 4H), 1.66-1.58 (m, 1H), 1.15-1.09 (m, 1H); LCMS (electrospray) m/z 376.13 (M + H)+. | D |

TABLE 1-continued

Compounds of Examples

| Ex # | Structure/Name | 1H NMR/MS (M + 1) | Synthetic Method |
|---|---|---|---|
| 57 | 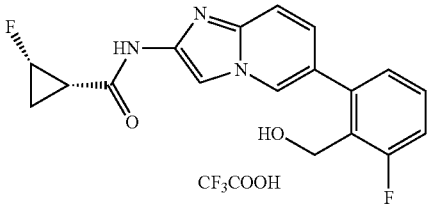<br>(1S,2S)-2-fluoro-N-(6-(3-fluoro-2-(hydroxymethyl)phenyl)imidazo[1,2-a]pyridin-2-yl)cyclopropane-1-carboxamide. 1TFA salt | $^1$H NMR (400 MHz, DMSO-d$_6$) δ 11.34 (br s, 1H), 8.74 (s, 1H), 8.14 (s, 1H), 7.66-7.55 (m, 2H), 7.46 (dt, J = 5.9, 8.0 Hz, 1H), 7.30 (d, J = 8.6 Hz, 1H), 7.28-7.22 (m, 1H), 5.09-4.84 (m, 1H), 4.41 (d, J =1.4 Hz, 2H), 2.20-2.11 (m, 1H), 1.76-1.61 (m, 1H), 1.29-1.13 (m, 1H); LCMS (electrospray) m/z 344.40 (M + H)+. | G |
| 58 | 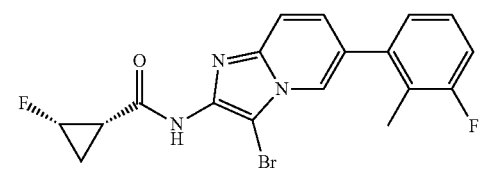<br>(1S,2S)-N-(3-bromo-6-(3-fluoro-2-methylphenyl)imidazo[1,2-a]pyridin-2-yl)-2-fluorocyclopropane-1-carboxamide | 1H NMR (400 MHz, DMSO-d6); δ 10.42 (s, 1H), 8.20 (s, 1H), 7.65 (d, J = 9.6 Hz, 1H), 7.40 (dd, J = 9.2, 1.6 Hz, 1H), 7.39~7.35 (m, 1H), 7.25~7.22 (m, 1H), 5.03~4.86 (m, 1H), 2.17 (d, J = 2.4 Hz, 3H), 2.10~2.05 (m, 1H), 1.66~1.58 (m, 1H), 1.15~1.08 (m, 1H); LCMS (electrospray) m/z 408.00 (M + H)+. | B (NBS reagent) |
| 59 | 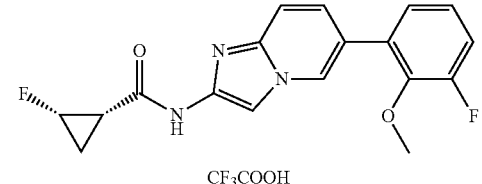<br>(1S,2S)-2-fluoro-N-(6-(3-fluoro-2-methoxyphenyl)imidazo[1,2-a]pyridin-2-yl)cyclopropanecarboxamide. 1 TFA salt | $^1$H NMR (400 MHz, DMSO-d$_6$) δ 11.31 (s, 1H), 8.81 (s, 1H), 8.17 (s, 1H), 7.62-7.57 (m, 2H), 7.35-7.22 (m, 3H), 5.11-4.82 (m, 1H), 3.75 (s, 3H), 2.19-2.09 (m, 1H), 1.72-1.65 (m, 1H), 1.23-1.13 (m, 1H); LCMS (electrospray) m/z 344.1 (M + H)+. | G |
| 60 | 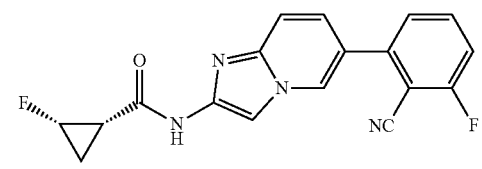<br>(1S,2S)-N-(6-(2-cyano-3-fluorophenyl)imidazo[1,2-a]pyridin-2-yl)-2-fluorocyclopropanecarboxamide. 1 TFA salt | $^1$H NMR (400 MHz, DMSO-d$_6$) δ 11.14 (s, 1H), 8.92 (s, 1H), 8.17 (s, 1H), 7.90-7.88 (m, 1H), 7.65-7.54 (m, 3H), 7.46 (s, 1H), 5.12-4.79 (m, 1H), 2.23-2.12 (m, 1H), 1.76-1.56 (m, 1H), 1.32-1.08 (m, 1H); LCMS (electrospray) m/z 339.1 (M + H)+. | G |
| 61 | 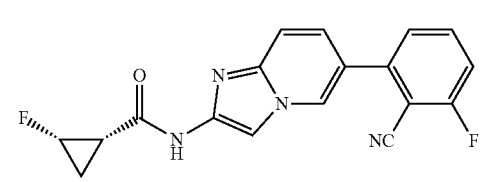<br>(1S,2S)-N-(6-(2-chloro-3-fluorophenyl)imidazo[1,2-a]pyridin-2-yl)-2-fluorocyclopropanecarboxamide. 1 TFA salt | $^1$H NMR (400 MHz, DMSO-d$_6$) δ 11.14 (s, 1H), 8.74 (s, 1H), 8.14 (s, 1H), 7.58-7.49 (m, 3H), 7.40-7.39 (m, 2H), 5.11-4.78 (m, 1H), 2.17-2.12 (m, 1H), 1.70-1.63 (m, 1H), 1.21-1.15 (m, 1H); LCMS (electrospray) m/z 348.0 (M + H)+. | G |

TABLE 1-continued

Compounds of Examples

| Ex # | Structure/Name | 1H NMR/MS (M + 1) | Synthetic Method |
|---|---|---|---|
| 62 | 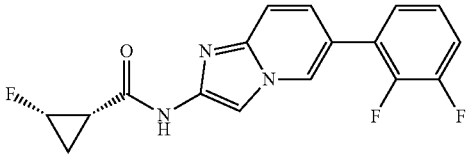<br>(1S,2S)-N-(6-(2,3-difluorophenyl)imidazo[1,2-a]pyridin-2-yl)-2-fluorocyclopropanecarboxamide. 1 TFA salt | $^1$H NMR (400 MHz, DMSO-$d_6$) δ 11.16 (s, 1H), 8.89 (s, 1H), 8.16 (s, 1H), 7.60-7.57 (m, 1H), 7.52-7.44 (m, 3H), 7.42-7.36 (m, 1H), 5.09-4.85 (m, 1H), 2.17-2.13 (m, 1H), 1.78-1.63 (m, 1H), 1.21-1.16 (m, 1H); LCMS (electrospray) m/z 332.1 (M + H)+. | G |
| 63 | 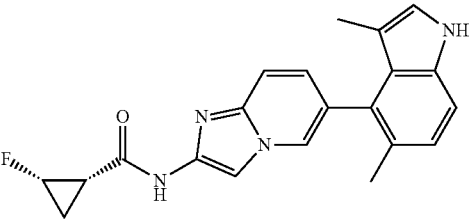<br>(1S,2S)-N-(6-(3,5-dimethyl-1H-indol-4-yl)imidazo[1,2-a]pyridin-2-yl)-2-fluorocyclopropanecarboxamide. 2 TFA salt | $^1$H NMR (400 MHz, DMSO-$d_6$) δ 11.20 (s, 1H), 10.75 (s, 1H), 8.45 (s, 1H), 8.11 (s, 1H), 7.55 (d, J = 8.8 Hz, 1H), 7.32-7.24 (m, 2H), 7.05-6.99 (m, 2H), 5.05-4.85 (m, 1H), 2.19-2.16 (m, 1H), 2.14 (d, J = 2.9 Hz, 3H), 1.73-1.66 (m, 1H), 1.63 (dd, J = 0.7, 4.4 Hz, 3H), 1.25-1.12 (m, 1H); LCMS (electrospray) m/z 363.2 (M + H)+. | G |
| 64 | 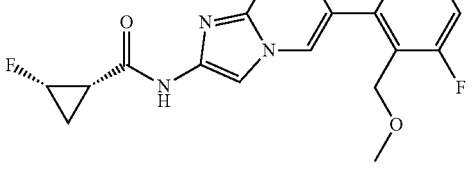<br>(1S,2S)-2-fluoro-N-(6-(3-fluoro-2-(methoxymethyl)phenyl)imidazo[1,2-a]pyridin-2-yl)cyclopropanecarboxamide. 1 TFA salt | $^1$H NMR (400 MHz, DMSO-$d_6$) δ 11.25 (s, 1H), 8.68 (s, 1H), 8.14 (s, 1H), 7.60 (d, J = 9.2 Hz, 1H), 7.52 (dt, J = 6.0, 7.9 Hz, 1H), 7.44 (dd, J = 1.6, 9.2 Hz, 1H), 7.33 (d, J = 8.7 Hz, 1H), 7.30-7.25 (m, 1H), 5.11-4.76 (m, 1H), 4.30 (br d, J = 1.3 Hz, 2H), 3.25 (s, 3H), 2.23-2.08 (m, 1H), 1.76-1.59 (m, 1H), 1.20 (tdd, J = 6.3, 9.1, 12.4 Hz, 1H); LCMS (electrospray) m/z 358.5 (M + H)+. | H |
| 65 | 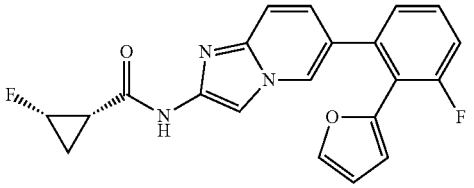<br>(1S,2S)-2-fluoro-N-(6-(3-fluoro-2-(furan-2-yl)phenyl)imidazo[1,2-a]pyridin-2-yl)cyclopropanecarboxamide. 1 TFA salt | $^1$H NMR (400 MHz, DMSO-$d_6$) δ 11.20 (s, 1H), 8.61 (s, 1H), 8.08 (s, 1H), 7.61 (dd, J = 0.9, 1.6 Hz, 1H), 7.60-7.54 (m, 1H), 7.45-7.41 (m, 1H), 7.40-7.36 (m, 2H), 6.93 (dd, J = 1.3, 9.3 Hz, 1H), 6.56-6.48 (m, 2H), 5.05-4.83 (m, 1H), 2.19-2.09 (m, 1H), 1.75-1.59 (m, 1H), 1.19 (tdd, J = 6.3, 9.1, 12.4 Hz, 1H); LCMS (electrospray) m/z 380.5 (M + H)+. | I |

TABLE 1-continued

Compounds of Examples

| Ex # | Structure/Name | 1H NMR/MS (M + 1) | Synthetic Method |
|------|----------------|-------------------|------------------|
| 66 | <br>CF₃COOH<br>(1S,2S)-2-fluoro-N-(6-(3-fluoro-2-(methylthio)phenyl)imidazo[1,2-a]pyridin-2-yl)cyclopropanecarboxamide. 1 TFA salt | ¹H NMR (400 MHz, DMSO-$d_6$) δ 11.16 (s, 1H), 8.65 (s, 1H), 8.13 (s, 1H), 7.56-7.50 (m, 1H), 7.50-7.45 (m, 1H), 7.41-7.33 (m, 2H), 7.29 (dd, J = 1.0, 7.6 Hz, 1H), 5.05-4.82 (m, 1H), 2.28 (s, 3H), 2.21-2.09 (m, 1H), 1.77-1.59 (m, 1H), 1.26-1.11 (m, 1H); LCMS (electrospray) m/z 360.1 (M + H)+. | G |
| 67 | 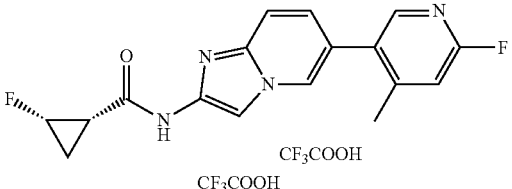<br>CF₃COOH<br>CF₃COOH<br>(1S,2S)-2-fluoro-N-(6-(6-fluoro-4-methylpyridin-3-yl)imidazo[1,2-a]pyridin-2-yl)cyclopropanecarboxamide. 2 TFA salt | ¹H NMR (400 MHz, DMSO-$d_6$) δ 11.21 (s, 1H), 8.69 (s, 1H), 8.13 (m, 1H), 8.12 (s, 1H), 7.62-7.55 (m, 1H), 7.43-7.35 (m, 1H), 7.25-7.20 (m, 1H), 5.06-5.03 (m, 1H), 4.89-4.86 (m, 1H), 2.38 (s, 3H), 2.22-2.11 (m, 1H), 1.76-1.59 (m, 1H), 1.26-1.13 (m, 1H; LCMS (electrospray) m/z 329.1 (M + H)+. | G |
| 68 | 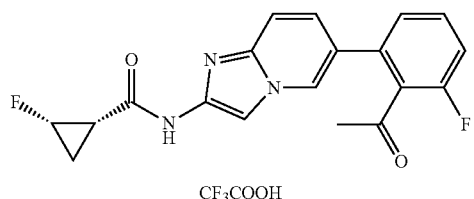<br>CF₃COOH<br>(1S,2S)-N-(6-(2-acetyl-3-fluorophenyl)imidazo[1,2-a]pyridin-2-yl)-2-fluorocyclopropanecarboxamide. 1 TFA salt | ¹H NMR (400 MHz, DMSO-$d_6$) δ 11.18 (s, 1H), 8.66 (br s, 1H), 8.15 (s, 1H), 7.67-7.58 (m, 1H), 7.53 (d, J = 9.2 Hz, 1H), 7.41 (t, J = 9.2 Hz, 1H), 7.36 (dd, J = 0.7, 7.7 Hz, 1H), 7.25-7.18 (m, 1H), 5.03 (td, J = 3.1, 6.2 Hz, 1H), 4.88-4.85 (m, 1H), 2.40 (s, 3H), 2.20-2.09 (m, 1H), 1.74-1.60 (m, 1H), 1.25-1.12 (m, 1H); LCMS (electrospray) m/z 356.1 (M + H)+. | G |
| 69 | 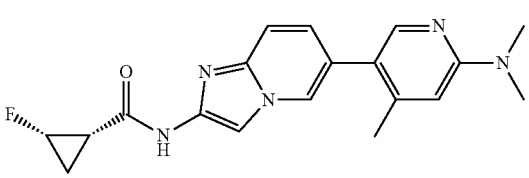<br>(1S,2S)-N-(6-(6-(dimethylamino-4-methylpyridin-3-yl)imidazo[1,2-a]pyridin-2-yl)-2-fluorocyclopropanecarboxamide | ¹H NMR (400 MHz, DMSO-$d_6$) δ 11.00 (s, 1H), 8.55 (s, 1H), 8.08 (s, 1H), 7.96 (s, 1H), 7.44 (d, J = 9.2 Hz, 1H), 7.20 (dd, J = 9.2, 1.6 Hz, 1H), 6.60 (s, 1H), 5.01-4.82 (m, 1H), 3.05 (s, 6H), 2.23 (s, 3H), 2.18-2.09 (m, 1H), 1.73-1.58 (m, 1H), 1.22-1.08 (m, 1H); LCMS (electrospray) m/z 354.2 (M + H)+. | G |
| 70 | 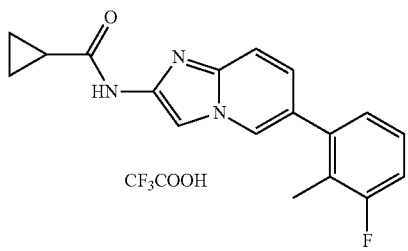<br>CF₃COOH<br>N-(6-(3-fluoro-2-methylphenyl)imidazo[1,2-a]pyridin-2-yl)cyclopropanecarboxamide. 1 TFA salt | ¹H NMR (400 MHz, DMSO-$d_6$) δ 11.22 (br s, 1H), 8.66 (s, 1H), 8.09 (s, 1H), 7.59 (d, J = 9.2 Hz, 1H), 7.40 (br d, J = 9.3 Hz, 1H), 7.38-7.30 (m, 1H), 7.28-7.21 (m, 1H), 7.17 (d, J = 7.5 Hz, 1H), 2.18 (d, J = 2.3 Hz, 3H), 1.94 (quin, J = 6.2 Hz, 1H), 0.85 (d, J = 6.1 Hz, 4H); LCMS (electrospray) m/z 310.1 (M + H)+. | J |

TABLE 1-continued

Compounds of Examples

| Ex # | Structure/Name | 1H NMR/MS (M + 1) | Synthetic Method |
|---|---|---|---|
| 71 | 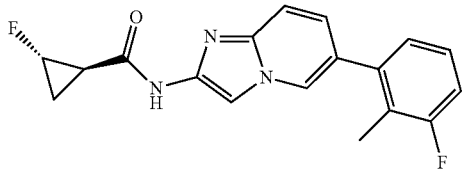<br>CF₃COOH<br>(1R,2S)-2-fluoro-N-(6-(3-fluoro-2-methylphenyl)imidazo[1,2-a]pyridin-2-yl)cyclopropanecarboxamide. 1 TFA salt | ¹H NMR (400 MHz, DMSO-d₆) δ 11.34 (s, 1H), 8.65 (s, 1H), 8.09 (s, 1H), 7.58 (d, J = 9.2 Hz, 1H), 7.40-7.35 (m, 1H), 7.35-7.30 (m, 1H), 7.28-7.20 (m, 1H), 7.17 (d, J = 7.5 Hz, 1H), 5.03-4.80 (m, 1H), 2.53-2.42 (m, 1H), 2.18 (d, J = 2.2 Hz, 3H), 1.62-1.49 (m, 1H), 1.27 (qd, J = 6.5, 13.1 Hz, 1H); LCMS (electrospray) m/z 328.1 (M + H)+. | J |
| 72 | 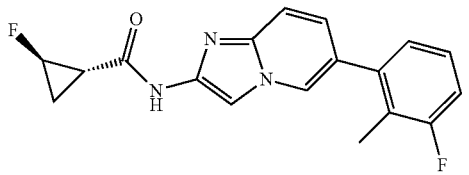<br>CF₃COOH<br>(1S,2R)-2-fluoro-N-(6-(3-fluoro-2-methylphenyl)imidazo[1,2-a]pyridin-2-yl)cyclopropanecarboxamide. 1 TFA salt | ¹H NMR (400 MHz, DMSO-d₆) δ 11.31 (s, 1H), 8.64 (d, J = 0.6 Hz, 1H), 8.08 (s, 1H), 7.56 (d, J = 9.1 Hz, 1H), 7.38-7.30 (m, 2H), 7.27-7.21 (m, 1H), 7.17 (d, J = 7.5 Hz, 1H), 5.03-4.81 (m, 1H), 2.54-2.42 (m, 1H), 2.18 (d, J = 2.3 Hz, 3H), 1.62-1.49 (m, 1H), 1.26 (qd, J = 6.5, 13.1 Hz, 1H); LCMS (electrospray) m/z 328.5 (M + H)+. | J |
| 73 | 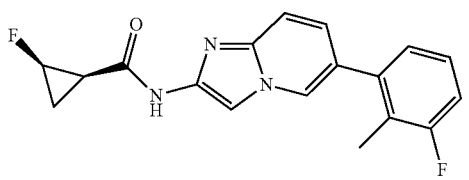<br>CF₃COOH<br>(1R,2R)-2-fluoro-N-(6-(3-fluoro-2-methylphenyl)imidazo[1,2-a]pyridin-2-yl)cyclopropanecarboxamide. 1 TFA salt | ¹H NMR (400 MHz, DMSO-d₆) δ 11.27 (s, 1H), 8.67 (s, 1H), 8.13 (s, 1H), 7.59 (d, J = 9.2 Hz, 1H), 7.40 (dd, J = 1.6, 9.2 Hz, 1H), 7.38-7.31 (m, 1H), 7.28-7.21 (m, 1H), 7.18 (d, J = 7.5 Hz, 1H), 5.07-4.85 (m, 1H), 2.18 (d, J = 2.2 Hz, 3H), 2.16-2.12 (m, 1H), 1.74-1.61 (m, 1H), 1.20 (tdd, J = 6.2, 9.1, 12.5 Hz, 1H); LCMS (electrospray) m/z 328.1 (M + H)+. | J |
| 74 | 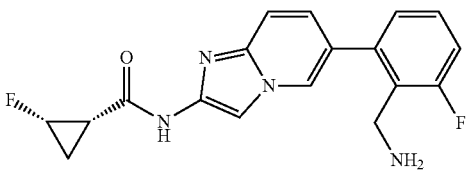<br>CF₃COOH   CF₃COOH<br>(1S,2S)-N-(6-(2-(aminomethyl)-3-fluorophenyl)imidazo[1,2-a]pyridin-2-yl)-2-fluorocyclopropanecarboxamide. 2 TFA salt | ¹H NMR (400 MHz, DMSO-d₆) δ 11.15 (s, 1H), 8.61 (s, 1H), 8.14 (s, 1H), 8.13-8.10 (m, 2H), 7.62-7.56 (m, 2H), 7.46-7.43 (m, 1H), 7.31-7.29 (m, 2H), 5.05-5.01 (m, 0.5H), 4.88-4.86 (m, 0.5H), 4.06-4.04 (m, 2H), 2.18-2.14 (m, 1H), 1.69-1.63 (m, 1H), 1.21-1.16 (m, 1H); LCMS (electrospray) m/z 343.2 (M + H)+. | G |
| 75 | 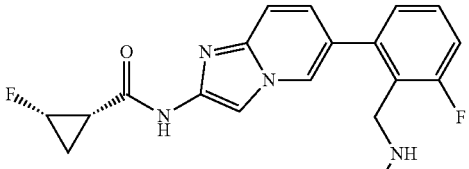<br>CF₃COOH<br>(1S,2S)-N-(6-(2-(acetaminomethyl)-3-fluorophenyl)imidazo[1,2-a]pyridin-2-yl)-2-fluorocyclopropanecarboxamide. 2 TFA salt | ¹H NMR (400 MHz, CD3OD) δ = 8.67 (s, 1H), 7.81-7.71 (m, 2H), 7.49-7.47 (m, 1H), 7.31-7.22 (m, 2H), 5.04-5.01 (m, 0.5H), 4.87-4.85 (m, 0.5H), 4.38 (s, 2H), 2.16-2.12 (m, 1H), 1.90-1.84 (m, 1H), 1.31-1.28 (m, 1H); LCMS (electrospray) m/z 385.1 (M + H)+. | K |

TABLE 1-continued

Compounds of Examples

| Ex # | Structure/Name | 1H NMR/MS (M + 1) | Synthetic Method |
|---|---|---|---|
| 76 | 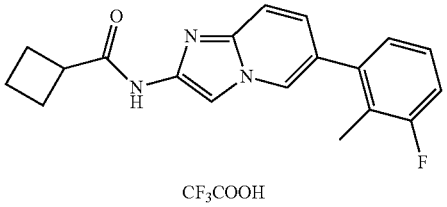<br>CF₃COOH<br>N-(6-(3-fluoro-2-methylphenyl)imidazo[1,2-a]pyridin-2-yl)cyclopropanecarboxamide. 1 TFA salt | ¹H NMR (400 MHz, DMSO-d₆) δ 10.80 (s, 1H), 8.69 (s, 1H), 8.15 (s, 1H), 7.59 (d, J = 9.1 Hz, 1H), 7.41 (dd, J = 1.5, 9.3 Hz, 1H), 7.38-7.31 (m, 1H), 7.29-7.21 (m, 1H), 7.18 (d, J = 7.5 Hz, 1H), 3.35 (quin, J = 8.3 Hz, 1H), 2.30-2.20 (m, 2H), 2.18 (d, J = 2.3 Hz, 3H), 2.17-2.07 (m, 2H), 2.02-1.90 (m, 1H), 1.88-1.77 (m, 1H); LCMS (electrospray) m/z 324.5 (M + H)+. | J |
| 77 | 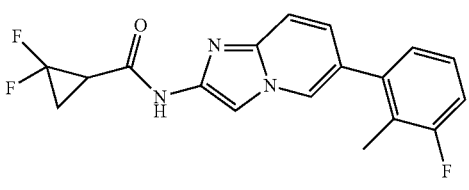<br>CF₃COOH<br>2,2-difluoro-N-(6-(3-fluoro-2-methylphenyl)imidazo[1,2-a]pyridin-2-yl)cyclopropanecarboxamide. 1 TFA salt | ¹H NMR (400 MHz, DMSO-d₆) δ 11.35 (s, 1H), 8.64 (s, 1H), 8.14 (s, 1H), 7.56 (d, J = 9.1 Hz, 1H), 7.38-7.29 (m, 2H), 7.28-7.21 (m, 1H), 7.18 (d, J = 7.5 Hz, 1H), 2.93 (ddd, J = 8.3, 10.7, 13.5 Hz, 1H), 2.18 (d, J = 2.3 Hz, 3H), 2.11-1.96 (m, 2H); LCMS (electrospray) m/z 364.4 (M + H)+. | J |
| 78 | 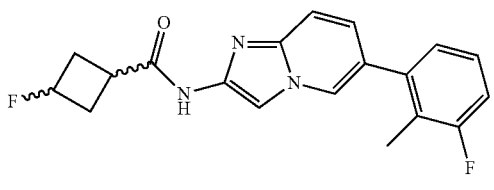<br>CF₃COOH<br>3-fluoro-N-(6-(3-fluoro-2-methylphenyl)imidazo[1,2-a]pyridin-2-yl)cyclopropanecarboxamide. 1 TFA salt | ¹H NMR (400 MHz, DMSO-d₆) δ 11.01 (s, 2H), 8.68 (d, J = 0.9 Hz, 2H), 8.17 (d, J = 4.1 Hz, 2H), 7.58 (dd, J = 2.0, 9.1 Hz, 2H), 7.42-7.37 (m, 2H), 7.36-7.31 (m, 2H), 7.28-7.21 (m, 2H), 7.18 (d, J = 7.5 Hz, 2H), 5.37-5.15 (m, 1H), 5.14-4.92 (m, 1H), 3.41-3.29 (m, 1H), 2.88-2.76 (m, 1H), 2.61-2.52 (m, 4H), 2.49-2.26 (m, 4H), 2.18 (d, J = 2.1 Hz, 6H); LCMS (electrospray) m/z 342.5 (M + H)+. | J |
| 79 | 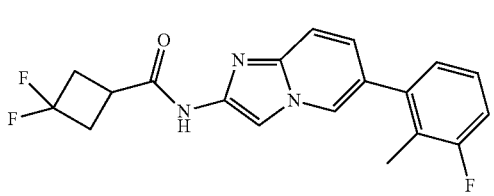<br>CF₃COOH<br>3,3-difluoro-N-(6-(3-fluoro-2-methylphenyl)imidazo[1,2-a]pyridin-2-yl)cyclopropanecarboxamide. 1 TFA salt | ¹H NMR (400 MHz, DMSO-d₆) δ 11.10 (s, 1H), 8.67 (s, 1H), 8.18 (s, 1H), 7.56 (d, J = 9.3 Hz, 1H), 7.39-7.30 (m, 2H), 7.27-7.21 (m, 1H), 7.18 (d, J = 7.5 Hz, 1H), 3.23 (dquin, J = 3.3, 8.4 Hz, 1H), 2.88-2.75 (m, 4H), 2.18 (d, J = 2.3 Hz, 3H); LCMS (electrospray) m/z 360.5 (M + H)+. | J |
| 80 | 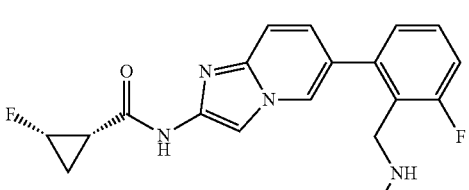<br>CF₃COOH CF₃COOH<br>(1S,2S)-2-fluoro-N-(6-(3-fluoro-2-((methylamino) methyl) phenyl) imidazo[1,2-a]pyridin-2-yl) cyclopropanecarboxamide. 2 TFA salt | ¹H NMR (400 MHz, DMSO-d₆) δ 11.22 (s, 1H), 8.75 (br s, 2H), 8.64 (s, 1H), 8.14 (s, 1H), 7.63-7.60 (m, 2H), 7.50-7.40 (m, 1H), 7.34-7.30 (m, 1H), 5.05-5.03 (m, 0.5H), 4.88-4.84 (m, 0.5H), 4.19 (s, 2H), 2.47 (s, 3H), 2.18-2.14 (m, 1H), 1.70-1.63 (m, 1H), 1.22-1.16 (m, 1H); LCMS (electrospray) m/z 357.2 (M + H)+. | G |

TABLE 1-continued

Compounds of Examples

| Ex # | Structure/Name | 1H NMR/MS (M + 1) | Synthetic Method |
|---|---|---|---|
| 81 | 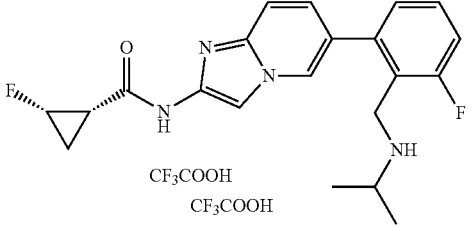<br>(1S,2S)-2-fluoro-N-(6-(3-fluoro-2-((isopropylamino)methyl)phenyl)imidazo[1,2-a]pyridin-2-yl)cyclopropanecarboxamide. 2 TFA salt | $^1$H NMR (400 MHz, DMSO-d$_6$) δ 11.15 (s, 1H), 8.64 (s, 1H), 8.60 (br s, 2H), 8.15 (s, 1H), 7.62-7.59 (m, 2H), 7.50-7.40 (m, 2H), 7.33-7.30 (m, 2H), 5.05-5.03 (m, 0.5H), 4.87-4.86 (m, 0.5H), 4.18 (m, 2H), 3.31-3.25 (m, 1H), 2.18-2.15 (m, 1H), 1.71-1.60 (m, 1H), 1.21-1.16 (m, 1H), 1.12 (d, J = 6.8 Hz, 6 H); LCMS (electrospray) m/z 385.2 (M + H)+. | G |
| 82 | 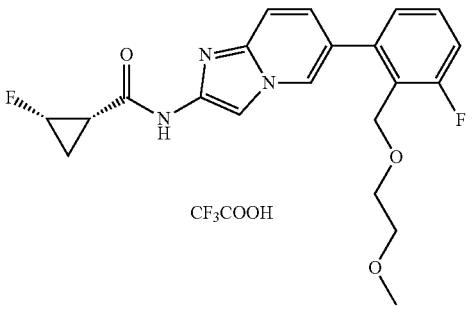<br>(1S,2S)-2-fluoro-N-(6-(3-fluoro-2-((2-methoxyethoxy)methyl)phenyl)imidazo[1,2-a]pyridin-2-yl)cyclopropanecarboxamide. 1 TFA salt | $^1$H NMR (400 MHz, DMSO-d$_6$) δ 11.23-11.19 (br s, 1H), 8.72 (s, 1H), 8.10 (s, 1H), 7.56-7.50 (m, 3H), 7.32-7.28 (m, 2H), 5.04-4.84 (m, 1H), 4.35 (s, 2H), 3.47-3.44 (m, 4H), 3.25 (s, 3H), 2.16-2.11 (m, 1H), 1.70-1.64 (m, 1H), 1.21-1.16 (m, 1H); LCMS (electrospray) m/z 402.0 (M + H)+. | L |
| 83 | 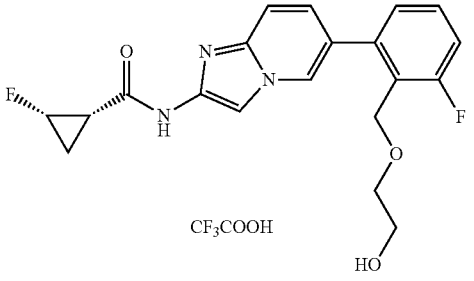<br>(1S,2S)-2-fluoro-N-(6-(3-fluoro-2-((2-hydroxyethoxy)methyl)phenyl)imidazo[1,2-a]pyridin-2-yl)cyclopropanecarboxamide. 1 TFA salt | $^1$H NMR (400 MHz, DMSO-d$_6$) δ 11.21 (s, 1H), 8.78 (s, 1H), 8.14 (s, 1H), 7.58-7.47 (m, 3H), 7.33-7.29 (m, 2H), 5.05-4.85 (m, 1H), 4.36 (s, 2H), 3.55-3.52 (m, 2H), 3.47-3.45 (m, 2H), 2.16-2.13 (m, 1H), 1.71-1.69 (m, 1H), 1.65-1.64 (m, 1H); LCMS (electrospray) m/z 387.9 (M + H)+. | M |
| 84 | (1S,2S)-N-(6-(2-((dimethylamino)methyl)-3-fluorophenyl)imidazo[1,2-a]pyridin-2-yl)2-fluorocyclopropanecarboxamide. 2 TFA salt | $^1$H NMR (400 MHz, CD3OD) δ 8.65 (s, 1H), 7.74-7.70 (m, 2H), 7.60-7.55 (m, 1H), 7.48-7.38 (m, 2H), 5.05-5.00 (m, 0.5H), 4.86-4.84 (m, 0.5H), 4.53 (s, 2H), 2.74 (s, 6H), 2.16 (br s, 1H), 1.87-1.81 (m, 1H), 1.31-1.25 (m, 1H); LCMS (electrospray) m/z 371.2 (M + H)+. | G |

TABLE 1-continued

Compounds of Examples

| Ex # | Structure/Name | 1H NMR/MS (M + 1) | Synthetic Method |
|---|---|---|---|
| 85 | 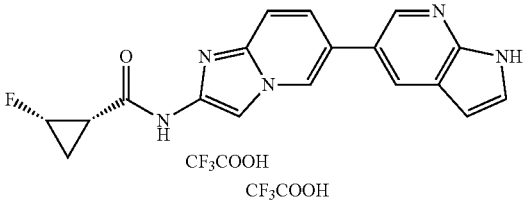<br>(1S,2S)-N-(6-(2-((dimethylamino)methyl)-yl)imidazo[1,2-a]pyridin-2-yl)-2-fluorocyclopropanecarboxamide. 2 TFA salt | $^1$H NMR (400 MHz, DMSO-$d_6$) δ = 11.86 (s, 1H), 11.40 (s, 1H), 9.07 (s, 1H), 8.58 (d, J = 2.1 Hz, 1H), 8.30 (d, J = 1.9 Hz, 1H), 8.14 (s, 1H), 7.91-7.83 (m, 1H), 7.75-7.65 (m, 1H), 7.60-7.55 (m, 1H), 6.60-6.53 (m, 1H), 5.10-4.87 (m, 1H), 2.23-2.12 (m, 1H), 1.78-1.63 (m, 1H), 1.30-1.16 (m, 1H); LCMS (electrospray) m/z 336.1 (M + H)+. | G |
| 86 | 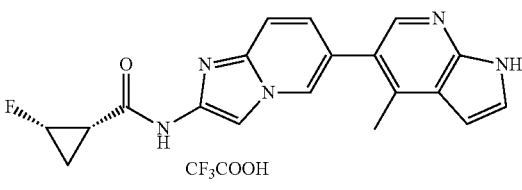<br>(1S,2S)-2-fluoro-N-(6-(4-methyl-1H-pyrrolo[2,3-b]pyridin-5-yl)imidazo[1,2-a]pyridin-2-yl)cyclopropanecarboxamide. 2 TFA salt | $^1$H NMR (400 MHz, DMSO-$d_6$) δ 11.94 (s, 1H), 11.48 (s, 1H), 8.76 (s, 1H), 8.20 (s, 1H), 8.18-8.14 (m, 1H), 7.77-7.65 (m, 1H), 7.60 (dd, J = 1.6, 9.2 Hz, 1H), 7.58-7.54 (m, 1H), 6.72-6.59 (m, 1H), 5.11-4.80 (m, 1H), 2.52 (s, 3H), 2.25-2.08 (m, 1H), 1.80-1.58 (m, 1H), 1.34-1.11 (m, 1H); LCMS (electrospray) m/z 350.1 (M + H)+. | G |
| 87 | 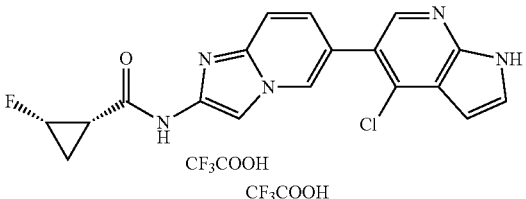<br>(1S,2S)-N-(6-(4-chloro-1H-pyrrolo[2,3-b]pyridin-5-yl)imidazo[1,2-a]pyridin-2-yl)-2-fluorocyclopropanecarboxamide. 2 TFA salt | $^1$H NMR (400 MHz, DMSO-$d_6$) δ 12.18 (s, 1H), 11.24 (s, 1H), 8.78 (s, 1H), 8.29 (s, 1H), 8.15 (s, 1H), 7.72-7.66 (m, 1H), 7.64-7.59 (m, 1H), 7.54-7.49 (m, 1H), 6.59 (dd, J = 1.9, 3.4 Hz, 1H), 5.10-4.84 (m, 1H), 2.21-2.13 (m, 1H), 1.78-1.59 (m, 1H), 1.31-1.09 (m, 1H); LCMS (electrospray) m/z 370.1 (M + H)+. | G |
| 88 | 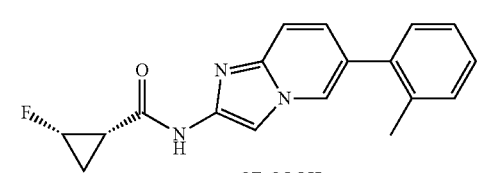<br>(1S,2S)-2-fluoro-N-(6-(o-tolyl)imidazo[1,2-a]pyridin-2-yl)cyclopropanecarboxamide. 1 TFA salt | $^1$H NMR (400 MHz, DMSO-$d_6$) δ 11.26 (s, 1H), 8.64 (s, 1H), 8.12 (s, 1H), 7.58 (d, J = 9.2 Hz, 1H), 7.41 (br d, J = 9.0 Hz, 1H), 7.36-7.27 (m, 4H), 5.08-4.84 (m, 1H), 2.28 (s, 3H), 2.19-2.10 (m, 1H), 1.74-1.62 (m, 1H), 1.25-1.16 (m, 1H); LCMS (electrospray) m/z 310.1 (M + H)+. | G |
| 89 | 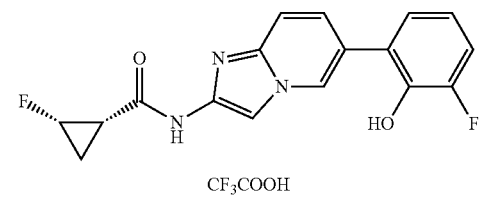<br>(1S,2S)-2-flouro-N-(6-(3-fluoro-2-hydroxyphenyl)imidazo[1,2-a]pyridin-2-yl)cyclopropanecarboxamide. 1 TFA salt | $^1$H NMR (400 MHz, DMSO-$d_6$) δ 32 11.22 (s, 1H), 9.94-9.83 (m, 1H), 8.79 (s, 1H), 8.13 (s, 1H), 7.57 (s, 2H), 7.24 (br d, J = 8.9 Hz, 1H), 7.19 (br d, J = 7.9 Hz, 1H), 6.93 (dt, J = 5.3, 7.9 Hz, 1H), 5.08-4.83 (m, 1H), 2.21-2.09 (m, 1H), 1.76-1.60 (m, 1H), 1.27-1.12 (m, 1H); LCMS (electrospray) m/z 329.8 (M + H)+. | G |

TABLE 1-continued

Compounds of Examples

| Ex # | Structure/Name | 1H NMR/MS (M + 1) | Synthetic Method |
|---|---|---|---|
| 90 | <br>CF₃COOH<br><br>(1S,2S)-N-(6-(2-amino-3-fluorophenyl)imidazo[1,2-a]pyridin-2-yl)-2-fluorocyclopropanecarboxamide. 1 TFA salt | ¹H NMR (400 MHz, DMSO-d₆) δ 11.31 (s, 1H), 8.69 (s, 1H), 8.12 (s, 1H), 7.62 (d, J = 9.0 Hz, 1H), 7.45 (br d, J = 9.2 Hz, 1H), 7.09 (ddd, J = 1.4, 8.1, 11.4 Hz, 1H), 6.93 (d, J = 7.5 Hz, 1H), 6.66 (dt, J = 5.3, 7.9 Hz, 1H), 5.11-4.81 (m, 1H), 2.23-2.05 (m, 1H), 1.79-1.59 (m, 1H), 1.34-1.11 (m, 1H); LCMS (electrospray) m/z 328.8 (M + H)+. | G |
| 91 | 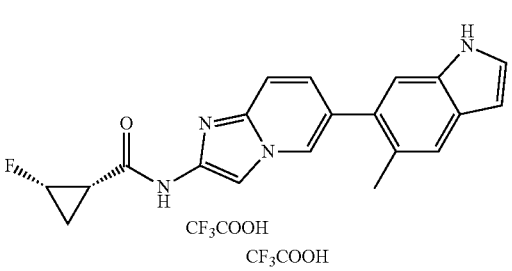<br>CF₃COOH<br>CF₃COOH<br><br>(1S,2S)-2-fluoro-N-(6-(5-methyl-1H-indole-6-yl)imidazo[1,2-a]pyridin-2-yl)cyclopropanecarboxamide. 2 TFA salt | ¹H NMR (400 MHz, DMSO-d₆) δ 1.27 (br s, 1H), 11.08 (br s, 1H), 8.64 (s, 1H), 8.13 (s, 1H), 7.58 (d, J = 9.1 Hz, 1H), 7.45 (br s, 2H), 7.36 (t, J = 2.7 Hz, 1H), 7.29 (s, 1H), 6.39 (t, J = 2.0 Hz, 1H), 5.19-4.74 (m, 1H), 5.35-4.58 (m, 1H), 2.30 (s, 3H), 2.20-2.12 (m, 1H), 1.75-1.63 (m, 1H), 1.26-1.15 (m, 1H); LCMS (electrospray) m/z 348.9 (M + H)+. | G |
| 92 | 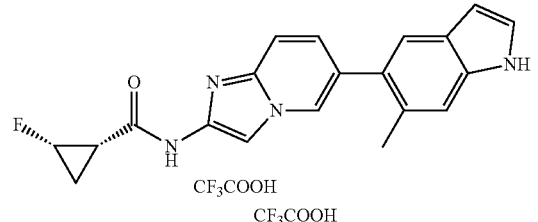<br>CF₃COOH<br>CF₃COOH<br><br>(1S,2S)-2-fluoro-N-(6-(6-methyl-1H-indole-5-yl)imidazo[1,2-a]pyridin-2-yl)cyclopropanecarboxamide. 2 TFA salt | ¹H NMR (400 MHz, DMSO-d₆) δ 11.28-11.20 (m, 1H), 11.05 (br s, 1H), 8.60 (s, 1H), 8.11 (s, 1H), 7.55 (br d, J = 9.4 Hz, 1H), 7.44 (s, 2H), 7.35-7.30 (m, 2H), 6.44-6.39 (m, 1H), 5.09-4.79 (m, 1H), 2.32 (s, 3H), 2.19-2.10 (m, 1H), 1.77-1.56 (m, 1H), 1.29-1.07 (m, 1H); LCMS (electrospray) m/z 348.8 (M + H)+. | G |
| 93 | 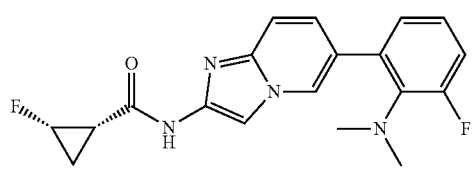<br>CF₃COOH<br><br>(1S,2S)-N-(6-(2-(dimethylamino-3-fluorophenyl)imidazo[1,2-a]pyridin-2-yl)-2-fluorocyclopropanecarboxamide. 1 TFA salt | ¹H NMR (400 MHz, DMSO-d₆) δ 11.30 (br s, 1H), 8.70 (s, 1H), 8.13 (s, 1H), 7.62-7.49 (m, 2H), 7.27-7.16 (m, 3H), 5.07-4.86 (m, 2H), 2.63 (d, J = 2.0 Hz, 6H), 2.20-2.11 (m, 1H), 1.75-1.62 (m, 1H), 1.26-1.14 (m, 1H); LCMS (electrospray) m/z 357.5 (M + H)+. | G |

TABLE 1-continued

Compounds of Examples

| Ex # | Structure/Name | 1H NMR/MS (M + 1) | Synthetic Method |
|---|---|---|---|
| 94 | 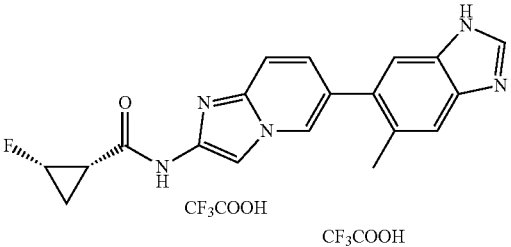<br>(1S,2S)-2-fluoro-N-(6-(5-methyl-1H-benzo[d]imidazol-6-yl)imidazol[1,2-a]pyridin-2-yl)cyclopropanecarboxamide. 2 TFA salt | $^1$H NMR (400 MHz, DMSO-$d_6$) δ 11.14 (s, 1H), 9.45 (s, 1H), 8.64 (s, 1H), 8.14 (s, 1H), 7.80 (s, 1H), 7.74 (s, 1H), 7.55 (d, J = 9.3 Hz, 1H), 7.33 (dd, J = 1.6, 9.3 Hz, 1H), 5.14-4.79 (m, 1H), 2.41 (s, 3H), 2.16 (td, J = 7.1, 14.0 Hz, 1H), 1.74-1.60 (m, 1H), 1.27-1.08 (m, 1H); LCMS (electrospray) m/z 349.9 (M + H)+. | G |
| 95 | 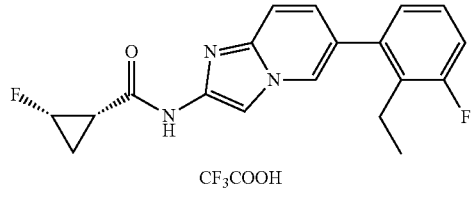<br>(1S,2S)-N-(6-(2-(ethyl-3-fluorophenyl)imidazo[1,2-a]pyridin-2-yl)-2-fluorocyclopropanecarboxamide. 1 TFA salt | $^1$H NMR (400 MHz, DMSO-$d_6$) δ 11.13 (br s, 1H), 8.60 (s, 1H), 8.13 (s, 1H), 7.54 (d, J = 9.0 Hz, 1H), 7.39-7.28 (m, 1H), 7.28-7.20 (m, 2H), 7.15-7.11 (m, 1H), 5.08-4.79 (m, 1H), 2.61-2.53 (m, 2H), 2.23-2.09 (m, 1H), 1.75-1.57 (m, 1H), 1.25-1.12 (m, 1H), 1.05 (t, J = 7.6 Hz, 3H); LCMS (electrospray) m/z 342.1 (M + H)+. | G |
| 96 | 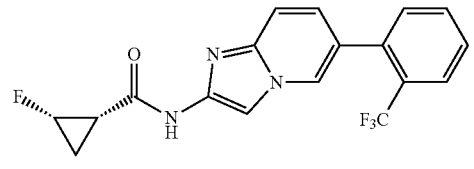<br>(1S,2S)-2-flouro-N-(6-(3-fluoro-2-(trifluoromethyl)pyridin-3-yl)imidazo[1,2-a]pyridin-2-yl)cyclopropanecarboxamide. 1 TFA salt | $^1$H NMR (400 MHz, DMSO-$d_6$) δ 11.20 (s, 1H), 8.62 (s, 1H), 8.12 (s, 1H), 7.89 (d, J = 7.8 Hz, 1H), 7.81-7.74 (m, 1H), 7.72-7.65 (m, 1H), 7.58-7.50 (m, 2H), 7.25 (d, J = 9.2 Hz, 1H), 5.06-4.83 (m, 1H), 2.20-2.10 (m, 1H), 1.75-1.60 (m, 1H), 1.28-1.10 (m, 1H); LCMS (electrospray) m/z 364.0 (M + H)+. | G |
| 97 | 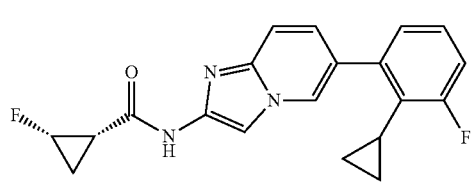<br>(1S,2S)-N-(6-(2-cyclopropyl-3-fluorophenyl)imidazo[1,2-a]pyridin-2-yl)-2-fluorocyclopropanecarboxamide. 1 TFA salt | $^1$H NMR (400 MHz, DMSO-$d_6$) δ 11.16 (br s, 1H), 8.69 (s, 1H), 8.11 (s, 1H), 7.57-7.42 (m, 2H), 7.39-7.32 (m, 1H), 7.24-7.16 (m, 2H), 5.11-4.76 (m, 1H), 2.23-2.07 (m, 1H), 1.99-1.85 (m, 1H), 1.77-1.56 (m, 1H), 1.31-1.05 (m, 1H), 0.80-0.69 (m, 2H), 0.44-0.30 (m, 2H); LCMS (electrospray) m/z 353.9 (M + H)+. | G |

TABLE 1-continued

Compounds of Examples

| Ex # | Structure/Name | 1H NMR/MS (M + 1) | Synthetic Method |
|---|---|---|---|
| 98 | <br>(1S,2S)-2-flouro-N-(6-(3-fluoro-2-(methylamino)phenyl)imidazo[1,2-a]pyridin-2-yl)cyclopropanecarboxamide. 1 TFA salt | $^1$H NMR (400 MHz, DMSO-d$_6$) δ 11.25 (br s, 1H), 8.63 (s, 1H), 8.11 (s, 1H), 7.57 (br d, J = 9.0 Hz, 1H), 7.36 (br d, J = 9.0 Hz, 1H), 7.12 (ddd, J = 1.3, 8.1, 13.0 Hz, 1H), 6.95 (d, J = 7.7 Hz, 1H), 6.77 (dt, J = 5.0, 7.8 Hz, 1H), 5.06-4.85 (m, 1H), 2.66 (d, J = 3.6 Hz, 3H), 2.19-2.09 (m, 1H), 1.74-1.60 (m, 1H), 1.20 (ddd, J = 2.8, 6.2, 12.2 Hz, 1H); LCMS (electrospray) m/z 343.3.00 (M + H)+. | G |
| 99 | 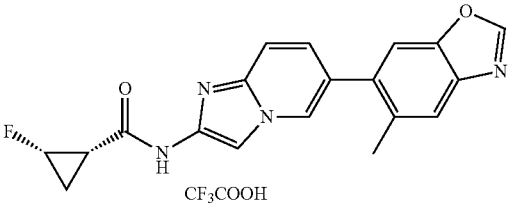<br>(1S,2S)-2-fluoro-N-(6-(5-methylbenzo[d]oxazol-6-yl)imidazol[1,2-a]pyridin-2-yl)cyclopropanecarboxamide. 2 TFA salt | $^1$H NMR (400 MHz, DMSO-d$_6$) δ 11.05 (s, 1H), 8.76 (s, 1H), 8.60 (dd, J = 0.9, 1.6 Hz, 1H), 8.11 (s, 1H), 7.77 (s, 1H), 7.73 (s, 1H), 7.49 (d, J = 9.2 Hz, 1H), 7.27 (dd, J = 1.8, 9.2 Hz, 1H), 5.04-4.82 (m, 1H), 2.36 (s, 3H), 2.19-2.10 (m, 1H), 1.71-1.59 (m, 1H), 1.16 (tdd, J = 6.2, 9.1, 12.3 Hz, 1H); LCMS (electrospray) m/z 351.5 (M + H)+. | G |
| 100 | 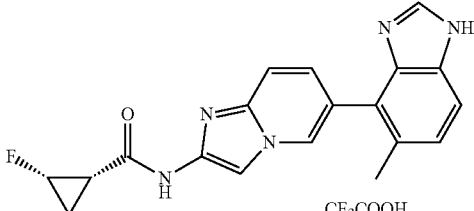<br>(1S,2S)-2-fluoro-N-(6-(5-methyl-1H-benzo[d]imidazol-4-yl)imidazol[1,2-a]pyridin-2-yl)cyclopropane-1-carboxamide. 2 TFA salt | $^1$H NMR (400 MHz, DMSO-d$_6$) δ 11.13 (s, 1H), 9.42 (s, 1H), 8.68 (s, 1H), 8.13 (s, 1H), 7.79 (d, J = 8.4 Hz, 1H), 7.68-7.51 (m, 2H), 7.27 (dd, J = 1.6, 9.0 Hz, 1H), 5.11-4.80 (m, 1H), 2.39-2.37 (s, 3H), 2.19-2.14 (m, 1H), 1.74-1.60 (m, 1H), 1.23-1.12 (m, 1H); LCMS (electrospray) m/z 350.2 (M + H)+. | G |
| 101 | 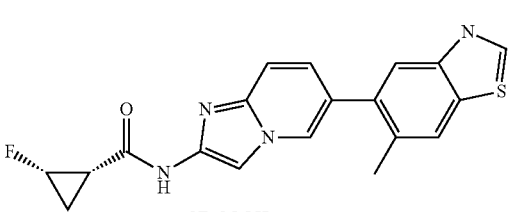<br>(1S,2S)-2-fluoro-N-(6-(5-methylbenzo[d]thiazol-5-yl)imidazol[1,2-a]pyridin-2-yl)cyclopropanecarboxamide. 1 TFA salt | $^1$H NMR (400 MHz, DMSO-d$_6$) δ 11.27 (s, 1H), 9.30 (s, 1H), 8.70 (s, 1H), 8.08-8.05 (m, 2H), 7.67-7.61 (m, 1H), 7.48-7.44 (m, 1H), 7.43-7.39 (m, 1H), 5.06-4.86 (m, 1H), 2.37 (s, 3H), 2.18-2.15 (m, 1H), 1.75-1.60 (m, 1H), 1.23-1.17 (m, 1H); LCMS (electrospray) m/z 367.2 (M + H)+. | G |

TABLE 1-continued

Compounds of Examples

| Ex # | Structure/Name | 1H NMR/MS (M + 1) | Synthetic Method |
|---|---|---|---|
| 102 | 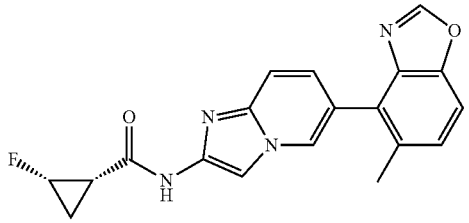<br>(1S,2S)-2-fluoro-N-(6-(5-methylbenzo[d]oxazol-4-yl)imidazol[1,2-a]pyridin-2-yl)cyclopropanecarboxamide | $^1$H NMR (400 MHz, DMSO-$d_6$) δ 11.07 (s, 1H), 8.70 (s, 1H), 8.65 (s, 1H), 8.13 (s, 1H), 7.71 (d, J = 8.3 Hz, 1H), 7.53 (d, J = 9.2 Hz, 1H), 7.43 (d, J = 8.4 Hz, 1H), 7.29 (dd, J = 1.6, 9.2 Hz, 1H), 5.05-4.81 (m, 1H), 2.38 (s, 3H), 2.20-2.10 (m, 1H), 1.73-1.59 (m, 1H), 1.17 (tdd, J = 6.2, 9.1, 12.2 Hz, 1H); LCMS (electrospray) m/z 351.2 (M + H)+. | N |
| 103 | 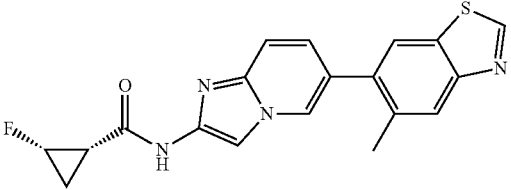<br>(1S,2S)-2-fluoro-N-(6-(5-methylbenzo[d]thiazol-6-yl)imidazo[1,2-a]pyridin-2-yl)cyclopropanecarboxamide | $^1$H NMR (400 MHz, DMSO-$d_6$) δ 11.07 (s, 1H), 9.40 (s, 1H), 8.64 (dd, J = 0.9, 1.6 Hz, 1H), 8.12 (s, 1H), 8.11 (s, 1H), 8.07 (s, 1H), 7.51 (d, J = 9.2 Hz, 1H), 7.30 (dd, J = 1.8, 9.2 Hz, 1H), 5.05-4.82 (m, 1H), 2.42 (s, 3H), 2.21-2.10 (m, 1H), 1.74-1.59 (m, 1H), 1.24-1.12 (m, 1H); LCMS (electrospray) m/z 367.5 (M + H)+. | G |
| 104 | 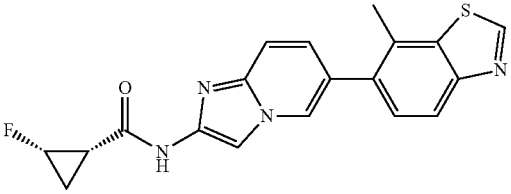<br>(1S,2S)-2-fluoro-N-(6-(7-methylbenzo[d]thiazol-6-yl)imidazo[1,2-a]pyridin-2-yl)cyclopropanecarboxamide | $^1$H NMR (400 MHz, DMSO-$d_6$) δ 11.07 (s, 1H), 9.45 (s, 1H), 8.67-8.61 (m, 1H), 8.13 (s, 1H), 8.03 (d, J = 8.3 Hz, 1H), 7.52 (dd, J = 7.2, 8.7 Hz, 2H), 7.30 (dd, J = 1.8, 9.2 Hz, 1H), 5.05-4.80 (m, 1H), 2.54 (s, 3H), 2.20-2.10 (m, 1H), 1.74-1.59 (m, 1H), 1.24-1.11 (m, 1H); LCMS (electrospray) m/z 367.5 (M + H)+. | G |
| 105 | 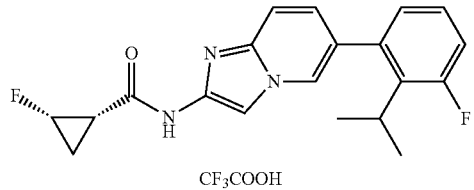<br>CF$_3$COOH<br>(1S,2S)-2-flouro-N-(6-(3-fluoro-2-isopropylphenyl)imidazo[1,2-a]pyridin-2-yl)cyclopropanecarboxamide. 1 TFA salt | $^1$H NMR (400 MHz, DMSO-$d_6$) δ 11.12 (br s, 1H), 8.55 (s, 1H), 8.12 (s, 1H), 7.51 (br d, J = 8.9 Hz, 1H), 7.35-7.27 (m, 1H), 7.26-7.20 (m, 1H), 7.20-7.16 (m, 1H), 7.10 (d, J = 7.3 Hz, 1H), 5.12-4.78 (m, 1H), 3.07-2.82 (m, 1H), 2.22-2.09 (m, 1H), 1.74-1.58 (m, 1H), 1.25 (br d, J = 6.8 Hz, 6H), 1.20-1.13 (m, 1H); LCMS (electrospray) m/z 355.9 (M + H)+. | G |

Evaluation of Compounds c-abl Kinase Assay

ADP-Glo assay kit was purchased from Promega. Magnesium chloride (MgCl2), bovine serum albumin (BSA), ethylene glycol-bis(p-aminoethyl ether)-N,N,N',N'-tetraacetic acid (EGTA), triton X-100, 1,4-dithiothreitol (DTT) and dimethyl sulfoxide (DMSO) were purchased from Sigma-Aldrich. HEPES buffer was purchased from Gibco. ABL1 kinase and Abltide were purchased from Signalchem.

c-Abl kinase activity was measured by Promega's ADP-Glo™ Assay. In this assay, His-tagged recombinant human ABL1 (0.25 ng/μl) is incubated with 5 μL of compounds (0.5% DMSO), 5 μL of Abltide (0.01 μg/μl) and 5 μL of ATP (25 μM) in buffer (50 mM HEPES, 7.5; 10 mM MgCl$_2$; 1 mM EGTA; 0.05% BSA; 0.01% Triton X-100; 2 mM DTT). The assay was started by incubating the reaction mixture in a 96-well plate at 30° C. for 30-min. After the incubation, 25 μL ADP-Glo reagent was added and the reaction was incubated at room temperature for 40-min to stop the reaction and degrade residual ATP. The ADP product was then converted to ATP by adding 50 μL per well of detection reagent. Luminescence was detected after 30-min room temperature incubation with the Molecular device I3X plate reader. The IC$_{50}$ values were calculated from a series of percent inhibition values determined at a range of inhibitor concentration using software routines as implemented in the GraphPad Prism 7 software and Sigma Plot 13.0.

LRRK2 and LRRK2 G2019S Kinase Assay

The LRRK2 and LRRK2 G2019S kinase assays were performed using the Adapta™ technology in ThermoFisher Scientific. This experiment was carried out according to the supplier's protocol. Briefly, assay conditions were as follows. The mixture of substrate (LRRKtide) and each kinase was prepared in 50 mM Tris pH 8.5, 0.01% BRIJ-35, 10 mM $MgCl_2$, 1 mM EGTA, 0.02% $NaN_3$. Assays were performed in the presence of 70 μM ATP and 100 μM ATP (KmATP) in LRRK2 and LRRK2 G2019S, respectively. The reaction was progressed at room temperature for 1 hour. Upon completion of kinase reaction, 5 μL of Detection Mix was added and after 60 min incubation time, the emission ratio of 665/615 nm was calculated.

Table 2 shows $IC_{50}$ values of the invented compounds which represent + for >1000 nM, ++ for 101-1000 nM, +++ for 10-100 nM, ++++ for <10 nM.

TABLE 2

| | In vitro activity | | |
|---|---|---|---|
| Example | c-Abl $IC_{50}$ (nM) | LRRK2 (WT) $IC_{50}$ (nM) | LRRK2_G2019S $IC_{50}$ (nM) |
| 1 | ++++ | +++ | +++ |
| 2 | ++++ | ++ | +++ |
| 3 | +++ | ++ | ++ |
| 4 | +++ | + | ++ |
| 5 | ++ | + | + |
| 6 | +++ | ++ | ++ |
| 7 | ++ | + | + |
| 8 | +++ | ++ | ++ |
| 9 | +++ | ++ | ++ |
| 10 | ++ | + | + |
| 11 | ++++ | +++ | +++ |
| 12 | ++++ | +++ | +++ |
| 13 | ++++ | + | + |
| 14 | ++++ | ++ | ++ |
| 15 | ++++ | ++++ | ++++ |
| 16 | ++ | + | + |
| 17 | ++++ | ++ | ++ |
| 18 | ++ | ++ | ++ |
| 19 | +++ | ++ | ++ |
| 20 | ++++ | ++++ | +++ |
| 21 | +++ | ++ | ++ |
| 22 | ++++ | ++ | ++ |
| 23 | ++++ | ++ | +++ |
| 24 | ++++ | ++ | +++ |
| 25 | +++ | + | ++ |
| 26 | ++++ | ++ | ++ |
| 27 | ++++ | ++ | +++ |
| 28 | ++++ | ++ | ++ |
| 29 | ++++ | ++ | ++ |
| 30 | ++++ | ++ | ++ |
| 31 | ++ | + | ++ |
| 32 | ++++ | ++ | ++ |
| 33 | ++++ | ++ | ++ |
| 34 | ++++ | ++ | ++ |
| 35 | +++ | + | + |
| 36 | ++ | + | ++ |
| 37 | ++++ | ++ | ++ |
| 38 | ++++ | ++ | ++ |
| 39 | ++++ | ++ | +++ |
| 40 | ++++ | ++ | +++ |
| 41 | ++++ | +++ | +++ |
| 42 | ++++ | ++ | ++ |
| 43 | ++++ | ++ | +++ |
| 44 | ++++ | ++ | +++ |
| 45 | ++++ | ++ | +++ |
| 46 | ++++ | ++ | ++ |
| 47 | +++ | ++ | +++ |
| 48 | ++++ | +++ | +++ |
| 49 | ++++ | + | + |
| 50 | ++++ | +++ | +++ |
| 51 | ++++ | + | + |
| 52 | ++++ | ++ | +++ |
| 53 | ++++ | ++ | +++ |
| 54 | +++ | + | ++ |
| 55 | +++ | ++ | ++ |
| 56 | ++++ | ++ | ++ |
| 57 | ++++ | + | + |
| 58 | +++ | Not tested | Not tested |
| 59 | ++++ | +++ | +++ |
| 60 | +++ | +++ | +++ |
| 61 | ++++ | +++ | +++ |
| 62 | ++++ | +++ | +++ |
| 63 | ++++ | ++ | +++ |
| 64 | ++++ | + | ++ |
| 65 | +++ | + | + |
| 66 | ++++ | ++ | +++ |
| 67 | +++ | +++ | +++ |
| 68 | +++ | + | + |
| 69 | ++ | + | + |
| 70 | ++++ | +++ | +++ |
| 71 | ++++ | ++ | +++ |
| 72 | ++++ | +++ | +++ |
| 73 | ++++ | ++ | +++ |
| 74 | + | + | + |
| 75 | ++ | + | + |
| 76 | +++ | +++ | +++ |
| 77 | ++++ | ++ | +++ |
| 78 | +++ | ++ | +++ |
| 79 | +++ | ++ | ++ |
| 80 | + | + | + |
| 81 | + | + | + |
| 82 | +++ | + | ++ |
| 83 | ++ | ++ | + |
| 84 | + | + | + |
| 85 | ++++ | Not tested | Not tested |
| 86 | ++++ | Not tested | Not tested |
| 87 | ++++ | Not tested | Not tested |
| 88 | ++++ | Not tested | Not tested |
| 89 | ++++ | Not tested | Not tested |
| 90 | ++++ | Not tested | Not tested |
| 91 | ++++ | Not tested | Not tested |
| 92 | ++++ | Not tested | Not tested |
| 93 | +++ | Not tested | Not tested |
| 94 | ++++ | Not tested | Not tested |
| 95 | ++++ | Not tested | Not tested |
| 96 | +++ | Not tested | Not tested |
| 97 | ++++ | Not tested | Not tested |
| 98 | ++++ | Not tested | Not tested |
| 99 | ++++ | Not tested | Not tested |
| 100 | +++ | Not tested | Not tested |
| 101 | ++++ | Not tested | Not tested |
| 102 | ++++ | Not tested | Not tested |
| 103 | ++++ | Not tested | Not tested |
| 104 | ++++ | Not tested | Not tested |
| 105 | ++ | Not tested | Not tested |

What is claimed is:

1. A compound of Formula (I) or a pharmaceutically acceptable salt thereof:

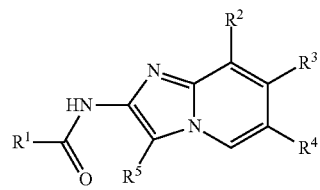

Formula I wherein
R¹ is cyclopropyl substituted with one or more groups selected from the group consisting of halo, alkyl, hydroxyalkyl, haloalkyl, and monoalkylaminoalkyl;
R² and R³ are independently —H, halo, alkyl, alkoxy, —CF₃, —CHF₂, —CH₂F, or —OCF₃;
R⁴ is selected from the group consisting of 6-membered aryl, pyridyl, pyrimidyl, pyranyl, pyridazinyl, pyrazinyl,

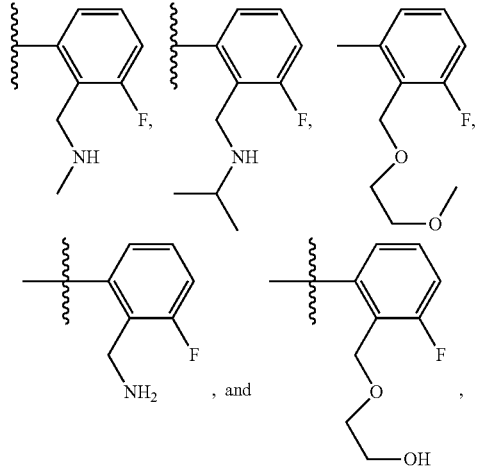

wherein the 6-membered ary, the pyridyl, pyrimidyl, pyranyl, pyridazinyl, or pyrazinyl, is optionally substituted with one or more groups selected from the group consisting of halo, hydroxyl, alkyl, alkenyl, alkynyl, cycloalkyl, haloalkyl, hydroxyalkyl, dialkylaminoalkyl, trimethylsilylethoxymethyl, —CH₂NHC(O)CH₃, —NO₂, —NR$_a$R$_b$, —NR$_a$C(=O)R$_b$, —NR$_a$C(=O)NR$_a$R$_b$, —NR$_a$C(=O)OR$_b$, —OR$_a$, —CN, —C(=O)R$_a$, —C(=O)OR$_a$, —C(=O)NR$_a$R$_b$, —OC(=O)R$_a$, —OC(=O)OR$_a$, —OC(=O)NR$_a$R$_b$, —SR$_a$, azetidinyl, oxetanyl, tetrahydrofuranyl, furanyl, pyrrolidinyl, pyrrolyl, pyrazolyl, thiophenyl, imidazolyl, oxazolyl, isoxazolyl, thiazolyl, furazanyl, oxadiazolyl, thiadiazolyl, phenyl, tetrahydropyranyl, pyranyl, pyridinyl, pyridazinyl, pyrimidinyl, pyrazinyl, piperidinyl, piperazinyl, morpholinyl and thiomorpholinyl;
R$_a$ and R$_b$ are independently —H, halo, amino, alkyl, or haloalkyl; and
R⁵ is H, halo, or alkyl.

2. The compound of claim 1 or a pharmaceutically acceptable salt thereof, wherein
R¹ is cyclopropy substituted with one or more groups selected from the group consisting of halo, $C_1$-$C_3$ alkyl, $C_1$-$C_3$ hydroxyalkyl and $C_1$-$C_3$ haloalkyl;
R² and R³ are independently —H, halo, $C_1$-$C_3$ alkyl, $C_1$-$C_3$ alkoxy, —CF₃, —CHF₂, —CH₂F, or —OCF₃;
R⁴ is 6-membered aryl, pyridyl, pyrimidyl, pyranyl, pyridazinyl, or pyrazinyl, wherein R⁴ is optionally substituted with one or more groups selected from the group consisting of halo, hydroxyl, $C_1$-$C_3$ alkyl, $C_2$-$C_3$ alkenyl, $C_2$-$C_3$ alkynyl, $C_3$-$C_4$ cycloalkyl, $C_1$-$C_3$ haloalkyl, mono-$C_1$-$C_3$ alkylamino, di-$C_1$-$C_3$ alkylamino, —CH₂NHC(O)CH₃, —NO₂, —NR$_a$R$_b$, —NR$_a$C(=O)R$_b$, —NR$_a$C(=O)NR$_a$R$_b$, —NR$_a$C(=O)OR$_b$, —OR$_a$, —CN, —C(=O)R$_a$, —C(=O)OR$_a$, —OC(=O)NR$_a$R$_b$, —OC(=O)R$_a$, —OC(=O)OR$_a$, —OC(=O)NR$_a$R$_b$, —SR$_a$, azetidinyl, oxetanyl, tetrahydrofuranyl, furanyl, pyrrolidinyl, pyrrolyl, pyrazolyl, thiophenyl, imidazolyl, oxazolyl, isoxazolyl, thiazolyl, furazanyl, oxadiazolyl, thiadiazolyl, phenyl, tetrahydropyranyl, pyranyl, pyridinyl, pyridazinyl, pyrimidinyl, pyrazinyl, piperidinyl, piperazinyl, morpholinyl and thiomorpholinyl;
R$_a$ and R$_b$ are independently —H, halo, amino, $C_1$-$C_3$ alkyl, or $C_1$-$C_3$ haloalkyl; and
R⁵ is H, F—, Cl—, Br— or methyl.

3. The compound of claim 1 or a pharmaceutically acceptable salt thereof, wherein
R¹ is cyclopropyl substituted with one or more selected from the group consisting of fluoro, $C_1$-$C_3$ alkyl, $C_1$-$C_3$ hydroxyalkyl and $C_1$-$C_3$ fluoroalkyl;
R² and R³ are independently —H, —F, —Br, —Cl, $C_1$-$C_3$ alkyl, or —CF₃;
R⁴ is phenyl, pyridinyl, pyrimidinyl, pyridazinyl, or pyrazinyl, wherein R⁴ is optionally substituted with one or more groups selected from the group consisting of halo, hydroxyl, $C_1$-$C_3$ alkyl, $C_1$-$C_3$ haloalkyl, mono($C_1$-$C_3$)alkylamino, di($C_1$-$C_3$)alkylamino, —NR$_a$R$_b$, —OR$_a$, —CN, —C(=O)R$_a$, —C(=O)OR$_a$, —OC(=O)R$_a$, —OC(=O)OR$_a$, —SR$_a$, furanyl, pyrazolyl, imidazolyl, isothiazolyl, thiazolyl, pyridinyl, pyridazinyl, pyrimidinyl, pyrazinyl and pyrrolyl; and
R$_a$ and R$_b$ are independently —H, halo, amino, $C_1$-$C_3$ alkyl, or $C_1$-$C_3$ haloalkyl.

4. The compound of claim 1 or a pharmaceutically acceptable salt thereof, wherein R¹ is cyclopropyl substituted with one or more groups selected from the group consisting of fluoro, methyl, ethyl, hydroxymethyl, hydroxyethyl, and methylaminomethyl.

5. The compound of claim 1 or a pharmaceutically acceptable salt thereof, wherein R¹ is fluorocyclopropyl, hydroxycyclopropyl, hydroxymethylcyclopropyl, difluorocyclopropyl, or methylaminomethylcyclopropyl, and R² and R³ are independently —H, methyl, or fluoro.

6. The compound of claim 1 or a pharmaceutically acceptable salt thereof, wherein R⁴ is fluoro-methylphenyl, fluoro-hydroxymethylphenyl, chloro-methylphenyl, dimethylphenyl, acetamido-methylphenyl, hydroxy-methylphenyl, hydroxypropanyl-methylphenyl, methyl-propenylphenyl, methyl-pyridinylethynylphenyl, methyl-pyrrolylphenyl, methyl-thiazolylphenyl, imidazolyl-methylphenyl, cyano-methylphenyl, methyl-pyrazolylphenyl, ethynyl-methylphenyl, methylpyridinyl, fluoro-methyl-methylaminophenyl, dimethylpyridinyl, fluoro-methylpyridinyl, fluoromethyl-methylpyridinyl, cyanopyridinyl, trifluoromethyl-methylpyridinyl, hydroxymethylpyridinyl, hydroxymethyl-methylpyridinyl, hydroxyethyl-methylpyridinyl, chloromethylpyridinyl, aminopyridinyl, acetyl-methylpyridinyl, amino-dimethylpyridinyl, hydroxyethyl-methylpyridinyl, methylindolyl, methylpyrimidinyl, dimethylisothiazolyl, trifluoromethylpyrimidinyl.

7. The compound of claim 1 or a pharmaceutically acceptable salt thereof, wherein R⁴ is fluoro-methylphenyl, fluoro-hydroxymethylphenyl, chloro-methylphenyl, dimethylphenyl, acetamido-methylphenyl, hydroxyl-methylphenyl, methyl-propenylphenyl, ethynyl-methylphenyl, fluoromethyl-methylaminophenyl, fluoro-hydroxyl-methylphenyl, methyl-methylaminophenyl, methyl-pyrrolylphenyl, methyl-thiazolylphenyl, cyano-methylphenyl, imidazolyl-methylphenyl, methylpyridinyl, chloro-methylpyridinyl, fluoro-methylpyridinyl, fluoromethyl-methylpyridinyl, bimethylpyridinyl, aminopyridinyl, amino-dimethylpyridinyl, methoxypyridinyl, acetyl-methylpyridinyl, hydroxymethylpyridinyl, hydroxymethyl-methylpyridinyl, hydroxyethyl-methylpyridinyl, cyanopyridinyl, trifluoromethylpyridinyl, methylpyrimidinyl, or dimethylpyrimidinyl.

8. The compound of claim 1 or a pharmaceutically acceptable salt thereof, wherein R⁴ is selected from the group consisting of phenyl, pyridinyl, and pyrimidinyl, wherein R⁴ is optionally substituted with one or more groups selected from the group consisting of halo, alkyl, alkynyl, hydroxyalkyl, amino, cyano, acetyl, hydroxy, and haloalkyl.

9. The compound of claim 1 or a pharmaceutically acceptable salt thereof, wherein R⁴ is selected from the group consisting of:

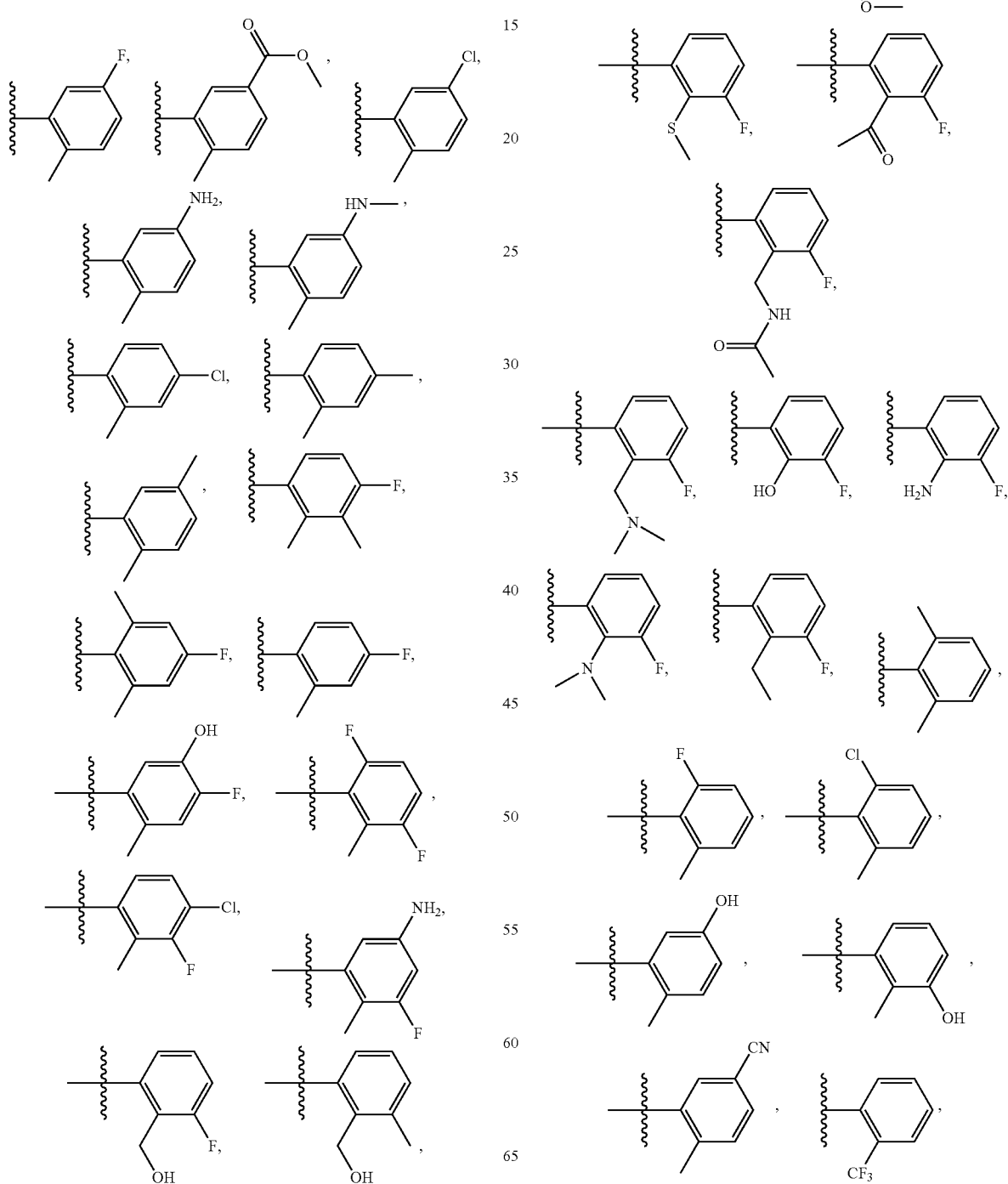

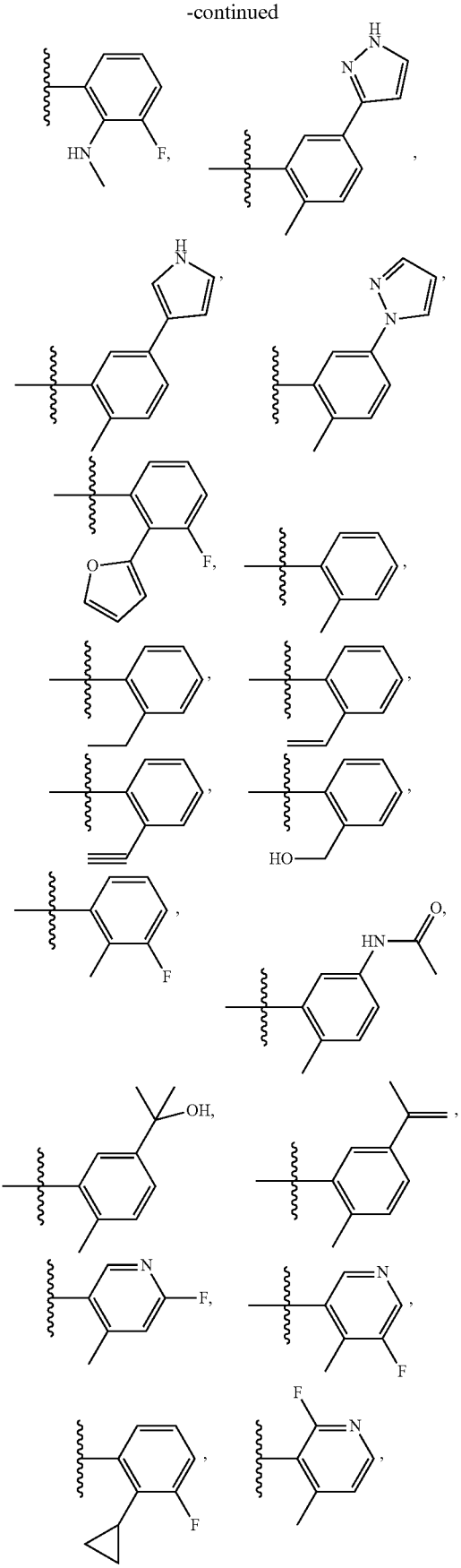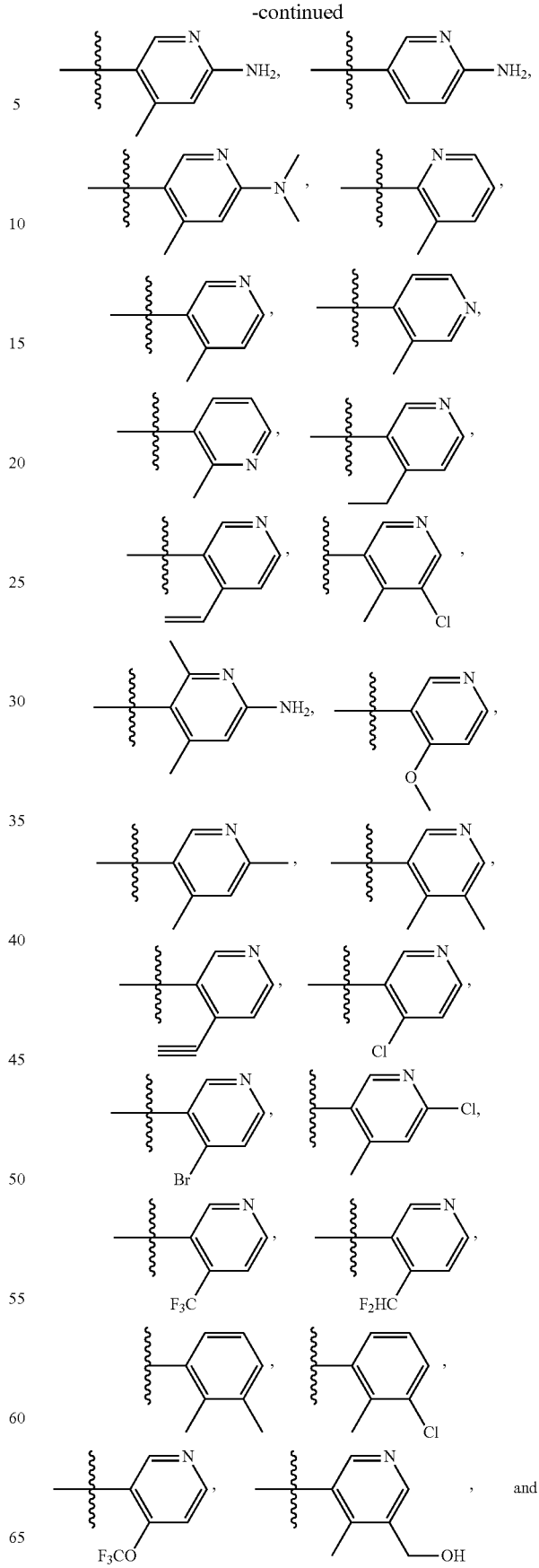

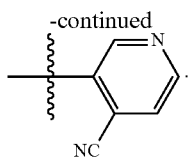

10. The compound of claim 1 or a pharmaceutically acceptable salt thereof, wherein $R^1$ is fluorocyclopropyl.

11. The compound of claim 10 or a pharmaceutically acceptable salt thereof, wherein $R^2$ and $R^3$ are —H; $R^4$ is phenyl, pyridinyl, wherein $R^4$ is optionally substituted with one or more groups selected from the group consisting of halo, hydroxyl, alkyl, haloalkyl, hydroxyalkyl, cycloalkyl, alkoxyalkyl, alkoxyalkoxy, alkylaminoalkyl, —$NR_aR_b$, —$NR_aC(=O)R_b$, —$OR_a$, —$SR_a$, —CN, —$C(=O)R_a$, —$C(=O)OR_a$, —$C(=O)NR_aR_b$, —$OC(=O)R_a$, furanyl, or pyrrolyl; $R_a$ and $R_b$ are independently —H, halo, amino, alkyl, or haloalkyl; and $R^5$ is —H, halo, or methyl.

12. The compound of claim 1 or a pharmaceutically acceptable salt thereof, which is a compound of Formula (II):

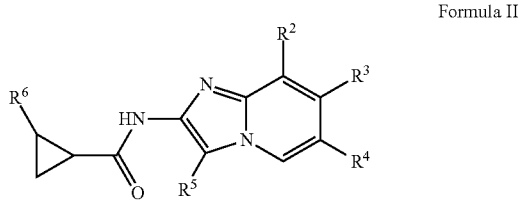

Formula II wherein $R^6$ is selected from the group consisting of halo, $C_1$-$C_3$ alkyl, $C_1$-$C_3$ hydroxyalkyl and $C_1$-$C_3$ haloalkyl.

13. The compound of claim 12 or a pharmaceutically acceptable salt thereof, wherein $R^2$ and $R^3$ are —H; $R^4$ is phenyl, or pyridinyl, wherein $R^4$ is optionally ubstituted with one or more groups selected from the group consisting of halo, hydroxyl, alkyl, haloalkyl, hydroxyalkyl, cycloalkyl, alkoxyalkyl, alkoxyalkoxy, alkylaminoalkyl, —$NR_aR_b$, —$NR_aC(=O)R_b$, —$OR_a$, —$SR_a$, —CN, —$C(=O)R_a$, —$C(=O)OR_a$, —$C(=O)NR_aR_b$, —$OC(=O)R_a$, furanyl, or pyrrolyl; $R_a$ and $R_b$ are independently —H, halo, amino, alkyl, or haloalkyl; and $R^5$ is —H, halo, or alkyl.

14. The compound of claim 12 or a pharmaceutically acceptable salt thereof, wherein the compound is selected from the group consisting of:
- 2-fluoro-N-(6-(3-fluoro-2-methylphenyl)imidazo[1,2-a]pyridin-2-yl)cyclopropane-1-carboxamide;
- 2-fluoro-N-(6-(2-fluoro-6-methylphenyl)imidazo[1,2-a]pyridin-2-yl)cyclopropane-1-carboxamide;
- N-(3-chloro-6-(3-fluoro-2-methylphenyl)imidazo[1,2-a]pyridin-2-yl)-2-fluorocyclopropane-1-carboxamide;
- N-(3-chloro-6-(2-fluoro-6-methylphenyl)imidazo[1,2-a]pyridin-2-yl)-2-fluorocyclopropane-1-carboxamide;
- 2-fluoro-N-(3-methyl-6-(4-methylpyridin-3-yl)imidazo[1,2-a]pyridin-2-yl)cyclopropane-1-carboxamide;
- 2-fluoro-N-(6-(4-methylpyridin-3-yl)imidazo[1,2-a]pyridin-2-yl)cyclopropane-1-carboxamide;
- N-(3-chloro-6-(4-methylpyridin-3-yl)imidazo[1,2-a]pyridin-2-yl)-2-fluorocyclopropane-1-carboxamide;
- 2-fluoro-N-(6-(3-fluoro-2-methylphenyl)-3-methylimidazo[1,2-a]pyridin-2-yl)cyclopropane-1-carboxamide;
- 2-fluoro-N-(6-(2-fluoro-6-methylphenyl)-3-methylimidazo[1,2-a]pyridin-2-yl)cyclopropane-1-carboxamide;
- 2-fluoro-N-(6-(5-fluoro-4-methylpyridin-3-yl)-3-methylimidazo[1,2-a]pyridin-2-yl)cyclopropane-1-carboxamide;
- 2-fluoro-N-(6-(5-fluoro-2-methylphenyl)imidazo[1,2-a]pyridin-2-yl)cyclopropane-1-carboxamide;
- 2-fluoro-N-(6-(5-hydroxy-2-methylphenyl)imidazo[1,2-a]pyridin-2-yl)cyclopropane-1-carboxamide;
- methyl 3-(2-(2-fluorocyclopropane-1-carboxamido)imidazo[1,2-a]pyridin-6-yl)-4-methylbenzoate;
- 2-fluoro-N-(6-(5-fluoro-4-methylpyridin-3-yl)imidazo[1,2-a]pyridin-2-yl)cyclopropane-1-carboxamide;
- N-(3-chloro-6-(5-fluoro-4-methylpyridin-3-yl)imidazo[1,2-a]pyridin-2-yl)-2-fluorocyclopropane-1-carboxamide;
- N-(6-(5-cyano-2-methylphenyl)imidazo[1,2-a]pyridin-2-yl)-2-fluorocyclopropane-1-carboxamide;
- 2-fluoro-N-(6-(3-hydroyx-2-methylphenyl)imidazo[1,2-a]pyridin-2-yl)cyclopropane-1-carboxamide;
- N-(6-(4-chloropyridin-3-yl)imidazo[1,2-a]pyridin-2-yl)-2-fluorocyclopropane-1-carboxamide;
- N-(6-(2,3-dimethylphenyl)imidazo[1,2-a]pyridin-2-yl)-2-fluorocyclopropane-1-carboxamide;
- N-(6-(5-amino-2-methylphenyl)imidazo[1,2-a]pyridin-2-yl)-2-fluorocyclopropane-1-carboxamide;
- 2-fluoro-N-(6-(2-methyl-5-(methylamino)phenyl)imidazo[1,2-a]pyridin-2-yl)cyclopropane-1-carboxamide;
- N-(6-(5-acetamido-2-methylphenyl)imidazo[1,2-a]pyridin-2-yl)-2-fluorocyclopropane-1-carboxamide;
- N-(6-(5-chloro-2-methylphenyl)imidazo[1,2-a]pyridin-2-yl)-2-fluorocyclopropane-1-carboxamide;
- N-(6-(4-chloro-2-methylphenyl)imidazo[1,2-a]pyridin-2-yl)-2-fluorocyclopropane-1-carboxamide;
- N-(6-(3-chloro-2-methylphenyl)imidazo[1,2-a]pyridin-2-yl)-2-fluorocyclopropane-1-carboxamide;
- 2-fluoro-N-(6-(4-(trifluoromethyl)pyridin-3-yl)imidazo[1,2-a]pyridin-2-yl)cyclopropane-1-carboxamide;
- N-(6-(2,4-dimethylphenyl)imidazo[1,2-a]pyridin-2-yl)-2-fluorocyclopropane-1-carboxamide;
- 2-fluoro-N-(3-fluoro-6-(3-fluoro-2-methylphenyl)imidazo[1,2-a]pyridin-2-yl)cyclopropane-1-carboxamide;
- N-(6-(2,5-dimethylphenyl)imidazo[1,2-a]pyridin-2-yl)-2-fluorocyclopropane-1-carboxamide;
- N-(6-(4-cyanopyridin-3-yl)imidazo[1,2-a]pyridin-2-yl)-2-fluorocyclopropane-1-carboxamide;
- 2-fluoro-N-(6-(4-fluoro-2,3-dimethylphenyl)imidazo[1,2-a]pyridin-2-yl)cyclopropane-1-carboxamide;
- 2-fluoro-N-(6-(4-fluoro-2,6-dimethylphenyl)imidazo[1,2-a]pyridin-2-yl)cyclopropane-1-carboxamide;
- 2-fluoro-N-(6-(4-fluoro-2-methylphenyl)imidazo[1,2-a]pyridin-2-yl)cyclopropane-1-carboxamide;
- 2-fluoro-N-(6-(2-methyl-5-(1H-pyrrol-3-yl)phenyl)imidazo[1,2-a]pyridin-2-yl)cyclopropane-1-carboxamide;
- N-(6-(2,6-dimethylphenyl)imidazo[1,2-a]pyridin-2-yl)-2-fluorocyclopropane-1-carboxamide;
- 2-fluoro-N-(6-(4-fluoro-5-hydroxy-2-methylphenyl)imidazo[1,2-a]pyridin-2-yl)cyclopropane-1-carboxamide;
- N-(6-(3,4-difluoro-2-methylphenyl)imidazo[1,2-a]pyridin-2-yl)-2-fluorocyclopropane-1-carboxamide;
- N-(6-(3,6-difluoro-2-methylphenyl)imidazo[1,2-a]pyridin-2-yl)-2-fluorocyclopropane-1-carboxamide;
- N-(6-(4-chloro-3-fluoro-2-methylphenyl)imidazo[1,2-a]pyridin-2-yl)-2-fluorocyclopropane-1-carboxamide;
- 2-fluoro-N-(6-(2-fluoro-4-methylpyridin-3-yl)imidazo[1,2-a]pyridin-2-yl)cyclopropane-1-carboxamide;
- 2-fluoro-N-(6-(4-methoxypyridin-3-yl)imidazo[1,2-a]pyridin-2-yl)cyclopropane-1-carboxamide;

N-(6-(6-amino-4-methylpyridin-3-yl)imidazo[1,2-a]pyridin-2-yl)-2-fluorocyclopropane-1-carboxamide;
N-(6-(5-amino-3-fluoro-2-methylphenyl)imidazo[1,2-a]pyridin-2-yl)-2-fluorocyclopropane-1-carboxamide;
N-(6-(2-chloro-6-methylphenyl)imidazo[1,2-a]pyridin-2-yl)-2-fluorocyclopropane-1-carboxamide;
N-(6-(6-aminopyridin-3-yl)imidazo[1,2-a]pyridin-2-yl)-2-fluorocyclopropane-1-carboxamide;
2-fluoro-N-(6-(2-methyl-5-(1H-pyrazol-1-yl)phenyl)imidazo[1,2-a]pyridin-2-yl)cyclopropane-1-carboxamide;
2-fluoro-N-(6-(3-fluoro-2-(hydroxymethyl)phenyl)imidazo[1,2-a]pyridin-2-yl)cyclopropane-1-carboxamide;
N-(3-bromo-6-(3-fluoro-2-methylphenyl)imidazo[1,2-a]pyridin-2-yl)-2-fluorocyclopropane-1-carboxamide;
2-fluoro-N-(6-(3-fluoro-2-methoxyphenyl)imidazo[1,2-a]pyridin-2-yl)cyclopropanecarboxamide;
N-(6-(2-cyano-3-fluorophenyl)imidazo[1,2-a]pyridin-2-yl)-2-fluorocyclopropanecarboxamide;
N-(6-(2-chloro-3-fluorophenyl)imidazo[1,2-a]pyridin-2-yl)-2-fluorocyclopropanecarboxamide;
N-(6-(2,3-difluorophenyl)imidazo[1,2-a]pyridin-2-yl)-2-fluorocyclopropanecarboxamide;
N-(6-(3,5-dimethyl-1H-indol-4-yl)imidazo[1,2-a]pyridin-2-yl)-2-fluorocyclopropanecarboxamide;
2-fluoro-N-(6-(3-fluoro-2-(methoxymethyl)phenyl)imidazo[1,2-a]pyridin-2-yl)cyclopropanecarboxamide;
2-fluoro-N-(6-(3-fluoro-2-(furan-2-yl)phenyl)imidazo[1,2-a]pyridin-2-yl)cyclopropanecarboxamide;
2-fluoro-N-(6-(3-fluoro-2-(methylthio)phenyl)imidazo[1,2-a]pyridin-2-yl)cyclopropanecarboxamide;
2-fluoro-N-(6-(6-fluoro-4-methylpyridin-3-yl)imidazo[1,2-a]pyridin-2-yl)cyclopropanecarboxamide;
N-(6-(2-acetyl-3-fluorophenyl)imidazo[1,2-a]pyridin-2-yl)-2-fluorocyclopropanecarboxamide;
N-(6-(6-(dimethylamino)-4-methylpyridin-3-yl)imidazo[1,2-a]pyridin-2-yl)-2-fluorocyclopropanecarboxamide;
2-fluoro-N-(6-(3-fluoro-2-methylphenyl)imidazo[1,2-a]pyridin-2-yl)cyclopropanecarboxamide;
2-fluoro-N-(6-(3-fluoro-2-methylphenyl)imidazo[1,2-a]pyridin-2-yl)cyclopropanecarboxamide;
2-fluoro-N-(6-(3-fluoro-2-methylphenyl)imidazo[1,2-a]pyridin-2-yl)cyclopropanecarboxamide;
N-(6-(2-(aminomethyl)-3-fluorophenyl)imidazo[1,2-a]pyridin-2-yl)-2-fluorocyclopropanecarboxamide;
N-(6-(2-(acetamidomethyl)-3-fluorophenyl)imidazo[1,2-a]pyridin-2-yl)-2-fluorocyclopropanecarboxamide;
2,2-difluoro-N-(6-(3-fluoro-2-methylphenyl)imidazo[1,2-a]pyridin-2-yl)cyclopropanecarboxamide;
2-fluoro-N-(6-(3-fluoro-2-((methylamino)methyl)phenyl)imidazo[1,2-a]pyridin-2-yl) cyclopropanecarboxamide;
2-fluoro-N-(6-(3-fluoro-2-((isopropylamino)methyl)phenyl)imidazo[1,2-a]pyridin-2-yl)cyclopropanecarboxamide;
2-fluoro-N-(6-(3-fluoro-2-((2-methoxyethoxy)methyl)phenyl)imidazo[1,2-a]pyridin-2-yl)cyclopropanecarboxamide;
2-fluoro-N-(6-(3-fluoro-2-((2-hydroxyethoxy)methyl)phenyl)imidazo[1,2-a]pyridin-2-yl)cyclopropanecarboxamide;
N-(6-(2-((dimethylamino)methyl)-3-fluorophenyl)imidazo[1,2-a]pyridin-2-yl)-2-fluorocyclopropanecarboxamide;
2-fluoro-N-(6-(o-tolyl)imidazo[1,2-a]pyridin-2-yl)cyclopropanecarboxamide;
2-fluoro-N-(6-(3-fluoro-2-hydroxyphenyl)imidazo[1,2-a]pyridin-2-yl)cyclopropanecarboxamide;
N-(6-(2-amino-3-fluorophenyl)imidazo[1,2-a]pyridin-2-yl)-2-fluorocyclopropanecarboxamide;
N-(6-(2-(dimethylamino)-3-fluorophenyl)imidazo[1,2-a]pyridin-2-yl)-2-fluorocyclopropanecarboxamide;
N-(6-(2-ethyl-3-fluorophenyl)imidazo[1,2-a]pyridin-2-yl)-2-fluorocyclopropanecarboxamide;
2-fluoro-N-(6-(3-fluoro-2-(trifluoromethyl)phenyl)imidazo[1,2-a]pyridin-2-yl)cyclopropanecarboxamide;
N-(6-(2-cyclopropyl-3-fluorophenyl)imidazo[1,2-a]pyridin-2-yl)-2-fluorocyclopropanecarboxamide;
2-fluoro-N-(6-(3-fluoro-2-(methylamino)phenyl)imidazo[1,2-a]pyridin-2-yl)cyclopropanecarboxamide;
2-fluoro-N-(6-(3-fluoro-2-isopropylphenyl)imidazo[1,2-a]pyridin-2-yl)cyclopropanecarboxamide;
2-fluoro-N-(6-(3-fluoro-2-(trifluoromethyl)phenyl)imidazo[1,2-a]pyridin-2-yl)cyclopropane-1-carboxamide;
2-fluoro-N-(6-(3-fluoro-2,6-dimethylphenyl)imidazo[1,2-a]pyridin-2-yl)cyclopropane-1-carboxamide;
N-(6-(2-ethyl-6-methylphenyl)imidazo[1,2-a]pyridin-2-yl)-2-fluorocyclopropane-1-carboxamide
N-(6-(4-acetyl-2-methylphenyl)imidazo[1,2-a]pyridin-2-yl)-2-fluorocyclopropane-1-carboxamide;
N-(6-(2-chloro-3,4-difluorophenyl)imidazo[1,2-a]pyridin-2-yl)-2-fluorocyclopropane-1-carboxamide;
N-(6-(2-chloro-3,6-difluorophenyl)imidazo[1,2-a]pyridin-2-yl)-2-fluorocyclopropane-1-carboxamide;
2-fluoro-N-(6-(3-fluoro-2-methylphenyl)-8-(trifluoromethyl)imidazo[1,2-a]pyridin-2-yl)cyclopropane-1-carboxamide;
N-(8-(difluoromethyl)-6-(3-fluoro-2-methylphenyl)imidazo[1,2-a]pyridin-2-yl)-2-fluorocyclopropane-1-carboxamide;
2-fluoro-N-(6-(3-fluoro-2-methylphenyl)-8-(fluoromethyl)imidazo[1,2-a]pyridin-2-yl)cyclopropane-1-carboxamide;
2-fluoro-N-(8-fluoro-6-(3-fluoro-2-methylphenyl)imidazo[1,2-a]pyridin-2-yl)cyclopropane-1-carboxamide;
2-fluoro-N-(7-fluoro-6-(3-fluoro-2-methylphenyl)imidazo[1,2-a]pyridin-2-yl)cyclopropane-1-carboxamide;
2-fluoro-N-(6-(4-fluoro-2-methylphenyl)-8-(trifluoromethyl)imidazo[1,2-a]pyridin-2-yl)cyclopropane-1-carboxamide;
N-(8-(difluoromethyl)-6-(4-fluoro-2-methylphenyl)imidazo[1,2-a]pyridin-2-yl)-2-fluorocyclopropane-1-carboxamide;
2-fluoro-N-(6-(4-fluoro-2-methylphenyl)-8-(fluoromethyl)imidazo[1,2-a]pyridin-2-yl)cyclopropane-1-carboxamide;
2-fluoro-N-(8-fluoro-6-(4-fluoro-2-methylphenyl)imidazo[1,2-a]pyridin-2-yl)cyclopropane-1-carboxamide;
2-fluoro-N-(7-fluoro-6-(4-fluoro-2-methylphenyl)imidazo[1,2-a]pyridin-2-yl)cyclopropane-1-carboxamide;
2-fluoro-N-(6-(5-fluoro-2-methylphenyl)-8-(trifluoromethyl)imidazo[1,2-a]pyridin-2-yl)cyclopropane-1-carboxamide;
N-(8-(difluoromethyl)-6-(5-fluoro-2-methylphenyl)imidazo[1,2-a]pyridin-2-yl)-2-fluorocyclopropane-1-carboxamide;
2-fluoro-N-(6-(5-fluoro-2-methylphenyl)-8-(fluoromethyl)imidazo[1,2-a]pyridin-2-yl)cyclopropane-1-carboxamide;
2-fluoro-N-(8-fluoro-6-(5-fluoro-2-methylphenyl)imidazo[1,2-a]pyridin-2-yl)cyclopropane-1-carboxamide;
2-fluoro-N-(7-fluoro-6-(5-fluoro-2-methylphenyl)imidazo[1,2-a]pyridin-2-yl)cyclopropane-1-carboxamide;

2-fluoro-N-(6-(2-fluoro-6-methylphenyl)-8-(trifluoromethyl)imidazo[1,2-a]pyridin-2-yl)cyclopropane-1-carboxamide;

N-(8-(difluoromethyl)-6-(2-fluoro-6-methylphenyl)imidazo[1,2-a]pyridin-2-yl)-2-fluorocyclopropane-1-carboxamide;

2-fluoro-N-(6-(2-fluoro-6-methylphenyl)-8-(fluoromethyl)imidazo[1,2-a]pyridin-2-yl)cyclopropane-1-carboxamide;

2-fluoro-N-(8-fluoro-6-(2-fluoro-6-methylphenyl)imidazo[1,2-a]pyridin-2-yl)cyclopropane-1-carboxamide; and 2-fluoro-N-(7-fluoro-6-(2-fluoro-6-methylphenyl)imidazo[1,2-a]pyridin-2-yl)cyclopropane-1-carboxamide.

15. The compound of claim 12 or a pharmaceutically acceptable salt thereof, wherein the compound is selected from the group consisting of:

2-fluoro-N-(6-(3-fluoro-2-methylphenyl)imidazo[1,2-a]pyridin-2-yl)cyclopropane-1-carboxamide;

2-fluoro-N-(6-(2-fluoro-6-methylphenyl)imidazo[1,2-a]pyridin-2-yl)cyclopropane-1-carboxamide;

N-(3-chloro-6-(3-fluoro-2-methylphenyl)imidazo[1,2-a]pyridin-2-yl)-2-fluorocyclopropane-1-carboxamide;

N-(3-chloro-6-(2-fluoro-6-methylphenyl)imidazo[1,2-a]pyridin-2-yl)-2-fluorocyclopropane-1-carboxamide;

2-fluoro-N-(6-(3-fluoro-2-methylphenyl)-3-methylimidazo[1,2-a]pyridin-2-yl)cyclopropane-1-carboxamide;

2-fluoro-N-(6-(2-fluoro-6-methylphenyl)-3-methylimidazo[1,2-a]pyridin-2-yl)cyclopropane-1-carboxamide;

2-fluoro-N-(6-(5-fluoro-2-methylphenyl)imidazo[1,2-a]pyridin-2-yl)cyclopropane-1-carboxamide;

2-fluoro-N-(6-(5-hydroxy-2-methylphenyl)imidazo[1,2-a]pyridin-2-yl)cyclopropane-1-carboxamide;

2-fluoro-N-(6-(3-hydroxy-2-methylphenyl)imidazo[1,2-a]pyridin-2-yl)cyclopropane-1-carboxamide;

N-(6-(2,3-dimethylphenyl)imidazo[1,2-a]pyridin-2-yl)-2-fluorocyclopropane-1-carboxamide;

2-fluoro-N-(6-(2-methyl-5-(methylamino)phenyl)imidazo[1,2-a]pyridin-2-yl)cyclopropane-1-carboxamide;

N-(6-(2,4-dimethylphenyl)imidazo[1,2-a]pyridin-2-yl)-2-fluorocyclopropane-1-carboxamide;

2-fluoro-N-(3-fluoro-6-(3-fluoro-2-methylphenyl)imidazo[1,2-a]pyridin-2-yl)cyclopropane-1-carboxamide;

N-(6-(2,5-dimethylphenyl)imidazo[1,2-a]pyridin-2-yl)-2-fluorocyclopropane-1-carboxamide;

2-fluoro-N-(6-(2-methyl-5-(1H-pyrrol-3-yl)phenyl)imidazo[1,2-a]pyridin-2-yl)cyclopropane-1-carboxamide;

N-(6-(2,6-dimethylphenyl)imidazo[1,2-a]pyridin-2-yl)-2-fluorocyclopropane-1-carboxamide;

2-fluoro-N-(6-(4-fluoro-5-hydroxy-2-methylphenyl)imidazo[1,2-a]pyridin-2-yl)cyclopropane-1-carboxamide;

N-(3-bromo-6-(3-fluoro-2-methylphenyl)imidazo[1,2-a]pyridin-2-yl)-2-fluorocyclopropane-1-carboxamide;

2-fluoro-N-(6-(3-fluoro-2-methylphenyl)imidazo[1,2-a]pyridin-2-yl)cyclopropanecarboxamide;

2-fluoro-N-(6-(3-fluoro-2-methylphenyl)imidazo[1,2-a]pyridin-2-yl)cyclopropanecarboxamide; and 2-fluoro-N-(6-(3-fluoro-2-methylphenyl)imidazo[1,2-a]pyridin-2-yl)cyclopropanecarboxamide.

16. The compound of claim 1 or a pharmaceutically acceptable salt thereof, which is a compound of Formula (III):

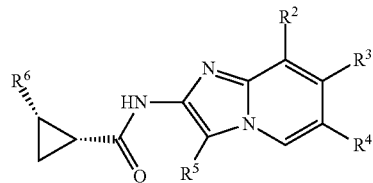

Formula III wherein $R^6$ is selected from the group consisting of halo, $C_1$-$C_3$ alkyl, $C_1$-$C_3$ hydroxyalkyl and $C_1$-$C_3$ haloalkyl.

17. The compound of claim 16 or a pharmaceutically acceptable salt thereof, wherein $R^2$ and $R^3$ are —H; $R^4$ is phenyl, or pyridinyl, wherein $R^4$ is optionally substituted with one or more groups selected from the group consisting of halo, hydroxyl, alkyl, haloalkyl, hydroxyalkyl, cycloalkyl, alkoxyalkyl, alkoxyalkoxy, alkylaminoalkyl, —$NR_aR_b$, —$NR_aC(=O)R_b$, —$OR_a$, —$SR_a$, —CN, —C(=O)$R_a$, —C(=O)O$R_a$, —C(=O)N$R_aR_b$, —OC(=O)$R_a$, furanyl, or pyrrolyl; $R_a$ and $R_b$ are independently —H, halo, amino, alkyl, or haloalkyl; and $R^5$ is —H, halo, or alkyl.

18. The compound of claim 16 or a pharmaceutically acceptable salt thereof, which is selected from the group consisting of:

(1S,2S)-2-fluoro-N-(6-(3-fluoro-2-methylphenyl)imidazo[1,2-a]pyridin-2-yl)cyclopropane-1-carboxamide;

(1S,2S)-2-fluoro-N-(6-(2-fluoro-6-methylphenyl)imidazo[1,2-a]pyridin-2-yl)cyclopropane-1-carboxamide;

(1S,2S)-N-(3-chloro-6-(3-fluoro-2-methylphenyl)imidazo[1,2-a]pyridin-2-yl)-2-fluorocyclopropane-1-carboxamide;

(1S,2S)-N-(3-chloro-6-(2-fluoro-6-methylphenyl)imidazo[1,2-a]pyridin-2-yl)-2-fluorocyclopropane-1-carboxamide;

(1S,2S)-2-fluoro-N-(3-methyl-6-(4-methylpyridin-3-yl)imidazo[1,2-a]pyridin-2-yl)cyclopropane-1-carboxamide;

(1S,2S)-2-fluoro-N-(6-(4-methylpyridin-3-yl)imidazo[1,2-a]pyridin-2-yl)cyclopropane-1-carboxamide;

(1S,2S)-N-(3-chloro-6-(4-methylpyridin-3-yl)imidazo[1,2-a]pyridin-2-yl)-2-fluorocyclopropane-1-carboxamide;

(1S,2S)-2-fluoro-N-(6-(3-fluoro-2-methylphenyl)-3-methylimidazo[1,2-a]pyridin-2-yl)cyclopropane-1-carboxamide;

(1S,2S)-2-fluoro-N-(6-(2-fluoro-6-methylphenyl)-3-methylimidazo[1,2-a]pyridin-2-yl)cyclopropane-1-carboxamide;

(1S,2S)-2-fluoro-N-(6-(5-fluoro-4-methylpyridin-3-yl)-3-methylimidazo[1,2-a]pyridin-2-yl)cyclopropane-1-carboxamide;

(1S,2S)-2-fluoro-N-(6-(5-fluoro-2-methylphenyl)imidazo[1,2-a]pyridin-2-yl)cyclopropane-1-carboxamide;

(1S,2S)-2-fluoro-N-(6-(5-hydroxy-2-methylphenyl)imidazo[1,2-a]pyridin-2-yl(cyclopropane-1-carboxamide;

methyl 3-(2-((1S,2S)-2-fluorocyclopropane-1-carboxamido)imidazo[1,2-a]pyridin-6-yl)-4-methylbenzoate;

(1S,2S)-2-fluoro-N-(6-(5-fluoro-4-methylpyridin-3-yl)imidazo[1,2-a]pyridin-2-yl)cyclopropane-1-carboxamide;

(1S,2S)-N-(3-chloro-6-(5-fluoro-4-methylpyridin-3-yl)imidazo[1,2-a]pyridin-2-yl)-2-fluorocyclopropane-1-carboxamide;

(1S,2S)-N-(6-(5-cyano-2-methylphenyl)imidazo[1,2-a]pyridin-2-yl)-2-fluorocyclopropane-1-carboxamide;
(1S,2S)-2-fluoro-N-(6-(3-hydroxy-2-methylphenyl)imidazo[1,2-a]pyridin-2-yl)cyclopropane-1-carboxamide;
(1S,2S)-N-(6-(4-chloropyridin-3-yl)imidazo[1,2-a]pyridin-2-yl)-2-fluorocyclopropane-1-carboxamide;
(1S,2S)-N-(6-(2,3-dimethylphenyl)imidazo[1,2-a]pyridin-2-yl)-2-fluorocyclopropane-1-carboxamide;
(1S,2S)-N-(6-(5-amino-2-methylphenyl)imidazo[1,2-a]pyridin-2-yl)-2-fluorocyclopropane-1-carboxamide;
(1S,2S)-2-fluoro-N-(6-(2-methyl-5-(methylamino)phenyl)imidazo[1,2-a]pyridin-2-yl)cyclopropane-1-carboxamide;
(1S,2S)-N-(6-(5-acetamido-2-methylphenyl)imidazo[1,2-a]pyridin-2-yl)-2-fluorocyclopropane-1-carboxamide;
(1S,2S)-N-(6-(5-chloro-2-methylphenyl)imidazo[1,2-a]pyridin-2-yl)-2-fluorocyclopropane-1-carboxamide;
(1S,2S)-2-fluoro-N-(6-(2-methyl-5-(1H-pyrazol-3-yl)phenyl)imidazo[1,2-a]pyridin-2-yl)cyclopropane-1-carboxamide;
(1S,2S)-N-(6-(4-chloro-2-methylphenyl)imidazo[1,2-a]pyridin-2-yl)-2-fluorocyclopropane-1-carboxamide;
(1S,2S)-N-(6-(3-chloro-2-methylphenyl)imidazo[1,2-a]pyridin-2-yl)-2-fluorocyclopropane-1-carboxamide;
(1S,2S)-2-fluoro-N-(6-(4-(trifluoromethyl)pyridin-3-yl)imidazo[1,2-a]pyridin-2-yl)cyclopropane-1-carboxamide;
(1S,2S)-N-(6-(2,4-dimethylphenyl)imidazo[1,2-a]pyridin-2-yl)-2-fluorocyclopropane-1carboxamide;
(1S,2S)-2-fluoro-N-(3-fluoro-6-(3-fluoro-2-methylphenyl)imidazo[1,2-a]pyridin-2-yl)cyclopropane-1-carboxamide;
(1S,2S)-N-(6-(2,5-dimethylphenyl)imidazo[1,2-a]pyridin-2-yl)-2-fluorocyclopropane-1-carboxamide;
(1S,2S)-N-(6-(4-cyanopyridin-3-yl)imidazo[1,2-a]pyridin-2-yl)-2-fluorocyclopropane-1-carboxamide;
(1S,2S)-2-fluoro-N-(6-(4-fluoro-2,3-dimethylphenyl)imidazo[1,2-a]pyridin-2-yl)cyclopropane-1-carboxamide;
(1S,2S)-2-fluoro-N-(6-(4-fluoro-2,6-dimethylphenyl)imidazo[1,2-a]pyridin-2-yl)cyclopropane-1-carboxamide;
(1S,2S)-2-fluoro-N-(6-(4-fluoro-2-methylphenyl)imidazo[1,2-a]pyridin-2-yl)cyclopropane-1-carboxamide;
(1S,2S)-2-fluoro-N-(6-(2-methyl-5-(1H-pyrrol-3-yl)phenyl)imidazo[1,2-a]pyridin-2-yl)cyclopropane-1-carboxamide;
(1S,2S)-2-fluoro-N-(6-(3-methylthiophen-2-yl)imidazo[1,2-a]pyridin-2-yl)cyclopropane-1-carboxamide;
(1S,2S)-N-(6-(2,6-dimethylphenyl)imidazo[1,2-a]pyridin-2-yl)-2-fluorocyclopropane-1-carboxamide;
(1S,2S)-2-fluoro-N-(6-(4-fluoro-5-hydroxy-2-methylphenyl)imidazo[1,2-a]pyridin-2-yl)cyclopropane-1-carboxamide;
(1S,2S)-N-(6-(3,4-difluoro-2-methylphenyl)imidazo[1,2-a]pyridin-2-yl)-2-fluorocyclopropane-1-carboxamide;
(1S,2S)-N-(6-(3,6-difluoro-2-methylphenyl)imidazo[1,2-a]pyridin-2-yl)-2-fluorocyclopropane-1-carboxamide;
(1S,2S)-N-(6-(4-chloro-3-fluoro-2-methylphenyl)imidazo[1,2-a]pyridin-2-yl)-2-fluorocyclopropane-1-carboxamide;
(1S,2S)-2-fluoro-N-(6-(2-fluoro-4-methylpyridin-3-yl)imidazo[1,2-a]pyridin-2-yl)cyclopropane-1-carboxamide;
(1S,2S)-2-fluoro-N-(6-(4-methoxypyridin-3-yl)imidazo[1,2-a]pyridin-2-yl)cyclopropane-1-carboxamide;
(1S,2S)-N-(6-(6-amino-4-methylpyridin-3-yl)imidazo[1,2-a]pyridin-2-yl)-2-fluorocyclopropane-1-carboxamide;
(1S,2S)-N-(6-(5-amino-3-fluoro-2-methylphenyl)imidazo[1,2-a]pyridin-2-yl)-2-fluorocyclopropane-1-carboxamide;
(1S,2S)-N-(6-(2-chloro-6-methylphenyl)imidazo[1,2-a]pyridin-2-yl)-2-fluorocyclopropane-1-carboxamide;
(1S,2S)-N-(6-(6-aminopyridin-3-yl)imidazo[1,2-a]pyridin-2-yl)-2-fluorocyclopropane-1-carboxamide;
(1S,2S)-2-fluoro-N-(6-(2-methyl-5-(1H-pyrazol-1-yl)phenyl)imidazo[1,2-a]pyridin-2-yl)cyclopropane-1-carboxamide;
(1S,2S)-2-fluoro-N-(6-(3-fluoro-2-(hydroxymethyl)phenyl)imidazo[1,2-a]pyridin-2-yl)cyclopropane-1-carboxamide;
(1S,2S)-N-(3-bromo-6-(3-fluoro-2-methylphenyl)imidazo[1,2-a]pyridin-2-yl)-2-fluorocyclopropane-1-carboxamide;
(1S,2S)-2-fluoro-N-(6-(3-fluoro-2-methoxyphenyl)imidazo[1,2-a] pyridin-2-yl)cyclopropanecarboxamide;
(1S,2S)-N-(6-(2-cyano-3-fluorophenyl)imidazo[1,2-a]pyridin-2-yl)-2-fluorocyclopropanecarboxamide;
(1S,2S)-N-(6-(2-chloro-3-fluorophenyl)imidazo[1,2-a]pyridin-2-yl)-2-fluorocyclopropanecarboxamide;
(1S,2S)-N-(6-(2,3-difluorophenyl)imidazo[1,2-a]pyridin-2-yl)-2-fluorocyclopropanecarboxamide;
(1S,2S)-2-fluoro-N-(6-(3-fluoro-2-(methoxymethyl)phenyl)imidazo[1,2-a]pyridin-2-yl)cyclopropanecarboxamide;
(1S,2S)-2-fluoro-N-(6-(3-fluoro-2-(furan-2-yl)phenyl)imidazo[1,2-a]pyridin-2-yl)cyclopropanecarboxamide;
(1S,2S)-2-fluoro-N-(6-(3-fluoro-2-(methylthio)phenyl)imidazo[1,2-a]pyridin-2-yl)cyclopropanecarboxamide;
(1S,2S)-2-fluoro-N-(6-(6-fluoro-4-methylpyridin-3-yl)imidazo[1,2-a]pyridin-2-yl)cyclopropanecarboxamide;
(1S,2S)-N-(6-(2-acetyl-3-fluorophenyl)imidazo[1,2-a]pyridin-2-yl)-2-fluorocyclopropanecarboxamide;
(1S,2S)-N-(6-(6-(dimethylamino)-4-methylpyridin-3-yl)imidazo[1,2-a]pyridin-2-yl)-2-fluorocyclopropanecarboxamide;
(1S,2S)-N-(6-(2-(aminomethyl)-3-fluorophenyl)imidazo[1,2-a]pyridin-2-yl)-2-fluorocyclopropanecarboxamide;
(1S,2S)-N-(6-(2-(acetamidomethyl)-3-fluorophenyl)imidazo[1,2-a]pyridin-2-yl)-2-fluorocyclopropanecarboxamide;
(1S,2S)-2-fluoro-N-(6-(3-fluoro-2-((methylamino)methyl)phenyl)imidazo[1,2-a]pyridin-2-yl)cyclopropanecarboxamide;
(1S,2S)-2-fluoro-N-(6-(3-fluoro-2-((isopropylamino)methyl)phenyl)imidazo[1,2-a]pyridin-2-yl)cyclopropanecarboxamide;
(1S,2S)-2-fluoro-N-(6-(3-fluoro-2-((2-methoxyethoxy)methyl)phenyl)imidazo[1,2-a]pyridin-2-yl)cyclopropanecarboxamide;
(1S,2S)-2-fluoro-N-(6-(3-fluoro-2-((2-hydroxyethoxy)methyl)phenyl)imidazo[1,2-a]pyridin-2-yl)cyclopropanecarboxamide;
(1S,2S)-N-(6-(2-((dimethylamino)methyl)-3-fluorophenyl)imidazo[1,2-a]pyridin-2-yl)-2-fluorocyclopropanecarboxamide;
(1S,2S)-2-fluoro-N-(6-(o-tolyl)pimidazo[1,2-a]pyridin-2-yl)cyclopropanecarboxamide;
(1S,2S)-2-fluoro-N-(6-(3-fluoro-2-hydroxyphenyl)imidazo[1,2-a]pyridin-2-yl)cyclopropanecarboxamide;
(1S,2S)-N-(6-(2-amino-3-fluorophenyl)imidazo[1,2-a]pyridin-2-yl)-2-fluorocyclopropanecarboxamide;

(1S,2S)-N-(6-(2-(dimethylamino)-3-fluorophenyl)imidazo[1,2-a]pyridin-2-yl)-2-fluorocyclopropanecarboxamide;
(1S,2S)-N-(6-(2-ethyl-3-fluorophenyl)imidazo[1,2-a]pyridin-2-yl)-2-fluorocyclopropanecarboxamide;
(1S,2S)-2-fluoro-N-(6-(3-fluoro-2-(trifluoromethyl)phenyl)imidazo[1,2-a]pyridin-2-yl)cyclopropanecarboxamide;
(1S,2S)-N-(6-(2-cyclopropyl-3-fluorophenyl)imidazo[1,2-a]pyridin-2-yl)-2-fluorocyclopropanecarboxamide;
(1S,2S)-2-fluoro-N-(6-(3-fluoro-2-(methylamino)phenyl)imidazo[1,2-a]pyridin-2-yl)cyclopropanecarboxamide; and
(1S,2S)-2-fluoro-N-(6-(3-fluoro-2-isopropylphenyl)imidazo[1,2-a]pyridin-2-yl)cyclopropanecarboxamide.

19. The compound of claim 16 or a pharmaceutically acceptable salt thereof, which is selected from the group consisting of:
(1S,2S)-2-fluoro-N-(6-(3-fluoro-2-methylphenyl)imidazo[1,2-a]pyridin-2-yl)cyclopropane-1-carboxamide;
(1S,2S)-2-fluoro-N-(6-(5-fluoro-2-methylphenyl)imidazo[1,2-a]pyridin-2-yl)cyclopropane-1-carboxamide;
(1S,2S)-2-fluoro-N-(6-(5-hydroxy-2-methylphenyl)imidazo[1,2-a]pyridin-2-yl)cyclopropane-1-carboxamide;
(1S,2S)-N-(6-(4-chloropyridin-3-yl)imidazo[1,2-a]pyridin-2-yl)-2-fluorocyclopropane-1-carboxamide;
(1S,2S)-2-fluoro-N-(6-(2-methyl-5-(methylamino)phenyl)imidazo[1,2-a]pyridin-2-yl)cyclopropane-1-carboxamide;
(1S,2S)-2-fluoro-N-(6-(3-methylthiophen-2-yl)imidazo[1,2-a]pyridin-2-yl)cyclopropane-1-carboxamide; and
(1S,2S)-N-(6-(3,4-difluoro-2-methylphenyl)imidazo[1,2-a]pyridin-2-yl)-2-fluorocyclopropane-1-carboxamide.

20. The compound of claim 1, wherein the salt is hydrochloric acid salt, tartaric acid salt, phosphoric acid salt, or maleic acid salt.

21. A pharmaceutical composition comprising a therapeutically effective amount of the compound of claim 1 or a pharmaceutically acceptable salt thereof, and at least one pharmaceutically acceptable carrier.

22. The pharmaceutical composition of claim 21, further comprising one or more active ingredient that is useful to treat a neurodegenerative disease.

23. A compound selected from the group consisting of:
2-fluoro-N-(6-(5-methyl-1H-indol-4-yl)imidazo[1,2-a]pyridin-2-yl)cyclopropane-1-carboxamide;
N-(6-(1H-pyrazol-3-yl)imidazo[1,2-a]pyridin-2-yl)-2-fluorocyclopropane-1-carboxamide;
2-fluoro-N-(6-(4-methyl-1H-pyrazol-3-yl)imidazo[1,2-a]pyridin-2-yl)cyclopropane-1-carboxamide;
N-(6-(1H-pyrrolo[2,3-b]pyridin-5-yl)imidazo[1,2-a]pyridin-2-yl)-2-fluorocyclopropane-1-carboxamide;
2-fluoro-N-(6-(2-methyl-5-(1H-pyrazol-3-yl)phenyl)imidazo[1,2-a]pyridin-2-yl)cyclopropane-1-carboxamide;
2-fluoro-N-(6-(2-oxoindolin-6-yl)imidazo[1,2-a]pyridin-2-yl)cyclopropane-1-carboxamide;
2-fluoro-N-(6-(3-methylthiophen-2-yl)imidazo[1,2-a]pyridin-2-yl)cyclopropane-1-carboxamide;
2-fluoro-N-(6-(5-methyl-2-oxoindolin-4-yl)imidazo[1,2-a]pyridin-2-yl)cyclopropane-1-carboxamide;
2-fluoro-N-(6-(3-methyl-1H-pyrrolo[2,3-b]pyridin-5-yl)imidazo[1,2-a]pyridin-2-yl)cyclopropane-1-carboxamide;
2-fluoro-N-(6-(2-oxo-2,3-dihydrobenzo[d]thiazol-5-yl)imidazo[1,2-a]pyridin-2-yl)cyclopropane-1-carboxamide;
N-(6-(3,5-dimethyl-1H-indol-4-yl)imidazo[1,2-a]pyridin-2-yl)-2-fluorocyclopropanecarboxamide;
N-(6-(1H-pyrrolo[2,3-b]pyridin-5-yl)imidazo[1,2-a]pyridin-2-yl)-2-fluorocyclopropanecarboxamide;
2-fluoro-N-(6-(4-methyl-1H-pyrrolo[2,3-b]pyridin-5-yl)imidazo[1,2-a]pyridin-2-yl)cyclopropanecarboxamide;
N-(6-(4-chloro-1H-pyrrolo[2,3-b]pyridin-5-yl)imidazo[1,2-a]pyridin-2-yl)-2-fluorocyclopropanecarboxamide;
2-fluoro-N-(6-(5-methyl-1H-indol-6-yl)imidazo[1,2-a]pyridin-2-yl)cyclopropanecarboxamide;
2-fluoro-N-(6-(6-methyl-1H-indol-5-yl)imidazo[1,2-a]pyridin-2-yl)cyclopropanecarboxamide;
2-fluoro-N-(6-(5-methyl-1H-benzo[d]imidazol-6-yl)imidazo[1,2-a]pyridin-2-yl)cyclopropanecarboxamide;
2-fluoro-N-(6-(5-methylbenzo[d]oxazol-6-yl)imidazo[1,2-a]pyridin-2-yl)cyclopropanecarboxamide;
2-fluoro-N-(6-(5-methyl-1H-benzo[d]imidazol-4-yl)imidazo[1,2-a]pyridin-2-yl)cyclopropane-1-carboxamide;
2-fluoro-N-(6-(6-methylbenzo[d]thiazol-5-yl)imidazo[1,2-a]pyridin-2-yl)cyclopropanecarboxamide;
2-fluoro-N-(6-(5-methylbenzo[d]oxazol-4-yl)imidazo[1,2-a]pyridin-2-yl)cyclopropanecarboxamide;
2-fluoro-N-(6-(5-methylbenzo[d]thiazol-6-yl)imidazo[1,2-a]pyridin-2-yl)cyclopropanecarboxamide;
2-fluoro-N-(6-(7-methylbenzo[d]thiazol-6-yl)imidazo[1,2-a]pyridin-2-yl)cyclopropanecarboxamide;
2-fluoro-N-(6-(furan-2-yl)imidazo[1,2-a]pyridin-2-yl)cyclopropane-1-carboxamide;
2-fluoro-N-(6-(thiophen-2-yl)imidazo[1,2-a]pyridin-2-yl)cyclopropane-1-carboxamide;
2-fluoro-N-(6-(thiazol-5-yl)imidazo[1,2-a]pyridin-2-yl)cyclopropane-1-carboxamide;
2-fluoro-N-(6-(3-methylisothiazol-5-yl)imidazo[1,2-a]pyridin-2-yl)cyclopropane-1-carboxamide;
2-fluoro-N-(6-(5-methylthiazol-4-yl)imidazo[1,2-a]pyridin-2-yl)cyclopropane-1-carboxamide;
2-fluoro-N-(6-(5-methyl-1H-indol-4-yl)imidazo[1,2-a]pyridin-2-yl)cyclopropane-1-carboxamide;
2-fluoro-N-(6-(2-oxoindolin-6-yl)imidazo[1,2-a]pyridin-2-yl)cyclopropane-1-carboxamide;
2-fluoro-N-(6-(5-methyl-2-oxoindolin-4-yl)imidazo[1,2-a]pyridin-2-yl)cyclopropane-1-carboxamide;
N-(6-(3,5-dimethyl-1H-indol-4-yl)imidazo[1,2-a]pyridin-2-yl)-2-fluorocyclopropanecarboxamide;
2-fluoro-N-(6-(5-methyl-1H-indol-6-yl)imidazo[1,2-a]pyridin-2-yl)cyclopropanecarboxamide;
2-fluoro-N-(6-(6-methyl-1H-indol-5-yl)imidazo[1,2-a]pyridin-2-yl)cyclopropanecarboxamide;
2-fluoro-N-(6-(5-methylbenzo[d]thiazol-6-yl)imidazo[1,2-a]pyridin-2-yl)cyclopropanecarboxamide; and
N-(6-(3-fluoro-2-methylphenyl)imidazo[1,2-a]pyridin-2-yl)cyclopropanecarboxamide.

24. The compound of claim 23, selected from the group consisting of
(1S,2S)-N-(6-(1H-pyrrolo[2,3-b]pyridin-5-yl)imidazo[1,2-a]pyridin-2-yl)-2-fluorocyclopropane-1-carboxamide;
(1S,2S)-2-fluoro-N-(6-(2-oxoindolin-6-yl)imidazo[1,2-a]pyridin-2-yl)cyclopropane-1-carboxamide;
(1S,2S)-2-fluoro-N-(6-(5-methyl-2-oxoindolin-4-yl)imidazo[1,2-a]pyridin-2-yl)cyclopropane-1-carboxamide;
(1S,2S)-2-fluoro-N-(6-(3-methyl-1H-pyrrolo[2,3-b]pyridin-5-yl)imidazo[1,2-a]pyridin-2-yl)cyclopropane-1-carboxamide;

(1S,2S)-2-fluoro-N-(6-(2-oxo-2,3-dihydrobenzo[d]thiazol-5-yl)imidazo[1,2-a]pyridin-2-yl)cyclopropane-1-carboxamide;

(1S,2S)-N-(6-(3,5-dimethyl-1H-indol-4-yl)imidazo[1,2-a]pyridin-2-yl)-2-fluorocyclopropanecarboxamide;

(1S,2S)-N-(6-(1H-pyrrolo[2,3-b]pyridin-5-yl)imidazo[1,2-a]pyridin-2-yl)-2-fluorocyclopropanecarboxamide;

(1S,2S)-2-fluoro-N-(6-(4-methyl-1H-pyrrolo[2,3-b]pyridin-5-yl)imidazo[1,2-a]pyridin-2yl)cyclopropanecarboxamide;

(1S,2S)-N-(6-(4-chloro-1H-pyrrolo[2,3-b]pyridin-5-yl)imidazo[1,2-a]pyridin-2-yl)-2-fluorocyclopropanecarboxamide;

(1S,2S)-2-fluoro-N-(6-(5-methyl-1H-indol-6-yl)imidazo[1,2-a]pyridin-2-yl)cyclopropanecarboxamide;

(1S,2S)-2-fluoro-N-(6-(6-methyl-1H-indol-5-yl)imidazo[1,2-a]pyridin-2-yl)cyclopropanecarboxamide;

(1S,2S)-2-fluoro-N-(6-(5-methyl-1H-benzo[d]imidazol-6-yl)imidazo[1,2-a]pyridin-2-yl)cyclopropanecarboxamide;

(1S,2S)-2-fluoro-N-(6-(5-methylbenzo[d]oxazol-6-yl)imidazo[1,2-a]pyridin-2-yl)cyclopropanecarboxamide;

(1S,2S)-2-fluoro-N-(6-(5-methyl-1H-benzo[d]imidazol-4-yl)imidazo[1,2-a]pyridin-2-yl)cyclopropane-1-carboxamide;

(1S,2S)-2-fluoro-N-(6-(6-methylbenzo[d]thiazol-5-yl)imidazo[1,2-a]pyridin-2-yl)cyclopropanecarboxamide;

(1S,2S)-2-fluoro-N-(6-(5-methylbenzo[d]oxazol-4-yl)imidazo[1,2-a]pyridin-2-yl)cyclopropanecarboxamide;

(1S,2S)-2-fluoro-N-(6-(5-methylbenzo[d]thiazol-6-yl)imidazo[1,2-a]pyridin-2-yl)cyclopropanecarboxamide;

(1S,2S)-2-fluoro-N-(6-(7-methylbenzo[d]thiazol-6-yl)imidazo[1,2-a]pyridin-2-yl)cyclopropanecarboxamide;

(1S,2S)-2-fluoro-N-(6-(5-methyl-1H-indol-4-yl)imidazo[1,2-a]pyridin-2-yl)cyclopropane-1-carboxamide;

(1S,2S)-2-fluoro-N-(6-(2-oxoindolin-6-yl)imidazo[1,2-a]pyridin-2-yl)cyclopropane-1-carboxamide; and (1S,2S)-2-fluoro-N-(6-(5-methyl-1H-benzo[d]imidazol-6-yl)imidazo[1,2-a]pyridin-2-yl)cyclopropanecarboxamide.

\* \* \* \* \*